US008138314B2

(12) United States Patent
Exley et al.

(10) Patent No.: US 8,138,314 B2
(45) Date of Patent: Mar. 20, 2012

(54) COMPOSITIONS AND METHODS OF MONOCLONAL AND POLYCLONAL ANTIBODIES SPECIFIC FOR T CELL SUBPOPULATIONS

(75) Inventors: Mark A. Exley, Chestnut Hill, MA (US); Samuel B. Wilson, Lexington, MA (US); Steven P. Balk, Needham, MA (US)

(73) Assignees: Beth Israel Deaconess Medical Center, Inc., Boston, MA (US); Dana-Farber Cancer Institute, Boston, MA (US); The General Hospital Corporation, Boston, MA (US)

( * ) Notice: Subject to any disclaimer, the term of this patent is extended or adjusted under 35 U.S.C. 154(b) by 1135 days.

(21) Appl. No.: 11/541,958

(22) Filed: Oct. 2, 2006

(65) Prior Publication Data

US 2007/0160600 A1    Jul. 12, 2007

Related U.S. Application Data

(63) Continuation of application No. 09/885,768, filed on Jun. 19, 2001, now abandoned.

(60) Provisional application No. 60/212,466, filed on Jun. 19, 2000.

(51) Int. Cl.
*C12P 21/08* (2006.01)
(52) U.S. Cl. ............................... 530/387.3; 530/388.22
(58) Field of Classification Search ........................ None
See application file for complete search history.

(56) References Cited

U.S. PATENT DOCUMENTS 5,853,737 A    12/1998    Modlin et al.

FOREIGN PATENT DOCUMENTS

| EP | 0 677 533 | 10/1995 |
| EP | 1 025 854 | 8/2000 |
| WO | WO 99/34209 | 7/1999 |

OTHER PUBLICATIONS

Exley et al., Current Protocols in Immunology (2002) 14.11.1-14.11.13.*
Satoh et al., J Immunol. Nov. 1, 1996;157(9):3886-92.*
Smiley et al., Science. Feb. 14, 1997;275(5302):977-9.*
Kuhnlein et al., J Immunol. Aug. 1, 1994;153(3):979-86.*
Sido et al., Eur. J. Immunol. 1998. 28: 1347-1357.*
Behar et al., J Immunol. Jan. 1, 1999;162(1):161-7.*
Janeway et al., Immunobiology, 5th Ed., Garland Science, pp. 94-105 (2001).*
Laune et al., Clinical Chemistry and Laboratory Medicine. vol. 36, Issue 6, pp. 367-371.*
Bendelac et al., "Mouse CD1-Specific NK1 T Cells: Development, Specificity, and Function," *Annu Rev Immunol.* 15:535-562 (1997).
Bender et al., "T Cell Receptor Repertoire in Polymyositis: Clonal Expansion of Autoaggressive CD8+ T Cells," *J Exp Med.* 181:1863-1868 (1995).
Benlagha et al., "In Vivo Identification of Glycolipid Antigen-Specific T Cells Using Fluorescent CD1d Tetramers," *J Exp Med.* 191:1895-1903 (2000).
Blumberg et al., "Human Intestinal Intraepithelial Lymphocytes Are Derived from a Limited Number of T Cell Clones That Utilize Multiple Vβ T Cell Receptor Genes[1]," *J Immunol.* 150:5144-5153 (1993).
Camaud et al., "Cutting Edge: Cross-talk Between Cells of the Innate Immune System: NKT Cells Rapidly Activate NK Cells," *J Immunol.* 163:4647-4650 (1999).
Campbell, *Monoclonal Antibody Technology*. Elsever Science, Publishers B.V., second edition, p. 29 (1985).
Chott et al., "A Common TCR β-Chain Expressed by CD8+ Intestinal Mucosa T Cells in Ulcerative Colitis," *J Immunol.* 156:3024-3035 (1996).
Cui et al., "Requirement for $V_\alpha 14$ NKT Cells in IL-12-mediated Rejection of Tumors," *Science.* 278:1623-1626 (1997).
Dellabona et al., "An Invariant Vα24-JαQ/Vβ11 T Cell Receptor Is Expressed in All Individuals by Clonally Expanded CD4−8− T Cells," *J Exp Med.* 180:1171-1176 (1994).
Exley et al., "A Major Fraction of Human Bone Marrow Lymphocytes are Th2-Like CD1d-Reactive T Cells That Can Suppress Mixed Lymphocyte Responses," *J Immunol.* 167:5531-5534 (2001).
Exley et al., "CD161 (NKR-P1A) Costimulation of CD1d-dependent Activation of Human T Cells Expressing Invariant Vα24JαQ T Cell Receptor α Chains," *J Exp Med.* 188:867-876 (1998).
Exley et al., "CD1d Structure and Regulation on Human Thymocytes, Peripheral Blood T Cells, B Cells and Monocytes," *Immunology.* 100:37-47 (2000).
Exley et al., "CD1d-reactive T-Cell Activation Leads to Amelioration of Disease Caused by Diabetogenic Encephalomyocarditis Virus," *J Leukoc Biol.* 69:713-718 (2001).
Exley et al., "Requirements for CD1d Recognition by Human Invariant Vα24+ CD4−CD8− T Cells," *J Exp Med.* 186:109-120 (1997).
Falcone et al., "A Defect in Interleukin 12-induced Activation and Interferon γ Secretion of Peripheral Natural Killer T Cells in Nonobese Diabetic Mice Suggests New Pathogenic Mechanisms for Insulin-dependent Diabetes Mellitus," *J Exp Med.* 190:963-972 (1999).
Farace et al., "T Cell Repertoire in Patients with B Chronic Lymphocytic Leukemia. Evidence for Multiple in vivo T Cell Clonal Expansions.," *J Immunol.* 153:4281-4290 (1994).
Fitzgerald et al., "Analysis Of Clonal CD8+ T Cell Expansions in Normal Individuals and Patients with Rheumatoid Arthritis," *J Immunol.* 154:3538-3547 (1995).
Gavilondo et al., "Antibody Engineering at the Millennium," *Biotechniques.* 29:128-145 (2000).
Gorochov et al., "Oligoclonal Expansion of CD8+ CD57+ T Cells with Restricted T-Cell Receptor β Chain Variability after Bone Marrow Transplantation," *Blood.* 83:587-595 (1994).
Grunewald et al., "CD4+ and CD8+ T Cell Expansions Using Selected TCR V and J Gene Segments at the Onset of Giant Cell Arteritis," *Arthritis Rheum.* 37:1221-1227 (1994).

(Continued)

Primary Examiner — Zachary Skelding
(74) Attorney, Agent, or Firm — Clark & Elbing, LLP; Kristina Bieker-Brady

(57) ABSTRACT

The invention provides compounds and methods for the ex vivo or in vivo expansion of NK T cells, CD1d-reactive T cells, and JαQ+ T cells, and the modulation of their activities. These compounds and methods have diagnostic and therapeutic applications.

13 Claims, 37 Drawing Sheets

OTHER PUBLICATIONS

Harlow et al., "Labeling Antibodies," *Antibodies: A Laboratoy Manual*. Cold Spring Harbor Laboratory Press, pp. 321-322 (1988).
Hingorani et al., "Oligoclonality of Vβ3 TCR Chains in the CD8[30] T Cell Population of Rheumatoid Arthritis Patients," *J Immunol*. 156:852-858 (1996).
Hong et al., "Immune Privilege: Keeping an Eye on Natural Killer T Cells," *J Exp Med*. 190:1197-1200 (1999).
Illés et al., "Differential Expression of NK T Cell Vα24JαQ Invariant TCR Chain in the Lesions of Multiple Sclerosis and Chronic Inflammatory Demyelinating Polyneuropathy," *J Immunol*. 164:4375-4381 (2000).
Ito et al., "Involvement of Decidual Vα14 NKT Cells in Abortion," *Proc Nati Acad Sci U.S.A.* 97:740-744 (2000).
Jameson et al., "The T Cell Receptor Vα11 Gene Family. Analysis of Allelic Sequence Polymorphism and Demonstration of Jα Region-dependent Recognition by Allele-specific Antibodies," *J Immunol*. 147:3185-3193 (1991).
Janeway et al., "T-cell Receptor Diversity Is Focused in CDR3," *Immunobiology*. Garland Publishing, 3rd edition, p. 4:36 (1997).
Johnson et al., "Kabat Database and its Applications: Future Directions," *Nucleic Acids Res*. 29:205-206 (2001).
Kawano et al., "Antitumor Cytotoxicity Mediated by Ligand-activated Human Vα24 NKT Cells," *Cancer Res*. 59:5102-5105 (1999).
Kent et al., "Noncanonical Vα24JαQ T Cells with Conservative α Chain CDR3 Region Amino Acid Substitutions are Restricted by CD1d," *Hum Immunol*. 60:1080-1089 (1999).
Kuwana et al., "Highly Restricted TCR-αβ Usage by Autoreactive Human T Cell Clones Specific for DNA Topoisomerase I," *J. Immunol*. 158:485-491 (1997).
Maldonado-Lopez et al., "CD8α[+] and CD8α[−] Subclasses of Dendritic Cells Direct the Development of Distinct T Helper Cells in vivo," *J Exp Med*. 189:587-592 (1999).
Matsuda et al., "Tracking the Response of Natural Killer T Cells to a Glycolipid Antigen Using Cd1d Tetramers," *J Exp Med*. 192:741-753 (2000).
Milner et al., "Differential Responses of Invariant Vα24JαQ T Cells and MHC Class II-Restricted CD4[+] T Cells to Dexamethasone," *J Immunol*. 163:2522-2529 (1999).
Monson et al., "Differential Expression of NKT Cells (Vα24JαQ[+]) in Multiple Sclerosis Patients with either Primary Progressive or Relapsing Remittng Disease," *J Neuroimmunol*. 118:87 (2001) (abstract).
Moss et al., "Clonal Populations of CD4[30] and CD8[+] T Cells in Patients with Multiple Myeloma and Paraproteinemia," *Blood*. 87:3297-3306 (1996).
Naidenko et al., "Binding and Antigen Presentation of Ceramide-containing Glycolipids by Soluble Mouse and Human CD1d Molecules," *J Exp Med*. 190:1069-1079 (1999).
Nicol et al., "Human Invariant Vα24[+] Natural Killer T Cells Activated by α-galactosylceramide (KRN7000) Have Cytotoxic Antitumour Activity through Mechanisms Distinct from T Cells and Natural Killer Cells," *Immunology*. 99:229-234 (2000).
Porcelli et al., "Analysis of T Cell Antigen Receptor (TCR) Expression by Human Peripheral Blood CD4[−]8[−] α/β T Cells Demonstrates Preferential Use of Several Vβ Genes and an Invariant TCR α Chain," *J Exp Med*. 178:1-16 (1993).
Porcelli et al., "The CD1 System: Antigen-presenting Molecules for T Cell Recognition of Lipids and Glycolipids," *Annu Rev Immunol*. 17:297-329 (1999).
Probert et al., "Persistent Clonal Expansions of Peripheral Blood CD4[30] Lymphocytes in Chronic Inflammatory Bowel Disease," *J Immunol*. 157:3183-3191 (1996).
Prussian et al., "TCR Vα24 and Vβ11 Coexpression Defines a Human NK1 T Cell Analog Containing a Unique Th0 Subpopulation[1]," *J Immunol*. 159:5862-5870 (1997).
Reinherz et al., "The Crystal Structure of a T Cell Receptor in Complex with Peptide and MHC Class II," *Science*. 286:1913-1921 (1999).
Reid et al., "The Control of T Cell Responses by Dendritic Cell Subsets," *Curr Opin Innumol*. 12:114-121 (2000).
Rissoan et al., "Reciprocal Control of T Helper Cell and Dendritic Cell Differentiation," *Science*. 283:1183-1186 (1999).
Shigematsu et al., "Usage of T Cell Receptor (TCR) V β Gene in Ulcerative Colitis," *J Clin Lab Immunol*. 48:177-186 (1996).
Sonoda et al., "CD1-Reactive Natural Killer T Cells Are Required for Development of Systemic Tolerance Through an Immune-privileged Site," *J Exp Med*. 190:1215-1225 (1999).
Sottini et al., "Selection of T Lymphocytes in Two Rheumatoid Arthritis Patients Defines Different T-Cell Receptor Vβ Repertoires in CD4[30] and CD8[30] T-Cell Subsets," *J Autoimmun*. 6:621-637 (1993).
Streilein et al., "Immune Deviation in Relation to Ocular Immune Privilege," *J Immunol*. 158:3557-3560 (1997).
Streilein et al., "Immune Privilege, T-Cell Tolerance, and Tissue-restricted Autoimmunity," *Hum Immunol*. 52:138-143 (1997).
Uyemura et al., "CD4[+] Type 1 and CD8[+] Type 2 T Cell Subsets in Human Leishmaniasis Have Distinct T Cell Receptor Repertoires," *J Immunol*. 151:7095-7104 (1993).
van der Vliet et al., "Circulating Vα24[+] Vβ11[+] NKT Cell Numbers Are Decreased in a Wide Variety of Diseases That Are Characterized by Autoreactive Tissue Damage," *Clin Immunol*. 100:144-148 (2001).
van der Vliet et al., "Effects of β-Galactosylceramide (KRN7000), Interleukin-12 and Interleukin-7 on Phenotype and Cytokine Profile of Human Vα24[+] Vβ11[+] T Cells," *Immunology*. 98:557-563 (1999).
van der Vliet et al., "Potent Expansion of Human Natural Killer T Cells using α-Galactosylceramide (KRN7000)-loaded Monocyte-derived Dendritic Cells, Cultured in the Presence of IL-7 and IL-15," *J Immunol Methods*. 247:61-72 (2001).
Wilson et al., "Development of Monoclonal Antibodies to Vα24JαQ T Cells Detects Alterations in Cell Frequency in New-onset Type 1 Diabetes Patients," *Diabetes*. 50(Supple. 2):A267 (2001).
Wilson et al., "Extreme Th1 Bias in Invariant Vα24JαQ T Cells in Type 1 Diabetes," *Nature*. 391:177-181 (1998).
Wilson et al., "Extreme Th1 Bias of Invariant Vα24JαQ T Cells in Type 1 Diabetes," *Nature*. 399:84 (1999).
Wilson et al., "Multiple Differences in Gene Expression in Regulatory Vα24JαQ T Cells from Identical Twins Discordant for Type 1 Diabetes," *Proc Natl Acad. Sci U.S.A.* 97:7411-7416 (2000).
Wucherpfennig et al., "T Cell Receptor $V_\alpha$-$V_\beta$ Repertoire and Cytokine Gene Expression in Active Multiple Sclerosis Lesions," *J Exp Med*. 175:993-1002 (1992).
Yang et al., "CD1d on Myeloid Dendritic Cells Stimulates Cytokine Secretion from and Cytolytic Activity of Vα24JαQ T Cells: A Feedback Mechanism for Immune Regulation," *J Immunol*. 165:3756-3762 (2000).
International Search Report mailed Sep. 12, 2002 (PCT/US01/19670).
Yoshino and Haruo, Annual Review Immunity 1998, "Antigen Presentation/MHC: Mutual Interaction Between T Cell Receptor and MHC, Molecular Structure," 176-187, 1998, (Translation enclosed).
Ono, Annual Review Immunity 2000, "Cross-Recognition and TCR Conformation of Peptide/MHC," 88-97, 1999. (Translation enclosed).
Translation of Office Action from Japan Patent Application 2002-504312, dated Mar. 10, 2011.
van der Vliet et al. "Circulating myeloid dendritic cells of advanced cancer patients result in reduced activation and a biased cytokine profile in invariant NKT cells," *J Immunol*. 180:7287-7293 (2008).
Extended European Search Report for Application No. 10012392.6-1222, dated Dec. 13, 2011.

* cited by examiner

Figure 12

| Miltenyi vs. Dynal 4/11/01 | | | |
|---|---|---|---|
| | PBMC | Dynal @ 40 | Miltenyi @ 20 |
| Donor 1 | | | |
| Vα24/6B11 | 0 | 8.46 | 4.53 |
| Vα24/Vβ11 | 0.01 | 4.85 | 4.71 |
| Vα24 | | 3.9 | |
| Donor 2 | | | |
| Vα24/6B11 | 0.01 | 0.99 | 5.91 |
| Vα24/Vβ11 | 0.01 | 1.47 | 6.16 |
| Vα24 | | 0.33 | |
| Donor 3 | | | |
| Vα24/6B11 | 0 | N/A | 71 |
| Vα24/Vβ11 | 0.03 | N/A | 72 |
| Vα24 | | | 5.98 |
| LKP 21 unsorted control | | | |
| Vα24/6B11 | 0.01 | | |
| Vα24/Vβ11 | 0 | | |

Figure 13

| Dynal Bead 1/19/01 | | |
|---|---|---|
| LKP 10 on 40 ug/ml 6B11 on TCM | | |
| | Vα24/Vβ11 | 32.98 |
| | Vα24/6B11 | 32 |
| LKP 10 on TCM + IL15/IL7 | | |
| | Vα24/Vβ11 | 12.46 |
| | Vα24/6B11 | 29 |
| LKP 10 on TCM + dex | | |
| | Vα24/Vβ11 | 17.08 |
| | Vα24/6B11 | 19 |
| LKP 10 on TCM + IL15/IL7+dex | | |
| | Vα24/Vβ11 | 4.93 |
| | Vα24/6B11 | 13.81 |

| Dynal 6B11 Bead Prep 3/9/01 | | |
|---|---|---|
| LKP 14 unsorted control | | |
| 3/20/01 | Vα24/Vβ11 | 0.02% |
| | Vα24/6B11 | 0.01% |
| LKP 14 6B11 + PHA + auto APC | | |
| 3/20/01 | Vα24/Vβ11 | 0.09% |
| | Vα24/6B11 | 0% |
| 4/20/01 | Vα24/Vβ11 | 0.13% |
| | Vα24/6B11 | 0.00% |
| | Vα24 | 0.01% |
| LKP 14  6B11 + auto APC | | |
| 3/20/01 | Vα24/Vβ11 | 0.68% |
| | Vα24/6B11 | 0.02% |
| 4/20/01 | Vα24/Vβ11 | 0.15% |
| | Vα24/6B11 | 0.00% |
| | Vα24 | 0.73% |
| 4/27/01 | alpha Gal Cer stim | |
| 5/10/01 | Vα24/Vβ11 | 2.73% |
| | Vα24/6B11 | 2.94% |
| unsorted control | | |
| | Vα24/Vβ11 | 0.01% |
| | Vα24/6B11 | 0.01% |
| 6B11 + PHA + auto APC | | |
| 4/20/01 | Vα24/Vβ11 | 3.64% |
| | Vα24/6B11 | 3.75% |
| 5/10/01 | Vα24/Vβ11 | 5.01% |
| | Vα24/6B11 | 4.92% |

Figure 15

| Dynal 6B 11 Bead Prep 3/9/01 | | |
|---|---|---|
| LKP 13 unsorted control | | |
| | Vα24/Vβ11 | 0.07% |
| | Vα24/6B11 | 0.06% |
| LKP 13 6B11 + PHA + allo APC | | |
| 4/20/01 | Vα24/Vβ11 | 1.85% |
| | Vα24/6B11 | 0% |
| | Vα24 | 1.16% |
| 5/10/01 | Vα24/Vβ11 | 14.29% |
| | Vα24/6B11 | |
| unsorted control | | |
| | Vα24/Vβ11 | 0.01% |
| | Vα24/6B11 | 0.00% |
| 6B11 + PHA + auto APC | | |
| 4/20/01 | Vα24/Vβ11 | 0.05% |
| | Vα24/6B11 | 0.06% |
| | Vα24 | 3.22% |
| 6B11 + auto APC | | |
| 4/20/01 | Vα24/Vβ11 | 0.78% |
| | Vα24/6B11 | 0.00% |
| | Vα24 | 1% |
| | | |
| | | |
| | | |
| | | |
| | | |

Figure 16

| Miltenyi Prep #1 6B11 | | 1/01 |
|---|---|---|
| LKP2 +auto APC on TCM | | |
| 2/6/01 | Vα24/Vβ11 | 26.07% |
| | Vα24/6B11 | 21% |
| 2/23/01 | Vα24/6B11 | 10.79% |
| 3/26/01 | alpha Gal Cer stim | |
| 4/20/01 | Vα24/Vβ11 | 73.40% |
| | Vα24/6B11 | 74.66% |
| 4/27/01 | alpha Gal Cer stim | |
| 5/14/01 | Vα24/Vβ11 | 80.87% |
| | Vα24/6B11 | 79.98% |
| LKP2 +auto APC on TCM + IL7/IL15 | | |
| 2/6/01 | Vα24/Vβ11 | 16% |
| | Vα24/6B11 | 11% |
| 3/26/01 | alpha Gal Cer stim | |
| 4/20/01 | Vα24/Vβ11 | 54.28% |
| | Vα24/6B11 | 56.89% |
| 4/27/01 | alpha Gal Cer stim | |
| 5/14/01 | Vα24/Vβ11 | 68.05% |
| | Vα24/6B11 | 68.85% |
| | Vα24 | 1.66% |

Figure 17

| Miltenyi Prep #2 | | 1/01 |
|---|---|---|
| LKP 11 on Vα24 + auto APC + PHA | | |
| 2/23/01 | Vα24/6B11 | 63.75% |
| 3/20/01 | Vα24/Vβ11 | 1.43% |
|  | Vα24/6B11 | 0.07% |
| 4/27/01 | alpha Gal Cer stim | |
| 5/10/01 | Vα24/Vβ11 | 24.78% |
|  | Vα24/6B11 | 14.94% |
| LKP 11 on 6B11 + auto APC +PHA | | |
| 2/23/01 | Vα24/6B11 | 45.27% |
| LKP 12 on Vα24 + auto APC + PHA | | |
| 2/23/01 | Vα24/6B11 | 33.51% |
| 3/20/01 | Vα24/Vβ11 | 0.25% |
|  | Vα24/6B11 | 0.25% |
| 4/27/01 | alpha Gal Cer stim | |
| 5/14/01 | Vα24/Vβ11 | 0.00% |
|  | Vα24/6B11 | 0.00% |
|  | Vα24 | 55.00% |

A  Healthy Donor

B  Prostate Cancer

C  Remission

NK-T Dendritic Cell Study
Sero-Negatives

| Date | Patient ID | Name | Serostatus | CD4 ABS | HIV copies/ml | Lymph Count | T-Cell Count | NK-T Count | % NK-T II Lymph | ABS Lymph | ABS NK-T | % NK-T II CD3 | % CD123+ DC II Leuk | % CD11c+ DC II Leuk | WBC | ABS CD123+DC | ABS CD11c+DC |
|---|---|---|---|---|---|---|---|---|---|---|---|---|---|---|---|---|---|
| 5/3/00 | Yang | | 0 | | | 44728 | 27503 | 44 | 0.0984 | | 0.0000 | 0.1600 | *** | *** | | *** | *** |
| 5/9/00 | 91841 | | 0 | 927 | | 79175 | 64673 | 74 | 0.0935 | 1782 | 1.6655 | 0.1144 | *** | *** | 5400 | *** | *** |
| 5/11/00 | 42893 | | 0 | | | 67709 | 47828 | 1 | 0.0015 | | 0.0000 | 0.0021 | *** | *** | | *** | *** |
| 5/18/00 | 91921 | | 0 | 787 | | 47660 | 32443 | 4 | 0.0084 | 1749 | 0.1468 | 0.0123 | *** | *** | 5300 | *** | *** |
| 5/24/00 | 91960 | | 0 | 621 | | 33001 | 26942 | 166 | 0.5030 | 1150 | 5.7847 | 0.6161 | *** | *** | 5000 | *** | *** |
| 5/25/00 | 91960* | | 0 | 621 | | 33855 | 27347 | 206 | 0.6085 | 1150 | 6.9975 | 0.7533 | *** | *** | 5000 | *** | *** |
| 5/30/00 | 92001 | | 0 | 898 | | 65330 | 46630 | 48 | 0.0735 | 1632 | 1.1991 | 0.1029 | *** | *** | 4800 | *** | *** |
| 6/6/00 | 92065 | | 0 | 735 | | 61812 | 50967 | 15 | 0.0243 | 1634 | 0.3965 | 0.0294 | *** | *** | 3800 | *** | *** |
| 8/14/00 | 92145 | | 0 | 796 | | 84897 | 56717 | 28 | 0.0308 | 1768 | 0.5415 | 0.0458 | *** | *** | 5200 | *** | *** |
| 8/24/00 | 92873 | | 0 | 821 | | 76582 | 51494 | 45 | 0.0588 | 2160 | 1.2692 | 0.0874 | 0.170 | 0.320 | 4000 | 6.80 | 12.80 |
| 9/8/00 | 40211 | | 0 | 1040 | | 96769 | 78778 | 56 | 0.0579 | 2040 | 1.1805 | 0.0711 | 0.057 | 0.027 | 5100 | 2.93 | 1.37 |
| 9/8/00 | 92800 | | 0 | 957 | | 82627 | 63397 | 31 | 0.0375 | 1740 | 0.6528 | 0.0489 | 0.043 | 0.084 | 5800 | 2.47 | 4.85 |
| 1/24/01 | 42959 | | 0 | 0 | | 153419 | 112395 | 19 | 0.0124 | | 0.0000 | 0.0169 | 0.032 | 0.051 | | 0.00 | 0.00 |
| 1/25/01 | 40545 | | 0 | 853 | | 79252 | 44870 | 15 | 0.0189 | 1452 | 0.2748 | 0.0334 | 0.135 | 0.358 | 3300 | 4.47 | 11.81 |
| 1/25/01 | 40834 | | 0 | 583 | | 44101 | 36543 | 1 | 0.0023 | 1122 | 0.0254 | 0.0027 | 0.050 | 0.086 | 5100 | 2.55 | 4.39 |
| 1/31/01 | 41214 | | 0 | *** | | *** | *** | *** | *** | *** | *** | *** | 0.088 | 0.084 | | 0.00 | 0.00 |
| 1/31/01 | 42888 | | 0 | *** | | *** | *** | *** | *** | *** | *** | *** | 0.073 | 0.062 | | 0.00 | 0.00 |
| 2/1/01 | 40086 | | 0 | 850 | | 76313 | 67231 | 42 | 0.0550 | 1700 | 0.9356 | 0.0625 | 0.086 | 0.240 | 5000 | 4.31 | 11.98 |
| 2/1/01 | 40128 | | 0 | 689 | | 61816 | 47823 | 22 | 0.0356 | 1377 | 0.4901 | 0.0460 | 0.030 | 0.043 | 5100 | 1.54 | 2.21 |
| 2/22/01 | 40059 | | 0 | | | 111766 | 85872 | 5 | 0.0045 | | 0.0000 | 0.0058 | 0.040 | 0.085 | | 0.00 | 0.00 |
| 2/28/01 | 41842 | | 0 | | | 62325 | 48159 | 12 | 0.0193 | | 0.0000 | 0.0249 | 0.111 | 0.264 | | 0.00 | 0.00 |

Serostatus: 0=seronegative, 1=HIV-1Infected, 2=HIV-1 Seroconverter, 3=AIDS
>0.02% NK-Tcells II lymphs considered positive       *5/25/00 (91969 blood is 24 hrs. old)

FIG. 23B

NK-T Dendritic Cell Study
Sero-Positives

| Date | Patient ID | Name | Serosatus | CD4 ABS | HIV copies/ml | Lymph Count | T-Cell Count | NK-T Count | % NK-T II Lymph | ABS Lymph | ABS NK-T | % NK-T II CD3 | % CD123+ DC II Leuk | % CD11c+ DC II Leuk | WBC | ABS CD123+DC | ABS CD11c+DC |
|---|---|---|---|---|---|---|---|---|---|---|---|---|---|---|---|---|---|
| 5/25/00 | 40263 | | 1 | 635 | 2257 | 79350 | 50332 | 6 | 0.0076 | 1813 | 0.1371 | 0.0119 | ... | ... | 3700 | ... | ... |
| 6/1/00 | 41989 | | 1 | 699 | 0 | 81811 | 63503 | 250 | 0.3056 | 2254 | 6.8878 | 0.3937 | ... | ... | 4600 | ... | ... |
| 6/14/00 | 40946 | | 3 | 559 | 0 | 98766 | 74485 | 3 | 0.0030 | 2432 | 0.0739 | 0.0040 | ... | ... | 7600 | ... | ... |
| 6/15/00 | 45555 | | 1 | 668 | 30300 | 93116 | 55888 | 11 | 0.0118 | 2088 | 0.2467 | 0.0197 | ... | ... | 7200 | ... | ... |
| 6/15/00 | 41400 | | 3 | 199 | 167000 | 50249 | 43105 | 6 | 0.0119 | 1107 | 0.1322 | 0.0139 | ... | ... | 4100 | ... | ... |
| 8/28/00 | 42946 | | 1 | 768 | 212000 | 76925 | 63905 | 12 | 0.0156 | 2193 | 0.3421 | 0.0188 | 0.070 | 0.260 | 5100 | 3.57 | 13.26 |
| 9/6/00 | 20461 | | 1 | 671 | 308 | 181054 | 111247 | 3 | 0.0017 | 3726 | 0.0617 | 0.0027 | 0.023 | 0.023 | 8100 | 1.82 | 1.87 |
| 9/8/00 | 40177 | | 1 | 858 | 0 | 73001 | 54950 | 8 | 0.0110 | 1530 | 0.1677 | 0.0146 | 0.027 | 0.090 | 5100 | 1.37 | 4.58 |
| 1/24/01 | 41411 | | 2 | 977 | | 108212 | 88856 | 34 | 0.0314 | 2640 | 0.8295 | 0.0383 | 0.151 | 0.266 | 6000 | 9.03 | 15.98 |
| 1/26/01 | 40360 | | 2 | ... | ... | ... | ... | ... | ... | ... | ... | ... | 0.083 | 0.132 | | 0.00 | 0.00 |
| 2/7/01 | 41266 | | 1 | 354 | | 48310 | 35405 | 1 | 0.0021 | 1219 | 0.0252 | 0.0028 | 0.040 | 0.137 | 5300 | 2.14 | 7.28 |
| 2/7/01 | 40646 | | 2 | 0 | | 55088 | 46321 | 2 | 0.0036 | | 0.0000 | 0.0043 | 0.078 | 0.139 | | 0.00 | 0.00 |
| 2/8/01 | 41329 | | 1 | 0 | | 86792 | 78696 | 5 | 0.0058 | | 0.0000 | 0.0064 | 0.072 | 0.075 | | 0.00 | 0.00 |
| 2/8/01 | 42964* | | (unknown) | 0 | | 62696 | 52449 | 10 | 0.0159 | | 0.0000 | 0.0191 | 0.031 | 0.038 | | 0.00 | 0.00 |
| 2/14/01 | 42946 | | (unknown) | 0 | | 103913 | 83889 | 54 | 0.0520 | | 0.0000 | 0.0644 | 0.039 | 0.124 | | 0.00 | 0.00 |
| 2/22/01 | 41977 | | 1 | | | 121798 | 95033 | 25 | 0.0205 | | 0.0000 | 0.0263 | 0.022 | 0.029 | | 0.00 | 0.00 |
| 3/1/01 | 40605 | | 4 | | | 86319 | 71338 | 29 | 0.0336 | | 0.0000 | 0.0407 | 0.088 | 0.092 | | 0.00 | 0.00 |

Serosatus: 0=seronegative, 1=HIV-1 Infected, 2=HIV-1 Seroconverter, 3=AIDS
>0.02% NK-Tcells II lymphs considered positive     *5/25/00 (91969 blood is 24 hrs. old)

FIG. 23C

| Date | Patient ID | Serosatus | CD4 ABS | HIV copies/ml | Lymph Count | T-Cell Count | NK-T Count | % NK-T II Lymph | % NK-T II CDe | CD123+ DC II Leuk | CD11c+ DC II Leuk |
|---|---|---|---|---|---|---|---|---|---|---|---|
| | SERONEGATIVES | | | | | | | | | | |
| 5/3/00 | 91841 | 0 | | | 44728 | 27503 | 51 | 0.1140 | 0.1854 | | |
| 5/9/00 | 42893 | 0 | | | 79175 | 64673 | 74 | 0.0935 | 0.1144 | | |
| 5/11/00 | 91921 | 0 | | | 67709 | 47828 | 1 | 0.0015 | 0.0021 | | |
| 5/18/00 | 91960 | 0 | | | 47660 | 32443 | 4 | 0.0084 | 0.0123 | | |
| 5/24/00 | 92001 | 0 | | | 33001 | 26942 | 166 | 0.5030 | 0.6161 | | |
| 5/30/00 | 92065 | 0 | | | 65330 | 46630 | 48 | 0.0735 | 0.1029 | | |
| 6/6/00 | 92145 | 0 | | | 61812 | 50967 | 15 | 0.0243 | 0.0294 | | |
| 6/14/00 | 92673 | 0 | | | 84497 | 56717 | 26 | 0.0306 | 0.0458 | 0.17 | 0.32 |
| 8/28/00 | 92800 | 0 | | | 76582 | 51494 | 45 | 0.0588 | 0.0874 | 0.04 | 0.08 |
| 9/8/99 | 40211 | 0 | 1040 | | 82887 | 63390 | 31 | 0.0375 | 0.0489 | 0.06 | 0.03 |
| 9/8/99 | | | | 0 | 98769 | 78774 | 56 | 0.0579 | 0.0711 | | |
| | mean | | | | 67304.545 | 49760.09 | 47 | 0.091168895 | 0.119637 | 0.09 | 0.143333333 |
| | SD | | | | 19359.286 | 16224.34 | 45.47307 | 0.140902923 | 0.17276109 | 0.07 | 0.155026879 |
| | SEROPOSITIVES (DETECTABLE) | | | | | | | | | | |
| 9/8/99 | 20461 | 1 | 671 | 308 | 181054 | 111237 | 3 | 0.0017 | 0.0027 | 0.02 | 0.02 |
| 5/25/00 | 40263 Visit 330 | 1 | 835 | 2257 | 79350 | 50332 | 6 | 0.0076 | 0.0119 | | |
| 6/15/00 | 45555 Visit 335 | 1 | 868 | 30300 | 93116 | 55888 | 11 | 0.0118 | 0.0197 | | |
| 6/15/00 | 41400 Visit 330 | 3 | 199 | 167000 | 50249 | 43105 | 6 | 0.0119 | 0.0139 | | |
| 8/28/00 | 42946 | 1 | 768 | | 76925 | 63905 | 12 | 0.0156 | 0.0188 | 0.07 | 0.26 |
| | mean | | | | 96138.8 | 64893.4 | 7.6 | 0.009714354 | 0.01339948 | 0.045 | 0.14 |
| | SD | | | | 49941.556 | 27002.65 | 3.781534 | 0.005328085 | 0.00068081 | 0.035355339 | 0.169705627 |
| | SEROPOSITIVES (UNDETECTABLE) | | | | | | | | | | |
| 9/8/99 | 40177 | 1 | 658 | 0 | 73001 | 54946 | 8 | 0.0110 | 0.0146 | 0.03 | 0.09 |
| 6/1/00 | 41989 Visit 335 | 1 | 699 | 0 | 81811 | 63503 | 250 | 0.3056 | 0.3937 | | |
| 6/14/00 | 40846 Visit 330 | 3 | 559 | 0 | 98766 | 74485 | 3 | 0.0030 | 0.0040 | | |
| 8/28/00 | 42946 | 1 | 768 | | 76925 | 63905 | 12 | 0.0156 | 0.0188 | 0.07 | 0.26 |
| | mean | | | | 82625.75 | 64209.75 | 68.25 | 0.083794556 | 0.10776187 | 0.05 | 0.175 |
| | SD | | | | 11347.626 | 7999.796 | 121.2226 | 0.147949462 | 0.19071445 | 0.028284271 | 0.120208153 |
| | ALL SEROPOSITIVES | | | | | | | | | | |

FIG. 23D

| Date | Patient ID | Serostatus | CD4 ABS | HIV copies/ml | Lymph Count | T-Cell Count | NK-T Count | % NK-T /Lymph | % NK-T /CD3 | CD123+ DC /Leuk | CD11c+ DC /Leuk |
|---|---|---|---|---|---|---|---|---|---|---|---|
| 9/8/99 | 20461 | 1 | 671 | 308 | 181054 | 111237 | 3 | 0.0017 | 0.0027 | 0.02 | 0.02 |
| 5/25/00 | 40263 Visit 330 | 1 | 635 | 2257 | 79950 | 50332 | 6 | 0.0076 | 0.0119 | | |
| 6/15/00 | 45555 Visit 335 | 1 | 668 | 30300 | 93116 | 55888 | 11 | 0.0118 | 0.0197 | | |
| 6/15/00 | 41400 Visit 330 | 3 | 199 | 167000 | 50249 | 43105 | 6 | 0.0119 | 0.0139 | | |
| 8/28/00 | 42946 | 1 | 768 | | 76925 | 63905 | 12 | 0.0156 | 0.0188 | 0.07 | 0.26 |
| 9/8/99 | 40177 | 1 | 658 | 0 | 73001 | 54946 | 8 | 0.0110 | 0.0146 | 0.03 | 0.09 |
| 6/1/00 | 41989 Visit 335 | 1 | 699 | 0 | 81811 | 63503 | 250 | 0.3056 | 0.3937 | | |
| 6/14/00 | 40846 Visit 330 | 3 | 559 | 0 | 98766 | 74485 | 3 | 0.0030 | 0.0040 | | |
| | mean | | | | 91784 | 64675.13 | 37.375 | 0.046018798 | 0.05990837 | 0.04 | 0.123333333 |
| | SD | | | | 38863.254 | 21074.95 | 85.97664 | 0.104985353 | 0.135000524 | 0.026457513 | 0.123423391 |
| | SN vs SP/Detect | | | | 0.2719675 | 0.294514 | 0.016718 | 0.084419635 | 0.06891274 | 0.414444189 | 0.984173536 |
| | SN vs SP/Undetect | | | | 0.0907158 | 0.042864 | 0.752949 | 0.934380608 | 0.9172846 | 0.445328944 | 0.815483198 |
| | SP/Detect vs SP/Undetect | | 0.479 | | 0.5857258 | 0.959285 | 0.390795 | 0.390488333 | 0.39541498 | 0.890843778 | 0.836166008 |
| | SN vs SP/All | | | | 0.1335716 | 0.118728 | 0.77884 | 0.434584864 | 0.40972451 | 0.343667848 | 0.870121379 |

Serostatus: 0=HIV-1 seronegative, 1=HIV-1 infected, 3=AIDS
> 0.02% NK-Tcells II lymphs considered positive

Figure 24

Percent of cells expressing both markers out of the *total* number of cells collected

| Run | | Control 6B11 FC | New Onset 6B11 FC | | VB11 PE | Control 6B11 FC | New Onset 6B11 FC | | Control VB11 PE | New Onset VB11 PE |
|---|---|---|---|---|---|---|---|---|---|---|
| 1 | VA24 PE | 0.02 | 0.07 | VB11 PE | | 0.03 | 0.08 | VA24 FC | 0.04 | 0.05 |
| 2 | | 0.10 | 0.17 | | | 0.13 | 0.28 | | 0.05 | 0.08 |
| 3 | | 0.05 | 0.17 | | | 0.00 | 0.23 | | 0.04 | 0.22 |
| 4 | | 0.06 | 0.33 | | | 0.03 | 0.32 | | 0.09 | 0.26 |
| 5 | | 0.03 | 0.03 | | | 0.02 | 0.00 | | 0.03 | 0.00 |
| 6 | | 0.06 | 0.23 | | | 0.08 | 0.21 | | 0.09 | 0.23 |
| 7 | | 0.06 | 0.09 | | | 0.08 | 0.14 | | 0.08 | 0.12 |
| | Avg. | 0.05 | 0.16 | | Avg. | 0.05 | 0.18 | Avg. | 0.06 | 0.14 |
| | Std. Dev. | 0.03 | 0.10 | | Std. Dev. | 0.05 | 0.11 | Std. Dev. | 0.03 | 0.10 |
| | | 0.03506137 | | | | 0.021871 | | | 0.088943 | |

Table 1: Percent of cells expressing both markers out of the *gated* population

| Run | | Control 6B11 FC | New Onset 6B11 FC | | VB11 PE | Control 6B11 FC | New Onset 6B11 FC | | Control VB11 PE | New Onset VB11 PE |
|---|---|---|---|---|---|---|---|---|---|---|
| 1 | VA24 PE | 0.02 | 0.08 | VB11 PE | | 0.03 | 0.09 | VA24 FC | 0.04 | 0.06 |
| 2 | | 0.11 | 0.17 | | | 0.14 | 0.30 | | 0.06 | 0.09 |
| 3 | | 0.06 | 0.19 | | | 0.00 | 0.25 | | 0.05 | 0.24 |
| 4 | | 0.07 | 0.34 | | | 0.03 | 0.33 | | 0.10 | 0.27 |
| 5 | | 0.05 | 0.04 | | | 0.04 | 0.00 | | 0.04 | 0.00 |
| 6 | | 0.07 | 0.29 | | | 0.10 | 0.27 | | 0.11 | 0.29 |
| 7 | | 0.07 | 0.12 | | | 0.09 | 0.17 | | 0.09 | 0.15 |
| | Avg. | 0.06 | 0.18 | | Avg. | 0.06 | 0.20 | Avg. | 0.07 | 0.16 |
| | Std. Dev. | 0.03 | 0.11 | | Std. Dev. | 0.05 | 0.12 | Std. Dev. | 0.03 | 0.11 |

Figure 25A

Genes differentially expressed between natural killer
T cell clones ME10 and GW4

| Functional category | Accession no. | Common name | Cluster (row, column) |
|---|---|---|---|
| Surface receptor | | | |
| | U38276 | Semaphorin III | (1,1) |
| | U82169 | Frizzled | (1,1) |
| | M32315 | TNF-R | (1,2) |
| | U03397 | 4-1BB | (1,2) |
| | S77812 | VEGF-R | (1,2) |
| | X01057 | IL-2Rα | (1,2) |
| | Y00285 | IGF-R II | (1,2) |
| | L08096 | CD27 | (1,2) |
| | Z30426 | CD69 | (1,2) |
| | U76764 | CD97 | (1,2) |
| | U60800 | CD100 | (1,2) |
| | M24283 | Rhinovirus-R | (1,2) |
| | U19906 | Arginine vasopressin-R | (1,2) |
| | Z48042 | p137 | (1,2) |
| | D79206 | Ryudocan | (1,3) |
| | HT3125 | CD44 | (1,3) |
| | L39064 | IL-9R | (2,1) |
| | X14046 | CD37 | (2,1) |
| | L31584 | EBI-1 | (2,1) |
| | X97267 | LPAP | (2,1) |
| | M33680 | TAPA-1 | (2,2) |
| | M63175 | AMFR | (2,2) |
| | U60975 | gp250 | (2,2) |
| | Z50022 | C21orf3 | (2,2) |
| | U90546 | Butyrophilin BT4 | (2,3) |
| | U90552 | Butyrophilin BT5 | (2,3) |
| | X96719 | AICL | (2,3) |
| Cytoskeleton | | | |
| | U80184 | Flightless I homolog | (1,1) |
| | X00351 | β-Actin | (1,2) |
| | U20582 | Actin-like peptide | (1,2) |
| | X82207 | β-Centractin | (1,2) |
| | X98534 | VASP | (1,2) |
| | D83735 | Calponin | (2,1) |
| | J00314 | β-Tubulin | (2,3) |
| | M21812 | Myosin LC | (2,3) |
| | X98411 | Myosin-IE | (2,3) |
| Kinase/phosphatase | | | |
| | X79510 | PTP D1 | (1,1) |
| | L10717 | ITK | (1,2) |
| | X60673 | AK3 | (1,2) |
| | X85545 | PKX-1 | (1,2) |
| | D13720 | LYK | (1,2) |
| | HT1153 | Nm23-H2S | (1,2) |
| | M30448 | CK II β | (1,2) |
| | M90299 | Glucokinase | (1,2) |
| | U08316 | ISPK-1 | (1,2) |
| | X80910 | PPP1CB | (1,2) |
| | X93920 | DUSP-6 | (1,2) |
| | U24152 | PAK-1 | (1,3) |
| | D11327 | PTPN7 | (1,3) |
| | U15932 | DUSP-5 | (1,3) |
| | L16862 | GRK-6 | (2,1) |
| | L27071 | TXK | (2,1) |
| | J03805 | PPP2CB | (2,2) |
| | HT3678 | CLK-1 | (2,3) |
| | U66464 | HPK-1 | (2,3) |
| | X62535 | DAG kinase | (2,3) |
| | M31724 | PTP-1B | (2,3) |
| Cytokine | | | |
| | U89922 | LT-β | (1,1) |
| | J00219 | IFN-γ | (1,2) |

| Functional category | Accession no. | Common name | Cluster (row, column) |
|---|---|---|---|
| | V00536 | IFN-γ | (1,2) |
| | M13207 | GM-CSF | (1,2) |
| | M16441 | TNF-α | (1,2) |
| | X02910 | TNF-α | (1,2) |
| | X04688 | IL-5 | (1,2) |
| | U31120 | IL-13 | (1,2) |
| | M37435 | M-CSF | (1,2) |
| | U02020 | PBEF | (1,2) |
| | U37518 | TRAIL | (1,2) |
| | U46461 | Dishevelled homolog | (1,2) |
| | M90391 | IL-16 | (2,3) |
| Nuclear protein | | | |
| | U73477 | Nuclear pp32 | (1,1) |
| | U62962 | Int-6 | (1,2) |
| | L25931 | Lamin B receptor | (1,3) |
| | M17733 | Thymosin-β4 | (2,3) |
| Transcription factor | | | |
| | M69043 | IκBα | (1,2) |
| | X58072 | GATA-3 | (1,2) |
| | U43185 | STAT-5A | (1,2) |
| | X51345 | Jun-B | (1,2) |
| | X56681 | Jun-D | (1,2) |
| | U15460 | B-ATF | (1,2) |
| | HT4899 | C-myc | (1,2) |
| | L00058 | C-myc | (1,2) |
| | M13929 | C-myc | (1,2) |
| | U26173 | NF-IL3A | (1,2) |
| | M97796 | Id-2 | (1,2) |
| | M96843 | Id-2B | (1,2) |
| | D14826 | CREM | (1,2) |
| | S68271 | CREM | (1,2) |
| | J03827 | Y box BP | (1,2) |
| | U09412 | ZNF134 | (1,2) |
| | U13044 | NRF-2α | (1,2) |
| | U22431 | HIF-1α | (1,2) |
| | X78925 | HZF-2 | (1,2) |
| | Z47727 | RNA POL2K | (1,2) |
| | J04076 | EGR-2 | (1,3) |
| | D61380 | DJ-1 | (1,3) |
| | HT4567 | PC4 | (1,3) |
| | HT4921 | BTF-3 homolog | (2,1) |
| | L41067 | NFAT-4C | (2,3) |
| | L78440 | STAT-4 | (2,3) |
| | M82882 | ELF-1 | (2,3) |
| | M83667 | NF-IL6 | (2,3) |
| Signal transduction | | | |
| | HT5108 | TRAP-3 | (1,1) |
| | X80200 | MLN62 | (1,1) |
| | U20158 | SLP-76 | (1,2) |
| | U26710 | Cbl-b | (1,2) |
| | D78132 | RHEB | (1,2) |
| | M63573 | SCYLP | (1,2) |
| | M75099 | FK506 BP | (1,2) |
| | Z35227 | TTF | (1,2) |
| | U19261 | EBV-independent | (1,3) |
| | M28209 | RAB-1 | (2,2) |
| | D78577 | 14-3-3-Eta | (2,3) |
| | X89399 | Ins(1345)P4 BP | (2,3) |
| RNA Metabolism | | | |
| | D38251 | RNP B5 | (1,1) |
| | U90547 | RNP homolog | (1,1) |
| | X17567 | RNP B | (1,2) |
| | M29064 | RNP B1 | (1,2) |

Figure 25A Continued

| Functional category | Accession no. | Common name | Cluster (row, column) |
|---|---|---|---|
| | HT110 | RNP A/B | (1,2) |
| | Z23064 | RNP G | (1,2) |
| | HT3238 | RNP K | (1,2) |
| | X52979 | RNP SmB | (1,2) |
| | U15009 | RNP SmD3 | (1,2) |
| | X85372 | RNP Sm F | (1,2) |
| | U30827 | SF SRp40 | (1,2) |
| | X70944 | SF (PTP-associated) | (1,2) |
| | M60858 | Nucleolin | (1,2) |
| | U10323 | NF45 | (1,2) |
| | U38846 | Stimulator of TAR | (1,2) |
| | X59417 | PROS-27 | (1,2) |
| | X59892 | IFN-independent γ2 | (1,2) |
| | X66899 | EWS | (1,2) |
| | X71428 | fus | (1,2) |
| | X72727 | Tunp | (1,2) |
| | X75755 | PR264 | (1,2) |
| | Z24724 | Poly A site | (1,2) |
| | L28010 | RNP F | (1,3) |
| | HT4788 | RNP I | (1,3) |
| | L03532 | M4 | (1,3) |
| | U69546 | RNA BP | (2,3) |
| Apoptosis | | | |
| | Z23115 | Bcl-X$_L$ | (1,2) |
| | U45878 | IAP-1 | (1,2) |
| | U11821 | Fas ligand | (1,2) |
| | S81914 | IEX-1 | (1,2) |
| | U37546 | MIHC | (1,2) |
| Chemokine | | | |
| | M23178 | MIP-1α | (1,2) |
| | J04130 | MIP-1β | (1,2) |
| | M69203 | MCP-1 | (1,2) |
| | L19686 | MIF | (1,3) |
| Protein metabolism | | | |
| | D28473 | ILE-tRNA synthase | (1,2) |
| | U09510 | GLY-tRNA synthase | (1,2) |
| | L25085 | Sec61-β | (1,2) |
| | X74801 | Chaperonin cctg | (1,2) |
| | X77584 | Thioredoxin | (1,2) |
| | Y00281 | Ribophorin I | (1,2) |
| | Y10807 | ARG-methyltransferase | (1,3) |
| | D13748 | EIF-4AI | (1,3) |
| | X55733 | EIF-4B | (2,1) |
| | X76648 | Glutaredoxin | (2,3) |

Genes populating the six expression clusters for the 11 gene functional categories shown in Fig. 2 are listed. Each gene is identified by GenBank accession no. (or The Institute for Genomic Research (TIGR) identifier for HT designations), followed by a common name and the specific cluster into which it fell (row, column).

26 C.

26 D.

COMPOSITIONS AND METHODS OF MONOCLONAL AND POLYCLONAL ANTIBODIES SPECIFIC FOR T CELL SUBPOPULATIONS

CROSS-REFERENCE TO RELATED APPLICATIONS

This application is a continuation of U.S. application Ser. No. 09/885,768, filed Jun. 19, 2001, which, in turn, claims benefit of U.S. Provisional Application No. 60/212,466, filed Jun. 19, 2000. U.S. application Ser. No. 09/885,768 is hereby incorporated by reference.

STATEMENT AS TO FEDERALLY SPONSORED RESEARCH

This invention was funded by grant AI42955 from the National Institutes of Health. The government may have certain rights in the invention.

BACKGROUND OF THE INVENTION

Modulation of the immune system is desirable to treat a variety of diseases and disorders including, but not limited to, autoimmune diseases, infections, allergies, asthma, inflammatory conditions, spontaneous abortion, pregnancy, graft versus host disease, and cancers.

T cells are lymphocytes that participate in multiple cell-mediated immune reactions, such as the recognition and destruction of infected or cancerous cells. Subsets of T cells, such as suppressor, cytotoxic, and helper T cells, mediate different immunologic functions. Suppressor T cells are responsible for turning the immune response off after an infection is cleared. Cytotoxic or "natural killer" T cells destroy infected or cancerous cells. Helper T cells produce cytokines that modulate the activity of cytotoxic T cells and/or antibody-producing B cells.

A subset of helper T cells, Th1 cells, secrete interleukin-1 (IL-1), IL-2, gamma interferon (INF-$\gamma$), and IL-2 which enhance cell-mediated responses such as cytotoxic T cell activity and inhibit both Th2 helper T cell activity and humoral immunity mediated by soluble antibodies. Due to their ability to kill antigen-presenting cells and their cytokine-mediated effector activity, Th1 cells are associated with vigorous delayed-type hypersensitivity reactions. Th2 cells, the other subset of helper T cells, are thought to inhibit cell-mediated responses and to enhance the humoral response. Th2 cells secrete IL-4, IL-5, IL-6, IL-9, IL-10, and IL-13 which activate B cell development and antibody production. T cells may also participate in immune deviation responses, such as the suppression of an ongoing immune response which may involve the secretion of TGF-$\beta$ or IL-10 cytokines (Sonoda et al, J. Ex. Med. 190:1215-1255, 1999; Streilein et al., Hum. Immunol. 52:138-143, 1997; Hong et al, J. Ex. Med. 190, 1197-1200, 1999; Streilein et al., J. Immunol. 158:3557-3560, 1997).

To recognize a particular antigen bound to an antigen-presenting cell, most T cells express a highly specific T cell receptor (TCR) on their cell surface. The chains of the most common T cell receptors are called $\alpha$ and $\beta$. A second T cell receptor, found on a minor subpopulation of T cells, is composed of $\gamma$ and $\delta$ chains. The genes for the $\alpha$, $\beta$, $\gamma$, and $\delta$ chains of the T cell receptors have organizations similar to that of antibody genes: there are libraries of V, D, and J regions from which members are joined to form entire genes.

In contrast to most T cell subpopulations, which have diverse sequences for their TCR-$\alpha$ chain, invariant T cells have a highly conserved invariant TCR-$\alpha$ chain, V$\alpha$24-J$\alpha$Q in humans and V$\alpha$14-J$\alpha$281 in mice, that pairs preferentially with human V$\beta$11 or murine V$\beta$8. These cells are either CD4$^+$CD8$^-$ or CD4$^-$CD8$^-$. This invariant TCR is presumed to enable invariant T cells to recognize endogenous or pathogen-derived lipid antigens presented by nonpolymorphic MHC class I-like proteins, called CD1 family members. Humans have four CD1 proteins (CD1a, CD1b, CD1c, and CD1d), but mice have only a duplicated CD1d gene that is highly homologous to human CD1d. Human CD1d is expressed at high levels by thymocytes, at lower levels by B cells and monocytes, and by some cells outside of the lymphoid and myeloid lineages.

Many invariant T cells are distinguished by expression of several cell surface proteins otherwise found largely on natural killer (NK) cells, including CD161 (NKR-P1A) in humans, and a cell surface C-type lectin, NKR-P1C (NK1), in mice. This T cell subpopulation, referred to here as "invariant NK T cells," represents a major fraction of the mature T cells in thymus, the major T cell subpopulation in murine liver, and up to 5% of splenic T cells in some mouse strains.

Murine and human invariant T cells produce large amounts of the immunoregulatory cytokines IL-4 (a Th2 effector) and IFN-$\gamma$ (a Th1 effector) in vivo in response to an anti-CD3 antibody or CD1d. These cytokines allow the cells to participate in both Th2 and Th1 responses. The role of invariant T cells in augmenting the Th2 response, which appears to be protective in some autoimmune diseases, is further supported by the presence of defects in invariant T cells in a number of human and murine models of autoimmune diseases, including type 1 diabetes. Thus, alterations in the balance between Th1 and Th2 responses induced by invariant T cells may play a role in the development of autoimmune diseases.

Invariant T cells can also promote rapid Th1 immune responses and anti-tumor responses. Invariant T cells, which comprise a major fraction of the T cells in murine liver, can be stimulated by IL-12 to become active cytotoxic T cells and protect against liver metastases in tumor models. This conclusion was confirmed genetically through the generation of J$\alpha$281 knockout mice, which do not express the invariant V$\alpha$14-J$\alpha$281 TCR. These mice had markedly diminished numbers of invariant T cells and could not mediate IL-12 induced tumor rejection. Other studies showed that IL-12 administration no longer induced an early IFN-$\gamma$ response in the spleen and liver of CD1d knockout mice, which are invariant T cell deficient. In addition, data from human patients shows fewer invariant NK T cells and reduced Th1-like responses in patients with advanced cancer. The anti-tumor response of activated invariant T cells could be partially mediated by their CD1d specific cytotoxicity and NK/LAK cell-like toxicity. Other regulatory functions of invariant T cells, possibly through cytokine production or interactions with antigen presenting cells (APCs), may also play important roles in anti-tumor immune responses.

Invariant T cells may also have a role in the pathogenesis of spontaneous abortion. Stimulation of decidual invariant T cells in mice by administration of a ligand for invariant T cells provoked abortion in pregnant mice. The perforin-dependent killing and production of IFN-$\gamma$ and tumor necrosis factor-$\alpha$ by the invariant T cells were required for this induction of abortion.

In contrast to human peripheral blood in which invariant T cells are the major CD1d-reactive subpopulation, human and mouse bone marrow and human liver have T cell populations dominated by CD1d-reactive noninvariant T cells using diverse TCRs which can also produce a large amount of IL-4 and IFN-γ. These CD1d-reactive noninvariant T cells can be either NK or non-NK T cells, and they function similarly to CD1d-reactive invariant T cells. The CD1d-reactive noninvariant T cells in bone marrow may have a role in suppressing graft versus host disease, and both populations may enhance graft versus leukemia responses. In the liver, these T cells may protect against infections, such as Hepatitis C infections, but may also cause damage due to their Th1 response. Additionally, we found that CD1d-reactive NK T cells are critical for immune tolerance to antigens in the anterior chamber of the eye, an immune privileged site (Sonoda et al., supra). Such mechanisms may also be important in the maintenance of peripheral tolerance.

Parasitic glycosyl-phosphatidylinositols derived from *Plasmodium, Trypanosoma,* or *Leishmania* have been recently shown to stimulate murine CD1d-reactive invariant Vα14 NK T cells. In addition, an α-galactosylceramide (α-GalCer) lipid, which was isolated from marine sponge in a screen for anti-tumor activity, is a CD1d-presented antigen. α-GalCer is an example of an agent which can be used to expand human CD1d-reactive invariant T cells from umbilical cord or peripheral blood samples that are first enriched for invariant T cells by purification using an anti-Vα24 antibody. The enriched Vα24$^+$ cells are cocultured in the presence of α-GalCer and purified antigen-presenting cells (APCs). However, it would be desirable in a clinical setting to use a improved method of expanding invariant T cells that does not require a two step complex protocol or the presence of antigen-presenting cells, which may be not work under certain conditions.

There exists a need to specifically monitor and alter the population of T cells and, more specifically, specific subpopulations of T cells in mammals for the prevention and treatment of diseases and disorders such as autoimmune diseases, infections, allergies, asthma, inflammatory conditions, spontaneous abortion, pregnancy, graft versus host disease, and cancers.

SUMMARY OF THE INVENTION

We have discovered and reduced to practice a method for making antibodies which allow the selective identification and expansion or activation of specific T cell subgroups. In particular, the invention features antibodies which recognize and expand T cells having specific TCR sequences. These antibodies may be used for diagnosing, preventing, stabilizing, and treating a variety of diseases including cancers and autoimmune diseases.

Accordingly, in one aspect, the invention features a purified antibody that preferentially binds a T cell antigen receptor (TCR). This antibody preferentially binds a CDR3-loop or an α-β junction of the TCR; or preferentially binds or modulates (e.g., increases or decreases) the expansion or activation of at least one T cell subpopulation selected from the group of NK T cells, CD1d-reactive T cells, and JαQ$^+$ T cells. In a related aspect, the invention features a combination of purified antibodies (e.g., a mixture of 2, 3, 4, or 5 antibodies) that together preferentially bind a T cell antigen receptor (TCR). In combination, these antibodies preferentially bind a CDR3-loop or an α-β junction of the TCR; or preferentially modulate the expansion or activation of at least one T cell subpopulation selected from the group of NK T cells, CD1d-reactive T cells, and JαQ$^+$ T cells. A desirable antibody combination include a mixture of one of the following pairs of antibodies: (i) an anti-Vα24 antibody and an anti-CD161 antibody; (ii) an anti-Vα24 antibody and an anti-CD94 antibody; (iii) an anti-Vβ11 antibody and an anti-CD161 antibody; or (iv) an anti-Vβ11 antibody and an anti-CD94 antibody. Desirably, these antibody combinations preferentially bind or preferentially modulate the expansion or activation of CD1d-reactive T cells.

In desirable embodiments, the antibody or antibody combination preferentially binds an invariant T cell. In another desirable embodiment, NK T cells that are bound by the antibody or antibody combination are CD1d-reactive T cells, invariant T cells, CD1d-reactive noninvariant T cells, or JαQ$^+$ T cells. In yet other desirable embodiments, the antibody or antibody combination preferentially binds the antigen binding site of a TCR. Desirably, the NK T cells, CD1d-reactive T cells, or JαQ$^+$ T cells are invariant T cells. Desirably, the CDR3-loop, α-β junction, or antigen binding site of a TCR is expressed on a NK T cell, CD1d-reactive T cell, or JαQ$^+$ T cell. In still other desirable embodiments, the antibody or antibody combination preferentially binds a CDR3-loop, an antigen binding site, or an α-β junction of a TCR expressed on a NK T cell, CD1d-reactive T cell, or JαQ$^+$ T cell, and the antibody or antibody combination preferentially modulates the expansion or activation of the bound T cell. Desirably, a T cell expressing a TCR that is bound by the antibody or antibody combination is expanded in the presence of the antibody. In another desirable embodiment, the binding of the CDR3-loop, α-β junction, or antigen binding site of a TCR expressed on a T cell is sufficient to quantify the T cells, the CDR3-loops, α-β junctions, or the antigen binding sites. In desirable embodiments, a second antibody is used to distinguish different T cell subpopulations bound by the antibody of the invention. In one embodiment, the antibody is a bifunctional antibody. In one embodiment, the antibody is a polyclonal or monoclonal antibody. In a desirable embodiment, the antibody is covalently linked to a toxin, therapeutically active compound, enzyme, cytokine, radiolabel, fluorescent label, magnetic label, or affinity tag. Desirable antibodies have a constant region found in a mammal other than the mouse, such as a human. Desirably, the antibody is humanized.

In a related aspect, the invention provides a fragment or derivative of an antibody, wherein the antibody preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. Desirable fragments include ScFv, Fab, and F(ab')$_2$ fragments.

In another aspect, the invention provides a bifunctional antibody including (a) an antibody of the invention or a fragment of the antibody, and (b) a second antibody or fragment of an antibody that binds a T cell expressing the TCR or that binds a NK T cell, CD1d-reactive T cell, or JαQ$^+$ T cell that is bound by the antibody or fragment of the invention. Desirably, the second antibody is also an antibody of the invention. In another embodiment, the second antibody is an anti-CD3, anti-CD161, anti-CD28, or anti-CD94 antibody. In a related aspect, the invention features a bifunctional antibody that preferentially binds a CDR3-loop or an α-β junction of the TCR; or preferentially binds or modulates the expansion or activation of at least one T cell subpopulation selected from the group of NK T cells, CD1d-reactive T cells, and JαQ$^+$ T cells. In various embodiments of these aspects, the antibody is a bifunctional anti-CD3 and anti-CD161 antibody, anti-Vα24 and anti-CD161 antibody; anti-Vα24 and anti-CD94 antibody; anti-Vβ11 and anti-CD161 antibody; anti-Vβ11 and anti-CD94 antibody; anti-CD3 and anti-CD94 antibody, anti-CD3 and anti-CD28; or anti-Vα24 and anti-Vβ11 antibody.

In particular embodiments, the bifunctional antibody preferentially binds, expands, or activates CD1d-reactive T cells.

In yet another aspect, the invention provides a stable hybridoma that produces an antibody of the invention.

The antibodies of the invention may be used to purify T cell subpopulations. Thus, the invention also features a purified T cell subpopulation. The T cells in the subpopulation are specifically bound by an antibody or antibody combination of the invention. Desirably, the antibody or antibody combination specifically binds the CDR3-loop, α-β junction, or the antigen binding site of a TCR expressed on the subpopulation of T cells. In a desirable embodiment, the T cells in the subpopulation are NK T cells. Desirable NK T cells include CD1d-reactive T cells, invariant T cells, CD1d-reactive noninvariant T cells, and JαQ$^+$ T cells. In another desirable embodiment, the T cells are CD1d-reactive T cells. In yet another desirable embodiment, the T cells are JαQ$^+$ T cells. Desirably, the NK T cells, CD1d-reactive T cells, or JαQ$^+$ T cells are invariant T cells.

The invention also provides methods for generating an antibody of the invention that preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. One such method includes (a) coupling a cyclic peptide to a carrier, (b) immunizing an animal with the coupled peptide, and (c) isolating an antibody that preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. Desirably, step (b) is repeated. In other desirable embodiments, the animal is a CD1 or invariant T cell deficient mammal or bird.

In a related aspect, the invention provides another method of generating an antibody of the invention. This method includes (a) immunizing an animal (e.g., a mammal or a bird) with NK T cells, CD1d-reactive T cells, or JαQ$^+$ T cells, and (b) isolating an antibody that preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. Desirably, step (a) is repeated. In one desirable embodiment, invariant T cells are administered to a CD1 or invariant T cell deficient animal.

In another related aspect, the invention features a method of generating an antibody of the invention. This method involves (a) coupling a cyclic peptide to a carrier, (b) immunizing an animal (e.g., a mammal or a bird) with the coupled peptide, (c) immunizing the animal with NK T cells, CD1d-reactive T cells, or JαQ$^+$ T cells, and (d) isolating an antibody that preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. Desirably, step (b) or (c) is repeated. In one desirable embodiment, invariant T cells are administered to a CD1 or invariant T cell deficient animal.

In still another related aspect, the invention provides a method of generating an antibody of the invention by (a) immunizing an animal (e.g., a mammal or a bird) with NK T cells, CD1d-reactive T cells, or JαQ$^+$ T cells, (b) coupling a cyclic peptide to a carrier, and (c) immunizing the animal with the coupled peptide, and (d) isolating an antibody that preferentially binds a CDR3-loop or an α-β junction of a TCR; or preferentially binds or modulates the expansion or activation of at least one T cell subpopulation selected from the group of NK T cells, CD1d-reactive T cells, and JαQ$^+$ T cells. Desirably, step (a) or step (c) is repeated. In one desirable embodiment, invariant T cells are administered to a CD1 or invariant T cell deficient animal.

In desirable embodiments of the methods of generating an antibody, the animal (e.g., mammal or bird) is a CD1 or invariant T cell deficient animal, a CD1d knockout mouse, an animal in which invariant T cells have been removed, an animal lacking part of the TCR-α chain, or an animal lacking part of the TCR-β chain. In other desirable embodiments, the animal is tolerized to NK T cells, CD1d-reactive T cells, JαQ$^+$ T cells, invariant T cells, or the invariant TCR. In other desirable embodiments, the animal lacks all or part of the Vα14 or Jα281 molecule. It is also contemplated that another animal with a reduced amount or lacking NK T cells, CD1d-reactive T cells, or JαQ$^+$ T cells may be used.

The antibodies, bifunctional antibodies, fragments of antibodies, and derivatives of antibodies of the present invention have a variety of diagnostic, imaging, and therapeutic applications.

In one such aspect, the invention provides a method of measuring the amount of NK TCRs or the amount of NK T cells in a sample by contacting the sample with an antibody or antibody combination of the invention. Desirably, the antibody or antibody combination preferentially binds a CDR3-loop, an antigen binding site, or an α-β junction of the TCRs. In another embodiment, the antibody is a bifunctional antibody that binds both CD3 and CD161 expressed on the same T cell.

In a related aspect, the invention features a method of measuring the amount of CD1d-reactive TCRs or the amount of CD1d-reactive T cells in a sample. This method involves contacting the sample with an antibody or antibody combination of the invention. Desirably, the antibody or antibody combination preferentially binds a CDR3-loop, an α-β junction, or an antigen binding site of the TCRs. In various embodiments, the antibody is a bifunctional anti-Vα24 and anti-CD161 antibody; anti-Vα24 and anti-CD94 antibody; anti-Vβ11 and anti-CD161 antibody; anti-Vβ11 and anti-CD94 antibody; anti-CD3 and anti-CD94 antibody, anti-CD3 and anti-CD28; or anti-Vα24 and anti-Vβ11 antibody.

In another related aspect, the invention features a method of measuring the amount of JαQ$^+$ TCRs or the amount of JαQ$^+$ T cells in a sample by contacting the sample with an antibody or antibody combination of the invention. In one desirable embodiment, the antibody preferentially binds a CDR3-loop, an antigen binding site, or an α-β junction of the TCRs.

In desirable methods of measuring the amount of NK T cells, CD1d-reactive T cells, or JαQ$^+$ T cells in a sample, the sample is from a subject involved in a clinical trial of a therapy or undergoing a therapy for a condition selected from the group consisting of autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. Desirably, the amount of the TCRs or the T cells is used to determine the desirable therapy for the treatment or prevention of a condition selected from the group consisting of autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. In another desirable embodiment of these aspects, the amount of the TCRs or the T cells is used to diagnose the recovery or remission from or the efficacy of any therapy for a condition selected from the group consisting of autoimmune disease, viral infection, bacterial infection, parasitic infection, infection by a eukaryotic pathogen, allergy, asthma, inflammatory condition, graft versus host disease, graft rejection, immunodeficiency disease, pregnancy, and cancer.

In another aspect, the invention provides a method of visualizing the NK TCRs or the NK T cells in a sample, the method comprising contacting the sample with an antibody or antibody combination of the invention. Desirably, the antibody or antibody combination preferentially binds a CDR3-loop, an antigen binding site, or an α-β junction of the TCRs. In another embodiment, the antibody is a bifunctional antibody that binds both CD3 and CD161 expressed on the same T cell.

In a related aspect, the invention features a method of visualizing the CD1 d-reactive TCRs or the CD1d-reactive T cells in a sample by contacting the sample with an antibody or antibody combination of the invention. In one desirable embodiment, the antibody or antibody combination preferentially binds a CDR3-loop, an antigen binding site, or an α-β junction of the TCRs. Desirably, the antibody or antibody combination preferentially binds a CDR3-loop, an α-β junction, or an antigen binding site of the TCRs. In various embodiments, the antibody is a bifunctional anti-Vα24 and anti-CD161 antibody; anti-Vα24 and anti-CD94 antibody; anti-Vβ11 and anti-CD161 antibody; anti-Vβ11 and anti-CD94 antibody; anti-CD3 and anti-CD94 antibody, anti-CD3 and anti-CD28; or anti-Vα24 and anti-Vβ11 antibody.

In another related aspect, the invention provides a method of visualizing the JαQ⁺ TCRs or the JαQ⁺ T cells in a sample. This method includes contacting the sample with an antibody or antibody combination of the invention. Desirably, the antibody or antibody combination preferentially binds a CDR3-loop, an antigen binding site, or an α-β junction of the TCRs.

In desirable embodiments of measuring or visualizing NK T cells, CD1d-reactive T cells, or JαQ⁺ T cells in a sample, the sample is from a transgenic animal or is an autopsy tissue. Desirably, the antibody is covalently bound to a fluorescent label, radiolabel, or magnetic label (e.g., a magnetic bead).

In another aspect, the invention provides a method of identifying a subject at risk for a condition selected from the group consisting of autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. This method includes (a) quantitating the amount of a subpopulation of T cells in a sample from the subject, and (b) comparing the amount of the T cells in the sample to the amount of the T cells found in subjects diagnosed with the condition or subjects not diagnosed with the condition. Desirably, the amount of the T cells in the sample is compared to the amount of the T cells found in both subjects diagnosed with the condition and subjects not diagnosed with the condition. In one desirable embodiment, the method further includes comparing the amount of another T cell type in the sample with the amount of the another T cell type found in subjects diagnosed with the condition or subjects not diagnosed with the condition. Desirably, the amount of the another T cell type in the sample is compared to the amount of the another T cell type found in both subjects diagnosed with the condition and subjects not diagnosed with the condition. In various embodiments, the amount of the subpopulation of T cells in a sample is determined by contacting the sample with an antibody or antibody combination of the invention, such as an antibody or antibody combination that preferentially binds a CDR3-loop, an antigen binding site, or an α-β junction of the T cells; or that preferentially binds NK T cells, CD1d-reactive T cells, or JαQ⁺ T cells.

In a related aspect, the invention provides a method of diagnosing or staging a subject with a condition selected from the group consisting of autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. This method includes (a) quantitating the amount of a subpopulation of T cells in a sample from the subject, and (b) comparing the amount of the T cells in the sample to the amount of the T cells found in subjects diagnosed with the condition or subjects not diagnosed with the condition. Desirably, the amount of the T cells in the sample is compared to the amount of the T cells found in both subjects diagnosed with the condition and subjects not diagnosed with the condition. In one desirable embodiment, the method further includes comparing the amount of another T cell type in the sample with the amount of the other T cell type found in subjects diagnosed with the condition or subjects not diagnosed with the condition. Desirably, the amount of the other T cell type in the sample is compared to the amount of the other T cell type found in both subjects diagnosed with the condition and subjects not diagnosed with the condition. In various embodiments, the amount of the subpopulation of T cells in a sample is determined by contacting the sample with an antibody or antibody combination of the invention, such as an antibody or antibody combination that preferentially binds a CDR3-loop, an antigen binding site, or an α-β junction of the T cells; or that preferentially binds NK T cells, CD1d-reactive T cells, or JαQ⁺ T cells.

In desirable embodiments of any of the above aspects, the sample is peripheral blood, lymphatic fluid, ascitic fluid, umbilical cord blood, urine, fecal matter, bone marrow, bile, or a biopsy sample. It is also contemplated that any other sample from a mammal may be used, such as other blood or tissue samples.

In another aspect, the invention features a method of treating or preventing an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer in an animal. This method includes administering to the animal an antibody or antibody combination of the invention. Desirably, the antibody or antibody combination is administered to the animal intraarticularly, intralesionally, orally, intramuscularly, intravenously, subcutaneously, or intraperitoneally. In another desirable embodiment, the antibody or antibody combination is administered with a pharmaceutically suitable carrier. In one desirable embodiment, a cytokine is also administered to the animal. In another desirable embodiment, a cell type or other agent which works in concert with the antibodies is also administered to the animal.

In yet another aspect, the invention provides a method of inhibiting T cell pathogenesis in an animal by administering to the animal an antibody or antibody combination of the invention. The administration of the antibody or antibody combination is sufficient to inhibit a T cell expressing a TCR bound by the antibody or antibody combination, a NK T cell, a CD1d-reactive T cell, or a JαQ⁺ T cell. Desirably, the antibody or antibody combination preferentially binds a CDR3-loop, an antigen binding site, or an α-β junction of a TCR of a NK T cell, a CD1d-reactive T cell, or a JαQ⁺ T cell. In another desirable embodiment, the antibody or antibody combination inhibits the expansion or activation of at least one T cell subpopulation selected from the group of NK T cells, CD1d-reactive T cells, and JαQ⁺ T cells. In another desirable embodiment, the antibody or antibody combination is covalently linked to a toxin, a radiolabel, or a molecule which targets host defensive or catabolic processes toward the cells. Desirably, the antibody or antibody combination is administered to the animal orally, intramuscularly, intravenously, intraarticularly, intralesionally, subcutaneously, intraperitoneally, intralesionally, or by any other route sufficient to provide a dose adequate to inhibit the T cell. In another desirable embodiment, the antibody or antibody combination is administered with a pharmaceutically suitable carrier. In one desirable embodiment, one or more cytokines are also administered to the animal. In another embodiment, the T cell pathogenesis is a response of a T cell to a viral infection, such as a Hepatitis infection, picornarirus infection, polio infection, or coxsacchie infection.

In another aspect, the invention provides a method of increasing the size of a subpopulation of T cells by contacting a sample having T cells with an antibody or antibody combination of the invention.

In a related aspect, the invention features a method of increasing the size of a subpopulation of T cells. This method includes (a) contacting a sample comprising the T cells with an antibody or antibody combination of the invention under conditions that allow complex formation between the T cells and the antibody or antibody combination, (b) isolating the complex, and (c) contacting the T cells in the complex or recovered from the complex with an antibody or antibody combination of the invention under conditions that allow the contacting to increase the number of the T cells.

In another aspect, the invention provides a method of increasing the size of a subpopulation of T cells. This method includes (a) contacting a sample comprising the T cells with an antibody or antibody combination of the invention under conditions that allow complex formation between the T cells and the antibody or antibody combination, (b) isolating the complex, and (c) contacting the T cells in the complex or recovered from the complex with an antigen and antigen presenting cells under conditions that allow the contacting to increase the number of the T cells. Desirably, the antigen is α-galactosylceramide, a lipid or glycosyl-phosphatidylinositol antigen from an infectious pathogen, an antigen from a cancerous cell, a self-lipid, or any other antigen from endogenous or non-physiological sources.

In yet another aspect, the invention features a method of increasing the size of a subpopulation of T cells. This method includes (a) purifying the T cells from a sample comprising the T cells and (b) contacting the purified cells with an antibody or antibody combination of the invention under conditions that allow the contacting to increase the number of the T cells.

In desirable embodiments of the methods of increasing the size of a subpopulation of T cells, the method further includes contacting the sample or the complex with one or more cytokines or other cells that work in concert with the antibody or antibody combination.

In another aspect, the invention provides a method of increasing the size of a subpopulation of T cells in an animal. This method includes (a) obtaining a sample comprising the T cells from the animal, (b) contacting the T cells with an antibody or antibody combination of the invention under conditions that allow the contacting to increase the number of the T cells, and (c) administering the contacted T cells to the animal.

In a related aspect, the invention provides a method of increasing the size of a subpopulation of T cells in an animal. This method includes (a) obtaining a sample comprising the T cells from the animal, (b) purifying the T cells, (c) contacting the T cells with an antibody or antibody combination of the invention under conditions that allow the contacting to increase the number the T cells, and (d) administering the contacted T cells to the animal. Desirably, the purification of the T cells includes contacting the sample with an antibody or antibody combination of the invention. In a desirable embodiment, the purification of the T cells includes contacting the sample with an anti-Vα24, CD4, CD8, CD56, CD161, or Vβ11 antibody. It is also contemplated that another antibody or combination of antibodies that binds a T cell may be used to purify the cells.

In yet another aspect, the invention provides a method of increasing the size of a subpopulation of T cells in an animal. This method includes (a) obtaining a sample comprising the T cells from the animal, (b) contacting the T cells with an antibody or antibody combination of the invention under conditions that allow complex formation between the T cells and the antibody, (c) isolating the complex, and (d) contacting the T cells in the complex or recovered from the complex with an antibody or antibody combination of the invention under conditions that allow the contacting to increase the number of the T cells, and (e) administering the contacted T cells to the animal.

In still another aspect, the invention features a method of increasing the size of a subpopulation of T cells in an animal. This method includes (a) obtaining a sample comprising the T cells from the animal, (b) contacting the T cells with an antibody or antibody combination of the invention under conditions that allow complex formation between the T cells and the antibody or antibody combination, (c) isolating the complex, and (d) contacting the T cells in the complex or recovered from the complex with an antigen and antigen presenting cells under conditions that allow the contacting to increase the number of the T cells, and (e) administering the contacted T cells to the animal. Desirably, the antigen is α-galactosylceramide, a lipid or glycosyl-phosphatidylinositol antigen from an infectious pathogen, an antigen from a cancerous cell, a self-lipid, or any other antigen from endogenous or non-physiological sources.

In desirable embodiments of the methods for increasing the size of a subpopulation of T cells in an animal, the methods also include administering one or more cytokines to the animal. Desirably, the cytokine is administered to the animal before, during, or after the contacted T cells are administered to the animal. In desirable embodiments, the cytokine is administered intramuscularly, intravenously, intraarticularly, intralesionally, subcutaneously, or by any other route sufficient to provide a dose adequate to modulate the activity of a T cell. Desirably, the sample or the T cells are contacted with one or more cytokines. Desirably, the methods of these aspects are used in the treatment or prevention of an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer in the animal.

In another aspect, the invention provides a method of purifying a subpopulation of T cells from a sample by contacting the sample with an antibody or antibody combination of the invention.

In a related aspect, the invention provides a method of purifying a subpopulation of T cells from a sample. This method includes (a) contacting the sample with an antibody or antibody combination of the invention under conditions that allow complex formation between the T cells and the antibody, and (b) isolating the complex. Desirably, the sample is also contacted with an anti-Vα24, CD4, CD8, CD56, CD161, or Vβ11 antibody. In another embodiment, the sample is contacted with any other antibody that binds a related T cell subset. Desirably, the method also includes recovering the T cells from the complex. In one desirable embodiment, the antibody is covalently linked to a fluorescent label, and the complex is isolated based on the fluorescence signal of the complex. In another desirable embodiment, the antibody is covalently linked to a magnetic label, and the complex is isolated based on the magnetism of the complex.

In desirable embodiments of every aspect of the invention, the cytokine that is contacted with the sample, T cells, or complex or the cytokine that is administered to the animal is selected from the group consisting of IL-2, IL-4, IL-7, IL-10, IL-12, IL-13, IL-15, IL-18, IFN-α/β, IFN-γ, and GM-CSF. It is also contemplated that any other cytokine or combination of cytokines may be used. Desirably, the cytokine alters the ratio of Th1/Th2/immune deviation response by the contacted T cells. Desirably, the subject or the animal is a human. Other desirable animals include mammals and birds of laboratory or veterinary interest such as mice, rats, rabbits, pigs, goats, cattle, sheep, horses, chickens, and turkeys. In desirable embodiments, the viral infection relevant to the methods of the invention is a Hepatitis infection, picornarirus infection, polio infection, HIV infection, or coxsacchie infection. In other embodiments, the autoimmune disease is type 1 diabetes.

In desirable embodiments of each method of the invention, the antibody or antibody combination preferentially binds an invariant T cell. Desirably, the T cell subpopulation, T cells, or T cell expressing the TCR are NK T cells, CD1d-reactive T cells, or JαQ⁺ T cells. Desirable NK T cells are CD1d-reactive T cells, invariant T cells, CD1d-reactive noninvariant T cells, or JαQ⁺ T cells. Desirable CD1d-reactive T cells or JαQ⁺ T cells are invariant T cells. Desirable JαQ⁺ T cells are Vα24⁺JαQ⁺ T cells. Desirably, the antibody or antibody combination preferentially binds a CDR3-loop, an antigen binding site, or an α-β junction of a TCR expressed on the T cell and preferentially binds or modulates the expansion or activation of the bound T cell. Desirably, the antibody or antibody combination preferentially binds or modulates the expansion or activation of only one T cell subpopulation selected from the group of NK T cells, CD1d-reactive T cells, and JαQ⁺ T cells. Desirably a CDR3-loop, an antigen binding site, or an α-β junction of a TCR bound by an antibody or antibody combination of the invention is expressed by a NK T cell, CD1d-reactive T cell, JαQ⁺ T cell, or invariant T cell. In other desirable embodiments, an antibody that binds or modulates the expansion or activation a T cell subpopulation of interest (e.g., NK T cells, CD1d-reactive T cells, JαQ⁺ T cells, or invariant T cells) preferentially binds the antigen binding site of the TCR of the T cell subpopulation of interest. It is also contemplated that the invariant T cells relevant to any of the aspects of the invention may not be CD1d-reactive. Desirable labeled antibodies include antibodies bound to biotin, FITC, PE, or a magnetic bead.

It should be understood that each of the aspects of the invention apply equally to the antibodies, bifunctional antibodies, fragments of antibodies, and derivatives of antibodies of the invention. Each of the aspects of the invention also apply equally to a combination of antibodies that together preferentially bind a CDR3-loop or an α-β junction of the TCR. In various embodiments, the antibodies in an antibody combination of the invention are simultaneously or sequentially contacted with NK T cells, CD1d-reactive T cells, or JαQ⁺ T cells or with a sample containing NK T cells, CD1d-reactive T cells, or JαQ⁺ T cells. In other embodiments, the antibodies in an antibody combination of the invention are simultaneously or sequentially administered to an animal for the treatment or prevention of a disease or condition.

Each aspect of the invention also applies to any antigen-specific oligoclonally expanded T cell subpopulation encountered in animals (e.g., humans, other mammals, and birds) in response to a given antigenic challenge. These antigen-specific oligoclonally expanded T cell subpopulations include those T cells oligoclonally expanded in response to an immunodominant component of the antigen in multiple individuals.

It is also noted that the presentation of an antigen to a T cell of interest does not require an antigen presenting cell (APC). For example, a soluble or immobilized form of an antigen-presenting molecule may be used to present an antigen to a T cell or a sample containing a T cell of interest under conditions that allow the activation or expansion of the T cell without the presence of an APC.

By "CDR3 loop" is meant the amino acids in the junction that is generated by rearrangement between a V segment and a J segment of a TCR-α chain or by rearrangement between a V segment, a D segment, and a J segment of a TCR-β chain. Identification of the CDR3 loop is simplified by the presence of a conserved cysteine at the end of the V segment. The first amino acid after this cysteine is the first residue of the CDR3 loop.

The sequence of a CDR3 loop can be readily identified based on a sequence alignment of the amino acid sequence of a TCR of interest with one or more sequences of other TCRs. For example, a Kabat table which contains an alignment of the amino acid sequence of numerous T cell receptors may be used to identify the CDR3 loop in a TCR-α chain or -β chain of interest (Johnson and Wu, Nuc. Acid. Res. 29(1):205-206, 2001; http://immuno.bme.nwu.edu). The CDR3 loop may also be identified based on a sequence alignment with one or more TCRs for which the CDR3 loop has been identified based on the x-ray crystal structure (Reinherz et al., Science 286(5446):1913-1921, 1999). Additionally, the CDR3 loop may be identified by determining the three-dimensional structure of the TCR chain of interest.

By "antibody that preferentially binds a CDR3-loop, an antigen binding site, or an α-β junction of a TCR," is meant an antibody which recognizes and binds a CDR3-loop, an antigen binding site, or an α-β junction of a TCR or which recognizes and binds a CDR3-loop, an antigen binding site, or an α-β junction of a TCR expressed on a T cell, but which does not substantially recognize and bind other molecules in a sample, e.g., a biological sample, which naturally includes other protein or cells. The signal in the ELISA assay described in Example 1 for the binding of the antibody to a CDR3-loop, an antigen binding site, or an α-β junction of a TCR expressed on a T cell is desirably at least 2, 3, 4, 5, 10, 15, 20, 30, 40, 50, 60, 70, 80, 90, 100, 150, 200, or 500 times greater than that for the binding to a control cell that is not a T cell or to a T cell that expresses TCRs with CDR3-loops, α-β junctions, and antigen binding sites with amino acid sequences that are less than 99, 95, 90, 85, 80, 70, 60, 50, 40, or 20% identical to the corresponding sequence of the CDR3-loop, α-β junction, or antigen binding site preferentially bound by the antibody. Humanized or other species forms of the antibody may be generated using standard techniques.

Desirably, the antibody is "purified," meaning it has been separated from other components that naturally accompany it. Typically, the antibody is substantially pure when it is at least 50%, by weight, free from proteins, antibodies, and naturally-occurring organic molecules with which it is naturally associated. Desirably, the antibody is at least 75%, more desirably, at least 90%, and most desirably, at least 99%, by weight, pure. A substantially pure antibody that preferentially binds a CDR3-loop, α-β junction, or an antigen binding site of a TCR may be obtained, for example, by using a method of the present invention to immunize a mammal for the generation of the antibody, by construction of hybridoma secreting the antibody, by chemically synthesizing the antibody, or by separation of the antibody from natural sources. Purity can be assayed by any appropriate method, as described below for the isolation of antibodies.

By "α-β junction of a TCR" is meant the interface between the α and β chains of a TCR. The interface includes noncovalent interactions between the variable domains of the α and β chains. Desirably, the three-dimensional structure of the α-β junction or a model of the three-dimensional structure of the α-β junction is used in the design of polypeptides or small molecules for immunizing a mammal to generate an antibody to the α-β junction of the TCR. Several three-dimensional structures of the interface between α and β chains of a TCR have been reported and may be used by one skilled in the art to model the interface of the α and β chains of a TCR expressed by a NK, CD1d-reactive, JαQ$^+$, or invariant T cell. For example, based on the modeled or actual structure of the interface of the α and β chains, a small molecule may be designed that has a three-dimensional structure similar to that of an exposed region of the interface. Additionally, a polypeptide may be designed that has a three-dimensional structure similar to that of a portion or all of the α-β junction of a TCR. For example, a modeled or actual structure of a TCR of interest may be used to obtain a modeled or actual structure of the α-β junction of the TCR which can then be mimicked by a designed polypeptide (e.g., a polypeptide of approximately 100 amino acids). Covalent bonds or linkers may be added between the domains of the designed polypeptide so that a single chain polypeptide is generated. For these modeling procedures, any standard modeling program, such as MolScript, may be used.

Similarly, these methods may be used to generate antibodies that preferentially bind the γ-δ junction of a TCR of interest.

By "antigen binding site of a TCR" is meant the region of a TCR that binds an antigen. This region includes part of the exposed surface of the variable region of the TCR. For example, the antigen binding site contains the CDR3-loop of the α chain, the CDR3-loop of the β chain, a predictable portion of the CDR1-loops, a predictable portion of the CDR2-loops, and some nearby structural surfaces.

Desirably, the three-dimensional structure of the antigen binding site or a model of the three-dimensional structure of the antigen binding site is used in the design of polypeptides or small molecules for immunizing a mammal to generate an antibody to the antigen binding site of the TCR. Several three-dimensional structures of antigen binding sites of TCRs have been reported (in the presence or absence of an antigen) and may be used by one skilled in the art to model the antigen binding site of a TCR expressed by a NK, CD1d-reactive, JαQ$^+$, or invariant T cell. Additionally, a modeled or actual structure of CD1d could be used to determine how other compounds would interact with CD1d-reactive T cells. Based on the modeled or actual structure of an antigen binding site, a small molecule or polypeptide may be designed that has a three-dimensional structure similar to that of a portion or all of the antigen binding site. For example, a modeled or actual structure of a TCR of interest may be used to obtain a modeled or actual structure of the antigen binding site of the TCR which can then be mimicked by a designed polypeptide (e.g., a polypeptide of approximately 100 amino acids). Covalent bonds or linkers may be added between the domains of the designed polypeptide so that a single chain polypeptide is generated. For these modeling procedures, any standard modeling program, such as MolScript, may be used.

By "invariant T cell" is meant a T cell having a CD1d-reactive invariant T cell antigen receptor. By "human CD1d-reactive invariant T cell antigen receptor" is meant a T cell antigen receptor that recognizes CD1d and has an alpha chain that is generated from a rearrangement between Vα24 and JαQ that produces little or no N-region diversity (Kent et al., Human Immunology 60:1080-1089, 1999). In mice, the invariant TCR-α chain is generated from a rearrangement between Vα14 and Jα281 that produces little or no N-region diversity. The equivalent rearrangement may occur in other mammals (e.g., rats) and in birds. Although human invariant TCR-α chain pairs preferentially with Vβ11, it can pair with other Vβs. The human CD1d-reactive invariant T cell antigen receptor recognizes CD1d, but not the closely related CD1a, CD1b, or CD1c family members (Exley et al., J. Exp. Med. 186(1):109-120, 1997).

By "fragment" is meant a polypeptide having a region of consecutive amino acids that is identical to the corresponding region of an antibody of the invention. The fragment has the ability to bind, activate, and/or expand T cells ex vivo or in vivo, as determined using the assays described herein. Desirably, the number, activity, or purity of the expanded cells is at least 20, 40, 60, 80, or 90% of that produced by an antibody of the invention, as measured using the assays provided herein. Desirably, the binding of the fragment to the CDR3-loop, α-β junction, or antigen binding site of a TCR is at least 20, 40, 60, 80, or 90% of that of an antibody of the invention.

By "derivative" is meant an antibody or fragment of the invention that is modified chemically or through gene fusion technology or chemical synthesis so that it is covalently linked to a toxin, therapeutically active compound, enzyme, cytokine, radiolabel, fluorescent label, or affinity tag. The covalently linked group can be attached to the amino terminus, carboxy terminus, between the amino and carboxy termini, or to a side chain of an amino acid in the antibody or fragment. By "affinity tag" is meant a peptide, protein, or compound that binds another peptide, protein, or compound. In a desirable embodiment, the affinity tag is used for purification or immobilization of the derivative. In another desirable embodiment, the affinity tag or toxin is used to target the antibody or fragment to a specific cell, tissue, or organ system in vivo. In still another desirable embodiment, the fluorescent or radiolabel is used for imaging of the derivative. In yet another desirable embodiment, the therapeutically active compound or radiolabel is used for the treatment or prevention of a disease or disorder. In another embodiment, the derivative or fragment of an antibody of the invention has increased stability or increased solubility compared to the antibody. It is also contemplated that the antibody, fragment, or derivative of the invention may be bound non-covalently to another antibody covalently linked to a toxin, therapeutically active compound, enzyme, cytokine, radiolabel, fluorescent label, magnetic label, or affinity tag.

By "humanized" is meant alteration of the amino acid sequence of an antibody so that fewer antibodies and/or immune responses are elicited against the humanized antibody when it is administered to a human. For the use of the antibody in a mammal other than a human, an antibody of the invention may be converted to that species format.

By "bifunctional antibody" is meant an antibody that includes an antibody or a fragment of an antibody covalently linked to another antibody or another fragment of an antibody. Desirably, both antibodies or fragments bind to different epitopes expressed on the same T cell. Desirably, at least one antibody included in the bifunctional antibody is an antibody of the invention. Desirably, the antibody binds CD3, CD161, or both CD3 and CD161. In other desirable embodiments, the antibody binds one or more of the following: Vα24, CD94, Vβ11, and anti-CD28.

By "cyclic peptides" is meant a non-linear peptide having an amino acid sequence at least 60%, desirably 80%, more desirably 90%, and most desirably 100% identical to a region in the CDR3 loop of a TCR. In one desirable embodiment, the amino acid sequence of the peptide includes CVVSDRG-STLGRLADCG (SEQ ID NO 1) from the CDR3-loop of the human invariant TCR-α or a region of at least 5, 8, 10, or 15 consecutive amino acids of SEQ ID NO 1. In another desirable embodiment, the amino acid sequence of the peptide is identical to that of SEQ ID NO 1. The peptide may be cyclized by the formation of a covalent bond between the N-terminal amino group of the peptide or the side-chain of residue and the C-terminal carboxyl group or the side-chain of a residue. For example, a peptide lactam may be formed by the cyclization between the N-terminal amino group or an amino group of an amino acid side-chain and the C-terminal carboxyl group or a carboxyl or amide containing side-chain, such as that of glutamic, aspartic acid, glutamine, or asparagine. Other possible cyclizations include the formation of a thioether by the reaction of a thiol group in a cysteine side-chain with the N-terminal amino group, C-terminal carboxyl group, or the side-chain of another amino acid. A disulfide bond may also be formed between two cysteine residues. It is also contemplated that a peptide having an amino acid sequence at least 60%, desirably 80%, more desirably 90%, and most desirably 100% identical to a region of another loop or exposed surface of the alpha or beta chain of the invariant TCR or another TCR may be used for the generation of antibodies to another TCR. Desirable loops include the CDR3-loop of the α or β chain of a NK T cell, CD1d-reactive T cell, or JαQ⁺ T cell.

By "CD1d or invariant T cell deficient mammal" is meant a mammal that when compared to other mammals of the same species has a reduced amount of or lacks functional CD1d molecules, invariant T cells, TCR-α chains, or TCR-β chains. Desirable examples of such mammals include a CD1d knockout mouse (Sonoda et al., 1999, supra), a mammal not tolerized to the invariant TCR, a mammal in which invariant T cells have been removed, a mammal lacking part of the TCR-α chain (Cui et al., Science 278:1623, 1997), mammal lacking part of the VB8 molecule, or animals deleted of invariant, NK T cells, or related subpopulations by antibodies, cytokines, or repeated antigenic stimulation.

By "immunizing" is meant administering to an animal (e.g., a mammal or a bird) either peptides coupled to carriers, invariant T cells, or both using standard procedures. Desirable routes of administration include intraperitoneally, intramuscular, intradermal, and subcutaneous. The dose and frequency of administration can be determined using standard procedures.

By "isolating antibodies" is meant purifying the antibody from antiserum, ascites fluid, or hybridomas supernatant. The antibodies can be purified by one skilled in the art using standard techniques such as those described by Ausubel et al. (Current Protocols in Molecular Biology, volume 2, p. 11.13.1-11.13.3, John Wiley & Sons, 1995). The antibody is desirably at least 2, 5, or 10 times as pure as the starting material, as measured using polyacrylamide gel electrophoresis, column chromatography, optical density, HPLC analysis, or western analysis to detect a reduction in the amount of contaminating proteins or ELISA to detect an increase in specific activity for binding to markers for a particular T cell subpopulation.

By "contacting" is meant incubating a sample with an antibody or cytokine. The antibody or cytokine can be in a soluble form, or it can be immobilized. In one embodiment, the immobilized antibody or cytokine is tightly bound or covalently linked to a bead or plate. In desirable embodiments, the contact occurs ex vivo or in vivo.

By "measuring" is meant determining the percentage of cells in a sample that belong to a specific T cell subpopulation or determining the number of cells in a sample that belong to a specific T cell subpopulation, as described herein. In a desirable embodiment, the T cells are NK T cells, CD1d-reactive T cells, or JαQ⁺ T cells.

By "treating or preventing" is meant administering an antibody of the present invention or T cells that have been incubated with the antibody to a mammal, as described herein.

By "T cell pathogenesis" is meant a disease or disorder that is caused or exacerbated by an activity of T cells, such as their cytokine production or cytotoxicity.

By "autoimmune disease" is meant a disease in which an immune system response is generated against self epitopes. Some examples of autoimmune diseases include insulin dependent diabetes mellitus, rheumatoid arthritis, pemphigus vulgaris, multiple sclerosis, and myasthenia gravis.

By "increasing size of a subpopulation of T cells" is meant stimulating the expansion of these cells by incubating them with an antibody or incubating them with an antigen and antigen presenting cells. Desirably, the number of T cells belonging to the subpopulation that are present after this incubation is at least 2, 3, 4, 5, 10, 15, 20, 30, 40, 50, 70, 90, 150, or 500 fold greater than the number of these cells present after the corresponding control incubation in the absence of the antibody or the antigen and antigen presenting cells. More desirably, the number of T cells belonging to the subpopulation that are present after this incubation is at least 2, 5, 10, 20, or 50 fold greater than the number of these cells present after the corresponding incubation in the presence of 0.1-2 µg/ml phytohemagglutinin (PHA). It is also contemplated that the percentage may remain the same but the actual numbers of the relevant subset may increase if the total number of T cells increases. Desirably, the change in the percentage of cells that belong to the subpopulation of T cells is at least 2, 5, 10, 20, or 50 fold greater than corresponding change in the percentage of cells that belong to the subpopulation of T cells in a control sample that has not be incubated with the antibody. In another desirable embodiment, the T cells are NK T cells, CD1d-reactive T cells, or JαQ⁺ T cells.

By "preferentially modulating the expansion or activation of at least one T cell subpopulation selected from the group of NK T cells, CD1d-reactive T cells, and JαQ⁺ T cells" is meant inducing or inhibiting the expansion or activation of NK T cells, CD1d-reactive T cells, or JαQ⁺ T cells. The induction of the expansion of these T cell subpopulations may be measured as described for determining the increase in the size of the subpopulation of T cells. The inhibition of the expansion of these T cell subpopulations may be determined by comparing the number of T cells belonging to the subpopulation after incubation with an antibody of the invention compared to a control incubation without the antibody. Desirably, the number of T cells belonging to the subpopulation present after incubation with the antibody is 2, 3, 4, 5, 10, 15, 20, 30, 40, 50, or 100 fold less than the number of these T cells present after the corresponding control incubation. This inhibition of T cell expansion may be useful in the prevention or treatment of T cell pathogenesis. The induction or inhibition of the activation of a T cell subpopulation may be assayed using standard procedures to measure the cytokine production or cytotoxicity of the T cell subpopulation. Desirably, the increase or decrease in the cytokine production or cytotoxicity is at least 5, 10, 20, 20, 40, 50, 70, 90, or 100% of the activity of the control T cell subpopulation incubated in the absence of the antibody. Desirably, the change in the size or activity of at least one T cell subpopulation selected from the group of NK T cells, CD1d-reactive T cells, and J$\alpha$Q$^+$ T cells is least 2, 3, 4, 5, 10, 15, 20, 30, 40, 50, 70, 90, 150, or 500 times greater that the corresponding change in cells other than NK T cells, CD1d-reactive T cells, and J$\alpha$Q$^+$ T cells. In a desirable embodiment, the antibody preferentially binds or modulates the expansion or activation of only one of the T cell subpopulations selected from the group of NK T cells, CD1d-reactive T cells, and J$\alpha$Q$^+$ T cells.

By "anti-V$\alpha$24, CD4, CD8, CD56, CD161, CD94, CD28, or V$\beta$11 antibody" is meant an antibody that recognizes and binds V$\alpha$24, CD4, CD8, CD56, CD161, CD94, CD28, or V$\beta$11 molecules or cells expressing one of these molecules, but which does not substantially recognize and bind other molecules in a sample, e.g., a biological sample, which naturally includes other protein or cells.

By "obtaining a sample comprising T cells" is meant removing a sample that has T cells from a mammal or acquiring a sample that has these cells and is produced by a mammal. In a desirable embodiment, the sample is peripheral blood. In another embodiment, the sample is a bodily fluid, such a urine, bile, or a bodily tissue. In another embodiment, the sample is a bone marrow or an umbilical cord sample.

By "purifying the T cells" is meant isolating the cells from a sample that naturally contains other cells. The T cells can be purified using an antibody of the invention or an anti-V$\alpha$24, CD4, CD8, CD56, CD161, or V$\beta$11 antibody in standard procedures. Desirable methods of purification include fluorescence-activated cell sorting (FACS), immunoprecipitation, immunoaffinity chromatography, magnetic bead immunoaffinity purification, and cell panning with a plate-bound antibody. Desirably, the purified T cells are at least 2, 5, 10, 50, 100, 500, or 900 times as pure as the original sample, as measured using ELISA or FACS analysis to detect binding of the purified T cells to markers for the T cell subpopulation in which they belong.

By "purified T cell subpopulation" is meant a substantially pure T cell subpopulation that is isolated from a sample that naturally contains other cells. The purified T cell subpopulation is enriched for at least one of the following: NK T cells, CD1d-reactive T cells, or J$\alpha$Q$^+$ T cells. Desirably, the T cell subpopulation is enriched for only one of the following: NK T cells, CD1d-reactive T cells, or J$\alpha$Q$^+$ T cells. The purified T cell subpopulation is more pure than the purity of the T cell subpopulation found in nature. Desirably, the purified T cell subpopulation is at least 1, 5, 15, 30, 50, 75, 90, or 99%, by number, free from cells with which it is naturally associated. Typically, these other cells that are associated with the T cell subpopulation differ from the T cells belonging to the subpopulation by not expressing a cell-surface molecule, not binding a ligand, or not having an activity of the T cell subpopulation.

By "complex" is meant an antibody-bound T cell in which the binding of the antibody to the T cell is sufficient to enable the isolation or separation of the complex from a sample.

By "recovering the cells from the complex" is meant separating the T cells from the antibody using standard procedures.

Other features and advantages of the invention will be apparent from the following detailed description.

BRIEF DESCRIPTION OF THE DRAWING

FIG. 12 is a table showing the percent of T cells that stain with the indicated antibodies after a single round four to eight week expansion in T cell medium. The "PBMC" column represents PBMC cells that were not sorted prior to expansion. The "Dynal @ 40" column represents PBMC cells that were purified using 6B11-Dynal beads prior to expansion. The "Milenyi @ 20" column represents PBMC cells that were sorted using 6B11 (20 µg/mL coating)-Milenyi beads prior to expansion. For comparison, the corresponding results for unsorted whole leukopak 21 (LKP 21) cells are listed. For FIGS. 12-17, a standard T cell medium such as RPMI-1640 or BioWhittaker medium with 10% FBS and 100 U/mL human recombinant IL-2 was used.

FIG. 13 is a table showing the percent of T cells that stain with the indicated antibodies after purification using 6B11-Dynal beads and a single round four to eight week expansion in T cell medium. For comparison, the corresponding results for unsorted whole leukopak 10 (LKP 10) cells are listed. As indicated in the table, some of the T cell expansions were conducted in the presence of T cell medium ("TCM") containing IL-7 at 10 ng/ml, IL-5 at 10 ng/ml, dexamethasone ("Dex") at 1 µM, and/or 6B11 antibody at 40 µg/mL. The figure numbers listed to the right some of the rows in the table indicate figures illustrate the results from the T cell expansions.

FIG. 14 is a table showing the percent of T cells that stain with the indicated antibodies after a single round four to eight week expansion in T cell medium. For comparison, the corresponding results for unsorted whole leukopak 14 (LKP 14) cells are listed. The results for cells that were sorted with 6B11-Dynal beads prior to expansion are compared to unsorted control cells. As indicated in the table, some of the T cell expansions were conducted in the presence of 6B11 antibody as above, PHA (1 µg/mL), and/or equivalent numbers of autologous APCs.

FIG. 15 is a table showing the percent of T cells that stain with the indicated antibodies after a single round four to eight week expansion in T cell medium. The results for cells that were sorted with 6B11-Dynal beads prior to expansion are compared to unsorted control cells (LKP 13). Some of the T cell expansions were conducted in the presence of 6B11 antibody, PHA, allogenic APCs, and/or autologous APCs, as described above.

FIG. 16 is a table showing the percent of T cells that stain with the indicated antibodies after purification using 6B11-Miltenyi magnetic beads and a single round four to eight week expansion in T cell medium compared to unsorted control cells (LKP 2). These T cell expansions were conducted in the presence of autologous APCs, as described above. During one of the T cell expansions, 10 ng/ml IL-7 and IL-15 were also present.

FIG. 17 is another table showing the percent of T cells that stain with the indicated antibodies after purification using 6B11-Miltenyi magnetic beads and a single round four to eight week expansion in T cell medium. These T cell expansions were conducted in the presence of autologous APCs and PHA and are compared to unsorted control cells (LKP 11, 12). During the T cell expansions, 6B11 antibody, and/or Vα24 antibody were also present as described above and as indicated in the table. During one of the T cell expansions, 10 ng/ml IL-7 and IL-15 were also present. The figure numbers listed to the left some of the rows in the table indicate figures illustrate the results from the T cell expansions.

FIGS. 22A and 22B show the IL-4 and IFN-γ production, respectively, from a prostate cancer patient versus α healthy donor derived invariant NK T cell line. FIGS. 22C and 22D are graphs summarizing the cytokine production results by CD1d stimulated invariant NK T cells and PHA stimulated bulk T cells, respectively from a series of advanced prostate cancer patients (●) and healthy donors (□). FIG. 22E is a graph of IFN-γ/IL-4 ratios (mean plus standard deviation) for invariant NK T cells (top) or conventional bulk T cells (bottom) from healthy donors and advanced prostate cancer patients. "Cancer+IL-12" are samples from advanced prostate cancer patients treated in vitro with IL-12.

FIGS. 23A-23D are tables illustrating the use of the 6B11 antibody to determine the frequency of CD1d-restricted T cells in HIV patients.

FIG. 24 is a table illustrating the use of the 6B11 antibody and the anti-Vα24 antibody to determine the frequence of CD1d-restricted T cells in diabetic patients.

FIG. 25A is a table illustrating the genes that are differentially expressed between NK T cell clones ME10 and GW4. Genes populating the six expression clusters for the eleven gene functional categories are listed. Each gene is identified by GenBank accession number (or TIGR identifier for HT designations), followed by a common name and the specific cluster into which it fell (row, column).

FIGS. 26A and 26B compare the changes of expression on genes for cytokines and chemokines between the Vα24JαQ T cell clone GW4 (IL-4$^+$) and the ME 10 (IL-4-null) clone. For each individual transcript the anti-CD3 induced hybridization intensity is shown. RNA was isolated, amplified and hybridized to genechips displaying probes for 250 genes of immunological interest (Affymetrix, San Jose, Calif.). This chip is custom designed for quantitative analysis by increasing the number of address features for the detection of each specific transcript. The values for the number of copies of specific mRNA per million after treatment with IgG 1 control are represented by open circles; O, and their corresponding copy numbers after activation with anti-CD3 treatment by closed circles; ● Genes which were called significantly different by a gene expression algorithm and which changed by at least 2-fold are indicated by a bold line. The letter (A) denotes that the transcript was not detected, and it should be noted that the transcripts for MIP-1α and MIP-1β were suppressed by anti-CD3 stimulation in clone ME10. FIG. 26C is a graph showing the amount of cytokines produced by supernatants from several Vα24JαQ T cell clones, based on quantitative ELISA analysis. FIG. 26D is a graph showing the expression of CD40L. The T cell clone BW5 was activated for four hours with PMA/ionomycin stimulation and analyzed by flow cytometry.

FIG. 27A shows the restriction of cytokine release and proliferation. T cell clones were co-cultured with C1R transfectants (expressing CD1a, CD1b, CD1c, or CD1d) or plate-bound anti-CD3. Secreted IL-4, IFN-γ, or proliferation was assayed as described herein. FIG. 27B shows the restriction of cytolysis. The panel of C1R transfectants was screened for cytolysis by Vα24JαQ T cell clones in standard four hour $^{51}$Cr-release assays.

FIG. 28B is a picture of the immunoblot analysis of dendritic cells and control C1R transfectant cells (expressing CD1a or CD1d). FIGS. 28C-28J are pictures of the immunohistochemical staining of serial sections of a representative reactive lymph nodes biopsy (total of 10 biopsies). FIG. 28C is a picture of hematoxylin-eosin staining at low power, and FIG. 28D is a picture of anti-CD3 staining. The box outlines the region through which serial sections were taken for staining with the various markers shown at higher magnification views in FIGS. 28E and 28F; (FIG. 28E) S100; (FIG. 28F) CD1d; (FIG. 28G) CD1a; (FIG. 28H) CD34. Staining of sinus histiocytes (FIGS. 28I and 28K), and parafollicular regions (FIGS. 28L and 28M) for: hemato28ylin-eosin, (FIGS. 28I and 28L); CD68, a macrophage marker, (FIGS. 28J and 28M); and CD1d, (FIGS. 28K and 28N) are shown.

FIG. 29A is graph showing the allogenic lysis of immature and mature dendritic cells by Vα24JαQ T cell clone GW4 in chromium release assays. The haplotypes of the donors were: 1) Clone GW4, A2, A24, B8, B38, Cw7, DR3, DQ2; 2) DC donor M, A2, A68, B7, B45, Cw6, Cwl5; 3) DC donor 0, A2, A24, B46, B60, DR14, DRw52, DQ1; 5) Donor B, A1, A3, B7, B8, DRB1*1501, DRB5*0101, DQB1*0601. FIGS. 29B and 29C are graphs of the autologous and allogenic cytolysis of dendritic cells by Vα24JαQ T cell clones. FIG. 29D is a graph of the abrogation of cytolysis by calcium chelation and inhibition by addition of the anti-CD1d monoclonal antibody, 42.1. Clones BW3 and BW5 were co-cultured with subject BW DC in the presence or absence of EGTA and MgCl$_2$ (4 mM each) or F(ab')$_2$ fragments from monoclonal antibody 42.1 or control IgG at 100 µg/ml.

DETAILED DESCRIPTION

Figure 1:
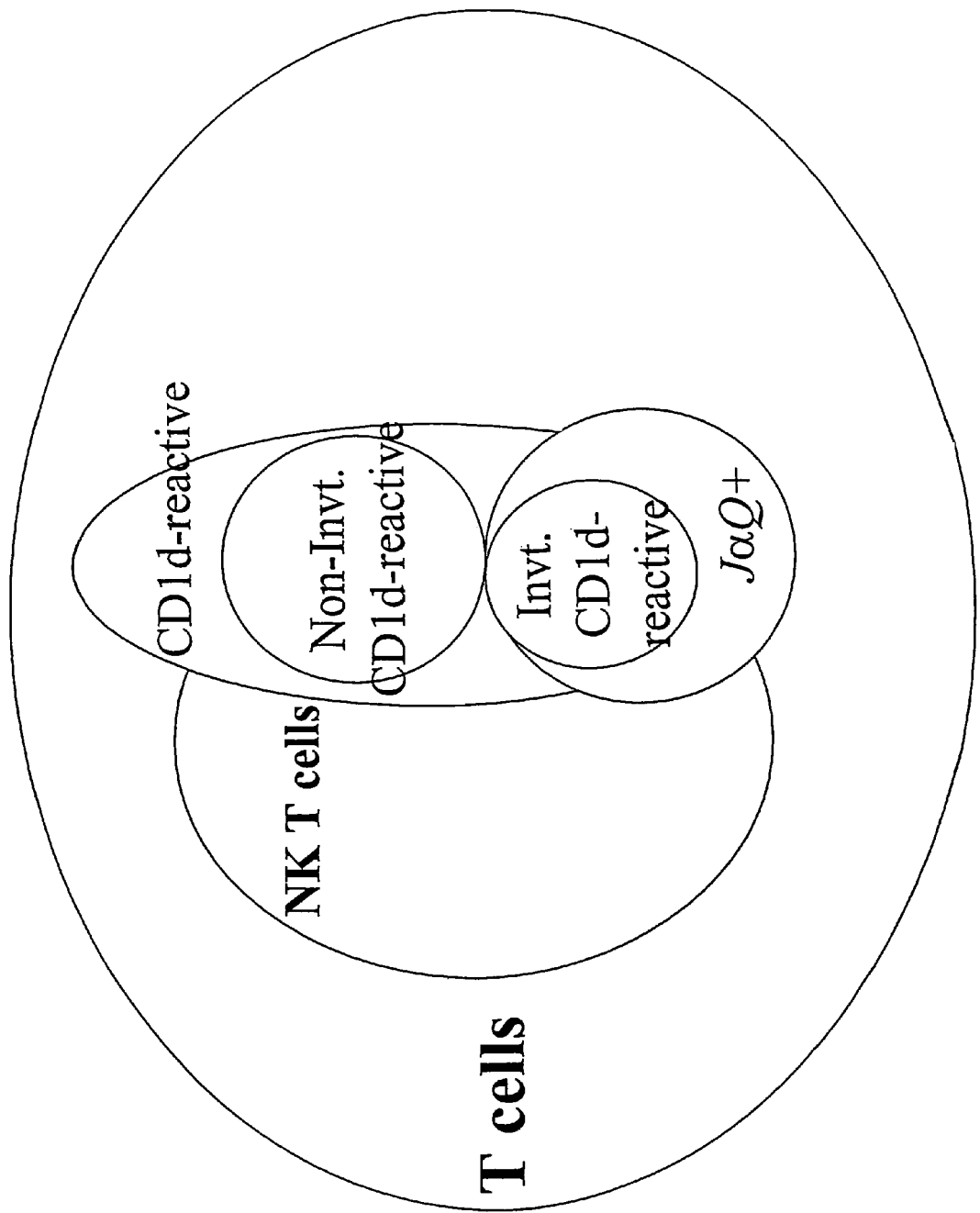
FIG. 1 is a schematic illustration of the relationship between NK T cells, CD1d-reactive invariant T cells, CD1d-reactive noninvariant T cells, and J$\alpha$Q$^+$ T cells.

We have developed methods to generate antibodies to the T cell antigen receptors (TCRS) of NK T cells, CD1d-reactive T cells, or JαQ$^+$ T cells (FIG. 1). The invention also provides purified antibodies to TCRs of NK T cells, CD1d-reactive T cells, or JαQ$^+$ T cells which are useful for diagnostic, imaging, and therapeutic applications for diseases or conditions that are affected by the number and/or activity of T cells or specific subpopulations of T cells. Examples of such diseases or conditions include autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, and cancer. The ex vivo or in vivo expansion of NK T cells, CD1d-reactive T cells, or JαQ$^+$ T cells using the antibodies of the invention may be performed alone or in conjunction with the administration of other therapeutics, such as cytokines or tumor vaccines.

The use of an anti-CDR3-loop monoclonal antibody for the expansion of NK T cells, CD1d-reactive T cells, or J$\alpha$Q$^+$ T cells instead of the use of an antigen, such as $\alpha$-GalCer, would eliminate the requirement for autologous APCs, removing them as potential sources of variability and greatly simplifying the procedure for clinical trials. In addition, the use of a monoclonal antibody (monoclonal antibody) would allow specific expansion of NK T cells, CD1d-reactive T cells, or J$\alpha$Q$^+$ T cells as opposed to nonspecific polyclonal T cell expansion from multiple cell types.

The antigen receptor of almost every individual clone of B and T lymphocytes is the product of a unique random somatic rearrangement. These rearrangements cause even identical twins to have millions of receptors that differ from one another. By contrast, the CD1d-selective and -reactive invariant TCR utilized by the invention represents a uniquely universal target. Because the sequence of the CDR3 loop of invariant TCR-$\alpha$ is identical in all individuals, this region is used to generate novel monoclonal and polyclonal antibodies that recognize the human invariant TCR-$\alpha$ chain. The monoclonal antibodies can preferentially identify and expand invariant T cells ex vivo from normal donors. Our methods of cell expansion using monoclonal antibodies of the present invention yield population sizes of approximately >$10^8$ invariant T cells in bulk cultures and >$10^7$ cells for individual clones starting with 10-20 ml of peripheral blood. As few as tens of thousands of invariant T cells have been shown to be functional in cell transfer experiments performed on mice (Sonoda et al., supra). Thus, human phase 1 clinical trials can incorporate a dose escalation arm, such as starting with about $10^6$ cells, and targeting a maximal dose of $10^9$ cells. Infusions of this range of cells is expected to be well tolerated. For example, donor leukocyte infusions routinely employ on the order of $10^{10}$ unpurified cells without significant side-effects.

In addition to their anti-tumor effect, NK T cells, CD1d-reactive T cells, and J$\alpha$Q$^+$ T cells may contribute to the Th1 protective immune responses against intracellular pathogens. For example, we found that the immune response to an acute cytopathic virus (encephalomyocarditis virus, EMCV-D) is defective in CD1d knockout mice (Exley et al, J. Leuk Biol. 69:713, 2001). These results suggest that the antibodies of the present invention may also be used in the prevention or treatment of infectious disease, including diseases caused by viruses, bacteria, parasites, fungi, protozoa, or other eukaryotic pathogens.

Because NK T cells, CD1d-reactive T cells, and J$\alpha$Q$^+$ T cells are capable of augmenting Th1, Th2, or immune deviation responses depending on stimulus conditions, the response of the NK T cells, CD1d-reactive T cells, and J$\alpha$Q$^+$ T cells can be modulated by either the in vivo administration of a cytokine before, during, or after the infusion of the ex vivo expanded NK T cells, CD1d-reactive T cells, and J$\alpha$Q$^+$ T cells or by conducting the ex vivo expansion of the cells in the presence of a cytokine, or a combination of both methods. Using a cytokine, such as IL-12, IL-15, or IL-18, which is known to bias T cells towards Th1 responses is expected to increase the effectiveness of NK T cells, CD1d-reactive T cells, and J$\alpha$Q$^+$ T cells in the prevention or treatment of cancer, infectious disease, allergies, asthma, pregnancy, and inflammation. Alternatively, any other cytokine, such as IL-2, IL-4, IL-7, IL-10, IL-12, IL-13, IL-15, IL-18, IFN-$\alpha$/$\beta$, IFN-$\gamma$, and GM-CSF, may be used to bias the T cells towards Th2 responses for the prevention or treatment of autoimmune diseases and graft versus host disease for which Th2 responses are protective. Alternatively, the cytokine may be used to bias the T cells away from Th1 and Th2 responses and towards immune deviation responses which may contribute to the maintenance of pregnancy. Immune deviation responses include the suppression of an ongoing immune response, such as a response at a immune-privileged site. TGF-$\beta$ and IL-10 are examples of cytokines that may participate in immune deviation responses (Sonoda et al, supra).

In addition to their use in expanding NK T cells, CD1d-reactive T cells, or J$\alpha$Q$^+$ T cells ex vivo, the antibodies of the present invention may be administered to a mammal, such as a human, to increase the number of NK T cells, CD1d-reactive T cells, or J$\alpha$Q$^+$ T cells in vivo for the prevention or treatment of autoimmune diseases, infectious diseases, allergies, asthma, inflammatory conditions, graft versus host disease, graft rejection, immunodeficiency disease, spontaneous abortion, pregnancy, or cancer. For example, reduced levels of certain T cells such as invariant NK T cells were found in prostate cancer, multiple sclerosis, HIV, and type 1 diabetes patients (Examples 9, 11, and 12). Additionally, a reduced number of V$\alpha$24$^+$ CD161$^+$ T cells has been previously reported for melanoma patents (Kawano et al., Cancer Res. 59:5102, 1999) Thus, the loss of invariant NK T cell function may be a general finding in advanced cancer. Alternatively, antibodies that bind and inhibit the expansion or an activity of NK T cells, CD1d-reactive T cells, and J$\alpha$Q$^+$ T cells, such as cytokine production or cytotoxicity, may be used to inhibit T cell pathogenesis in a mammal. For example, an allergy may be caused or exacerbated by the Th2 response of NK T cells, CD1d-reactive T cells, or J$\alpha$Q$^+$ T cells, and thus, inhibiting the expansion or Th2 response of NK T cells, CD1d-reactive T cells, or J$\alpha$Q$^+$ T cells may be useful in the prevention or treatment of this condition. Similarly, reducing the Th1 response of NK T cells, CD1d-reactive T cells, or J$\alpha$Q$^+$ T cells may improve, stabilize, or prevent autoimmune diseases or prevent spontaneous abortions. The Th1 response induced by infectious agents, such as Hepatitis viruses, can also cause damage which may be minimized by the inhibition of these cells. Examples of some of the antibodies that may inhibit these cells include monovalent or Fab molecules or antibodies that are conjugated to a toxin or radiolabel that damages the cells upon binding of the antibody to the cells. The antibodies may also bind to an TCR expressed on the cells and prevent the binding of a ligand to the TCR.

The antibodies of the invention may also be used for imaging applications. In particular, the antibodies can be coupled to a fluorescent or radiolabel for use in visualizing NK T cells, CD1d-reactive T cells, or J$\alpha$Q$^+$ T cells in vivo or in samples of biopsies, blood, and other bodily material or fluids. The antibodies may also be used to purify NK T cells, CD1d-reactive T cells, or J$\alpha$Q$^+$ T cells from these samples. The antibodies of the present invention may also bind to other NK T cells, CD1d-reactive T cells, or J$\alpha$Q$^+$ T cells that are not invariant T cells and that are more abundant than invariant T cells in some locations, such as the bone marrow and liver. Using an antibody of the present invention to purify invariant T cells from a peripheral blood sample, in which approximately 0.1% of the cells are invariant T cells, has enabled the isolation of cells that are 90-95% invariant T cells. Even higher purity may be achieved by using multiple rounds of purification or using multiple antibodies per round.

Additionally, greater purity or greater cell numbers may be achieved by also contacting the T cells with an antigen and antigen presenting cells (APCs). Any antigen (e.g., a protein, peptide, lipid, carbohydrate, nucleic acid, infectious agent, or small molecule) for the T cells of interest may be used. Examples of possible antigens for CD1d-reactive T cells include lipid or glycosyl-phosphatidylinositol antigens from an infectious pathogen and α-GalCer. Other possible antigens include peptide and protein antigens, such as those presented by a class I or class II MHC molecule.

Additionally, an antigen may be presented to a T cell of interest in the absence of APCs. For example, a soluble, liposome-associated, or immobilized form of an antigen-presenting molecule (e.g., CD1d, class I MHC, or class II MHC) may be used to present an antigen (e.g., a lipid or a peptide) to a T cell or a sample containing a T cell of interest under conditions that allow the activation or expansion of the T cell without the presence of an APC. The antigen-presenting molecule that is used may be a naturally-occurring molecule or may be a chemically or genetically modified molecule. For example, the molecule may be expressed as a fusion protein, such as a GST, maltose-binding protein, hexa-histidine, or Fc region fusion protein. An antigen-presenting molecule expressed as a fusion protein containing a membrane-binding domain, transmembrane domain, or hydrophobic region may be mixed with lipid molecules to form a liposome or micelle containing the fusion protein. This liposome or micelle having an antigen-presenting cell on its surface mimics the ability of an APC to present an antigen to a T cell. Alternatively, an antigen-presenting molecule may be immobilized on a solid support, such as any rigid or semi-rigid surface. The support can be any porous or non-porous water insoluble material, including, without limitation, membranes, filters, chips, slides, wafers, fibers, magnetic or nonmagnetic beads, gels, tubing, strips, plates, rods, polymers, particles, microparticles, and capillaries. If desired, the support can have a variety of surface forms, such as wells, trenches, pins, channels and pores, to which the proteins are bound.

An antigen-presenting molecule that is either in solution, immobilized on a solid support, or contained in a liposome or micelle may be contacted with an antigen for the T cell subpopulation of interest under conditions that allow the antigen-presenting molecule to bind the antigen. This antigen may then interact with T cells of interest, resulting in the expansion and/or activation of the T cells. These methods in which a T cell of interest is expanded or activated by an antigen in the absence of APCs may be desirable in a clinical setting in which extra cells, such as APCs may be undesirable.

Using the antibodies of the invention for the quantitation of invariant T cells by flow cytometry has many advantages over the current methods. The current methods include either flow cytometry with less specific antibodies or a PCR-based method, which involves synthesizing and amplifying cDNA corresponding to the mRNA encoding the TCR-α chain and comparing this amplified cDNA to that from an invariant T cell clone and a control T cell clone, as described in Example 6. The flow cytometry method has the advantage of determining the total number of invariant T cells; while the PCR-based method only determines the relative frequency of invariant T cells in a sample. Moreover, flow cytometry allows the determination of which markers are expressed on the invariant T cells. The flow cytometry method is also a simpler and faster method which may be performed in about an hour compared to about a day for the PCR method and which does not require skill in molecular biology techniques. Thus, the flow cytometry method using the antibodies of the present invention may be more desirable in a clinical setting. Similar methods may also be used to quantitate other NK T cells, CD1d-reactive T cells, or JαQ⁺ T cells using the antibodies of the present invention.

Additionally, the antibodies can be used in diagnosing a subject that has or is at risk for a disease. As described in Examples 6, 9, and 10, the antibodies can be used to quantitate the number of NK T cells, CD1d-reactive T cells, or JαQ⁺ T cells and to isolate these cells for the measurement of their cytokine production and cytotoxicity activities. These parameters can be compared between the subject and subjects who have and/or do not have the condition to diagnose the risk for, presence of, severity of, stage of, recovery from, or remission of a condition.

The following examples are to illustrate the invention. They are not meant to limit the invention in any way. It should be understood that the methods described in the following examples may be applied to NK T cells, CD1d-reactive T cells, JαQ⁺ T cells, and/or invariant T cells.

EXAMPLE 1

Generation of Antibodies to a Human NK T Cell Antigen Receptor Alpha Chain

Because all invariant TCR⁺ T cells from all individuals have the same amino acid sequence in the CDR3 loop, this region was used in the design of peptides for the generation of anti-CDR3-loop antibodies. Because the murine and human sequence of the CDR3 loop are nearly identical (CVVSDRGST and CVVGDRGSA; SEQ ID NOs 2 and 3, respectively), a peptide with the human CDR3 loop sequence that is administered to mice might be recognized by the murine immune system as a self peptide and thus not induce the production of antibodies.

To overcome this potential problem, CD1d knockout mice (Sonoda et al., supra) which lack invariant TCR⁺ T cells were used as the host for the production of anti-CDR3-loop antibodies. Since these mice lack the invariant TCR-α chain they are able to recognize peptides containing the human CDR3 loop sequence as foreign, and thus, generate antibodies against this epitope.

For the production of antibodies and hybridomas, a peptide (CVVSDRGSTLGRLADCG, SEQ. ID No. 1) with an amino acid sequence corresponding to a portion of the CDR3 loop of the human invariant TCR-α chain was used. This peptide was cyclized by reaction of the N-terminal amino group with the C-terminal carboxyl group. The cyclic peptide was coupled to a keyhole limpet hemocyanin carrier and administered to CD1d KO mice, using standard techniques. The peptide coupled to bovine serum albumin was administered as booster injections. Invariant TCR⁺ T cells were later administered to some mice to further stimulate the immune system. Serum from the mice was tested for antibodies that bound the peptide coupled to ovalbumin, using a standard ELISA assay. Hybridomas were generated from seropositive mice spleens using standard techniques. ELISA positive hybridoma wells were further tested by FACS to compare binding of the antibodies to Vα24JαQ clones versus negative controls. Cells producing antibodies that bound the Vα24JαQ clones but not the negative controls were cloned and fused to immune spleen cells using standard techniques. A group of hybridomas secreting monoclonal antibodies that specifically recognized the peptide were then identified using the ELISA assay. Subsequent selective screenings for clones that recognized the invariant TCR-α chain expressed on intact NK T cells involved repetitive cloning of the hybridoma, assaying by FACS for binding to cells expressing the invariant TCR-α chain but not to negative controls, and confirmation of specific binding to the peptide by ELISA. These stable monoclonal antibody secreting hybridomas clones may be used by one skilled in the art for the production and purification of clinical trial quality and quantity of these monoclonal antibody reagents.

Figures 2A, 2B:
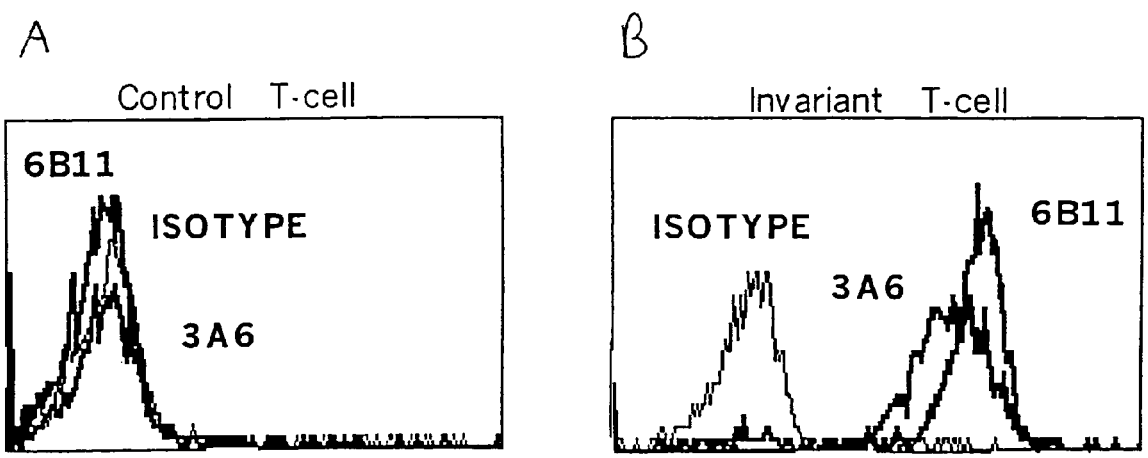
FIG. 2A is a histogram of the staining of a control T-cell clone with the anti-CDR3-loop monoclonal antibodies (3A6 or 6B11) or a 6B11 isotype (IgG1) matched control.
FIG. 2B is a histogram of the corresponding staining of an invariant NK T cell clone.
Figures 3A, 3B:
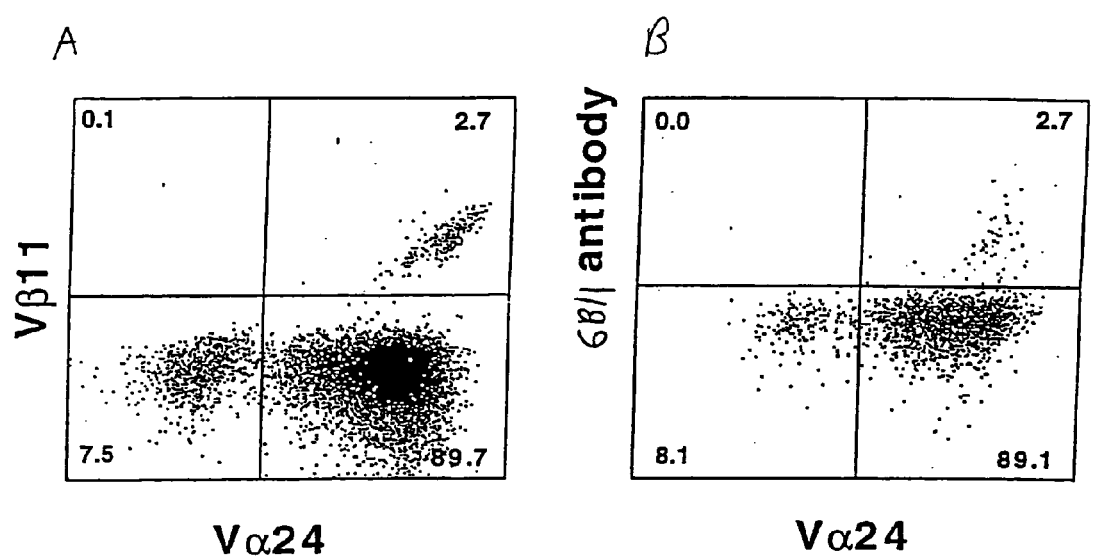
FIGS. 3A and 3B are dot plots showing the FACS analysis of the recognition of V$\alpha$24$^+$ T cells by the 6B11 monoclonal antibody (ATCC Deposit No. PTA-11305; deposited Sep. 14, 2010; American Type Culture Collection (ATCC), 10801 University Blvd., Manassas, Va. 20110-2209). FACS purified V$\alpha$24$^+$ T cells were expanded ex vivo for 2 weeks with PHA and analyzed using V$\alpha$24-PE and V$\beta$11-FITC (FIG. 3A) or V$\alpha$24-PE and 6B11-FITC monoclonal antibodies (FIG. 3B).

Two antibodies (3A6 and 6B11) were identified that preferentially recognize human invariant T cells (FIG. 2). 6B11 is an IgG1, and 3A6 is an IgM. To demonstrate that 6B11 was not exclusively a Vα24 monoclonal antibody, PHA was used to expand bulk Vα24+ T cells purified by FACS. These cells were then analyzed with Vα24, Vβ11 and 6B11 monoclonal antibodies (FIG. 3). The results demonstrate that 6B11 recognizes a small fraction of the Vα24+ T cells, similar to the Vβ11 monoclonal antibody. Additionally, a single cell sorting from multiple donors was performed and resulted in the establishment of clones from 6B11+ T cells. 6B11 was also shown to induce cytokine responses identical to CD1d+ targets. 6B11 obtained by methods according to the invention has been deposited in conformity with the requirements of the Budapest Treaty at the American Type Culture Collection (ATCC®), 10801 University Blvd., Manassas, Va., 20110 on Sep. 14, 2010. It has been attributed ATCC® Patent Deposit Designation Accession No. PTA-11305.

This method for the production of antibodies reactive with a CDR3 loop may be also performed for any TCR of interest. The sequence of the CDR3 loop of a TCR-α chain or -β chain of interest may be determined based on a sequence alignment with other TCR-α chains or -β chains or based on a modeled or experimentally determined three-dimensional structure of the TCR-α chain or -β chain of interest (Johnson and Wu, Nuc. Acid. Res. 29(1):205-206, 2001; http://immuno.bme.nwu.edu). A cyclic peptide containing the sequence of this CDR3 loop may be used as the antigenic peptide for the production of antibodies reactive with the CDR3 loop, as described above. This cyclic peptide may be administered to an animal (e.g., a laboratory animal or an animal of veterinary interest) in one or more doses. To further enhance the production of antibodies, the T cells of interest may also be administered to the animal. Examples of mammals that may be used for the production of antibodies include mice, rats, rabbits, pigs, goats, sheep, horses, and cattle. Examples of birds that may be used include chickens and turkeys. The host animals may be wild-type animals, or they may be animals that have a reduced level or that lack the T cell subpopulation to which the antibody is being generated. Other animals that may be used include animals that naturally, through genetic modification, or depletion lack the T cells. Any other animal that is capable of producing antibodies may also be used for the production of antibodies of the invention.

The resulting antibodies may be used for diagnostic or clinical applications involving other animals of the same genus or species as the host animal used for antibody production. Additionally, the antibodies of the invention may be used in applications involving animals of a different genus as the host animal. For example, antibodies that are produced in chickens may be used for the treatment or prevention of disease in other chickens or in other birds.

To generate antibodies for the treatment, prevention, or diagnosis of a particular disease or condition, the CDR3 loop of a T cell subpopulation that is associated with that disease or condition may be used (see, for example, Table 1). For example, T cell subpopulations that are present at increased or decreased levels or that have increased or decreased activity in subjects with a disease or condition relative to the corresponding T cell subpopulation in control subjects without the disease or condition may be used for the generation of antibodies of the invention. Additionally, T cells may be isolated from a sample (such as a biopsy sample) obtained from a subject with a disease or condition. The identity of T cell subpopulations in the sample may be determined using standard techniques, such as by FACS analysis using antibodies reactive with various T cell markers or by sequencing of the TCR-α chains or -β chains. The CDR3 loop from an isolated T cell subpopulation may be used for the production of antibodies. These antibodies may be administered to subjects with the disease or condition (including the original subject from whom the T cell subpopulation was isolated as well as other subjects with the condition) to modulate the number and/or activity of relevant T cells in vivo. The antibodies may also be used for ex vivo expansion of the relevant T cells followed by readministration of the expanded T cells to the subject.

Antibodies of the invention may also be generated to any antigen-specific oligoclonally expanded T cell subpopulation encountered in animals (e.g., humans, other mammals, and birds) in response to given antigenic challenges. These T cell subsets include those T cells oligoclonally expanded in response to an immunodominant component of the antigen in multiple individuals. For example, an antigen of interest may be administered to an animal, and the oligoclonally expanded T cell subsets that are generated by this administration may be isolated and used for the production of antibodies as described herein.

TABLE 1

Citations for T cell receptors that may be used to generate antibodies for clinical applications involving the indicated disease or condition

| Disease/Condition | Citation |
|---|---|
| Multiple Sclerosis | Wucherpfennig et al., J. Exp. Med. 175: 993-1002 (1992). |
| Environmental Pathogens/ Promotion of Oral Tolerance | Blumberg et al., J. Immunol. 150: 5144-5153 (1993). |
| Ulcerative Colitis | Chott et al., J. Immunol 156: 3024: 3035, (1996). |
| Ulcerative Colitis | Shigematsu et al., J. Clin. Lab. Immunol. 48: 177-186 (1996). |
| Chronic Inflammatory Bowel Disease | Probert et al., J. Immunol. 157: 3183-3191 (1996). |
| Antigens | Porcelli et al., J. Exp. Med. 178: 1-16 (1993). |
| Rheumatoid Arthritis | Fitzgerald et al., J. Immunol. 154: 3538-3547 (1995). |
| Rheumatoid Arthritis | Sottini et al., J. Autoimmun. 6: 621-637 (1993). |
| Rheumatoid Arthritis | Hingorani et al., J. Immunol. 156: 852-858 (1996). |
| Polymyositis | Bender et al., J. Exp. Med. 181: 1863-1868 (1995). |
| Giant Cell Arteritis | Grunewald et al., Arthritis Rheum. 37: 1221-1227 (1994). |
| Bone Marrow Transplantation | Gorochov et al., Blood 83: 587-595 (1994). |
| Systemic Sclerosis | Kuwana et al., J. Immunol. 158: 485-491 (1997). |
| Human Leishmaniasis | Uyemura et al., J. Immunol. 151: 7095-7104 (1993). |
| B Chronic Lymphocytic Leukemia | Farace et al., J. Immunol. 153: 4281-4290 (1994). |
| Multiple Myeloma and Paraproteinemia | Moss et al., Blood 87: 3297-3306 (1996). |

EXAMPLE 2

Isolation and Expansion of Human Invariant T Cells with Monoclonal Antibody

Figures 4A, 4B:
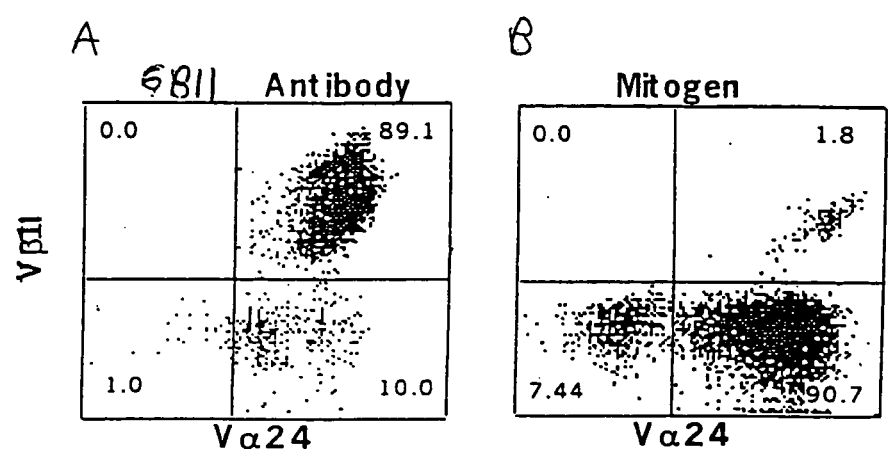
FIGS. 4A and 4B are graphs showing the expansion of V$\alpha$24 sorted cells that were cultured for three weeks with plate bound 6B11 anti-CDR3-loop monoclonal antibody or PHA, respectively.

FIG. 4 demonstrates that plate bound 6B11 monoclonal antibody can be used to achieve selective expansion of invariant T cells. Analysis of more than 20 clones and 15 lines derived from 15 healthy donors using 6B11 in this way has produced entirely consistent results: 100% of these were Vα24+Vβ11+CD161+, highly CD1d-reactive, high IL-4 producers, and modest IFN-γ producers (Table 2). This result further demonstrate the specificity of these monoclonal antibodies and their use as a more definitive and single color alternative that does not require autologous APCs, which would be undesirable in the setting of a clinical trial.

TABLE 2

Percentage of cell expressing invariant NK T cell markers and producing cytokines after expansion of T cell lines or T cell clones with the 6B11 antibody.

| Donors | Cells | Vα24+ | Vβ11+ | CD161+ | CD1d-reactive | IL-4 | IFN-γ |
|---|---|---|---|---|---|---|---|
| Tcell lines 12 | 15 | 10-100 | 10-100 | 10-100 | 100 | 100 | 10-100 |
| Tcell clones 3 | 20 | 100 | 100 | 100 | 100 | 100 | 65 |

Figures 6A, 6B, 6C:
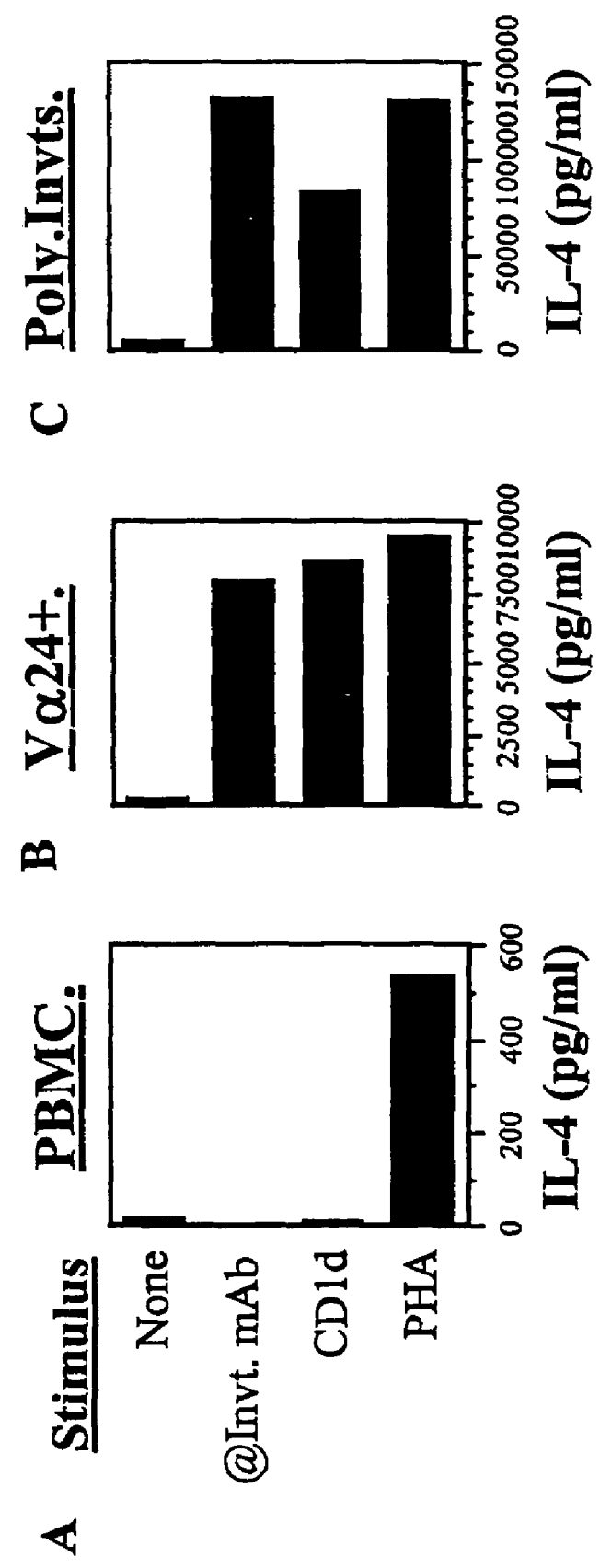
FIGS. 6A-6C are graphs showing IL-4 production by bulk peripheral blood mononuclear cells, V$\alpha$24$^+$, and polyclonal ('poly.') invariant T cells, respectively. These cells were expanded with $\alpha$-GalCer and then stimulated with either buffer, plate bound 6B11 antibody, co-cultured with Hela/CD1d transfectants, or PHA. The amount of secreted IL-4 was determined using standard ELISA analysis.

The monoclonal antibody 6B11+ was also used alone (2 donors, 10 clones) or paired with the anti-Vα24 antibody (9 donors, 87 clones) to clone additional invariant T cells by single cell sorting. All the clones were confirmed to be invariant CD1d-restricted T cells. All of these clones also contained the invariant TCR-α chain, based on sequence analysis of the TCR-α chain. Additionally, all of the clones were CD1d restricted (Exley et al, J. Exp. Med. 186:109, 1997). In some donors there are very small numbers of 6B11+ and CD3+ T cells. The two donors for whom only the 6B11 antibody was used for T cell purification did not have this population. One of these donors had 0.01% Vα24+Vβ11+ cells in their peripheral blood. The generation of 6/6 Vα24+ Vβ11+ CD1d-restricted T cells from this individual highlights the specificity of 6B11. The probability of 6/6 Vα24+Vβ11+ clones based on chance is $(10^{-4})^6$. As illustrated in FIGS. 6A-6C, the 6B11 antibody also stimulates secretion of IL-4 from CD1d-restricted T cell lines.

Additionally, use of the 6B11 antibody in either a FACS sort or magnetic bead immunoaffinity purification step followed by expansion in the presence of a mitogen resulted in the isolation of invariant NK T cells (see, for example, FIGS. 8, 9, 10A-10H, and 11A-11F). Starting with PBMC in which approximately 0.05% of the lymphocytes in PBMC are invariant T cells, approximately 5-30% of the purified and expanded cells were invariant T cells.

The 6B11 antibody has recognized invariant NK T cell clones and lines from all the donors that have been tested, including over 100 subjects from various ethnicities and age groups (see, for example, FIGS. 8B-8I). This antibody has also recognized invariant NK T cells in both male and female subjects, including subjects diagnosed with cancer and subjects not diagnosed with cancer. These results demonstrate that the ability of the 6B11 antibody to recognize invariant NK T cells in not limited to a particular population of patients.

Figures 7A, 7B, 7C:
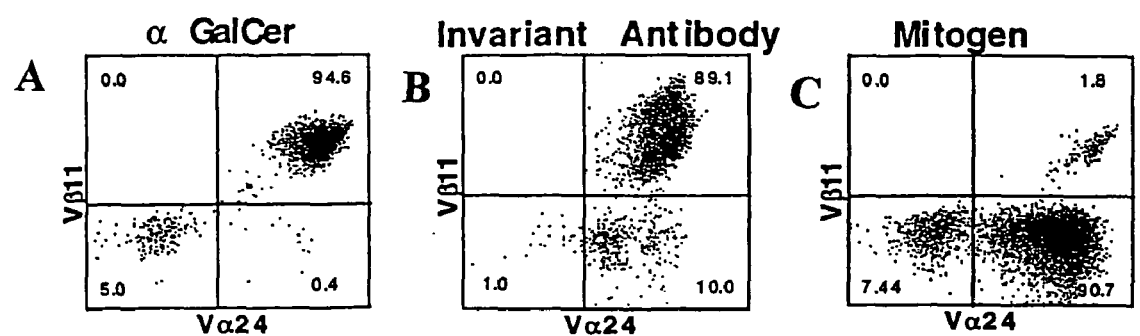
FIGS. 7A-7C are graphs showing the comparable expansion of phenotypically and functionally identical invariant NK T cells from the same healthy donor sample by 6B11 and $\alpha$-GalCer. V$\alpha$24 'MoFlo' sorted cells were expanded with $\alpha$-GalCer pulsed autologous dendritic cells, 6B11 monoclonal antibody, or mitogen (PHA) for an approximately four week expansion with IL-2 alone.
Figures 8A, 8B, 8C:
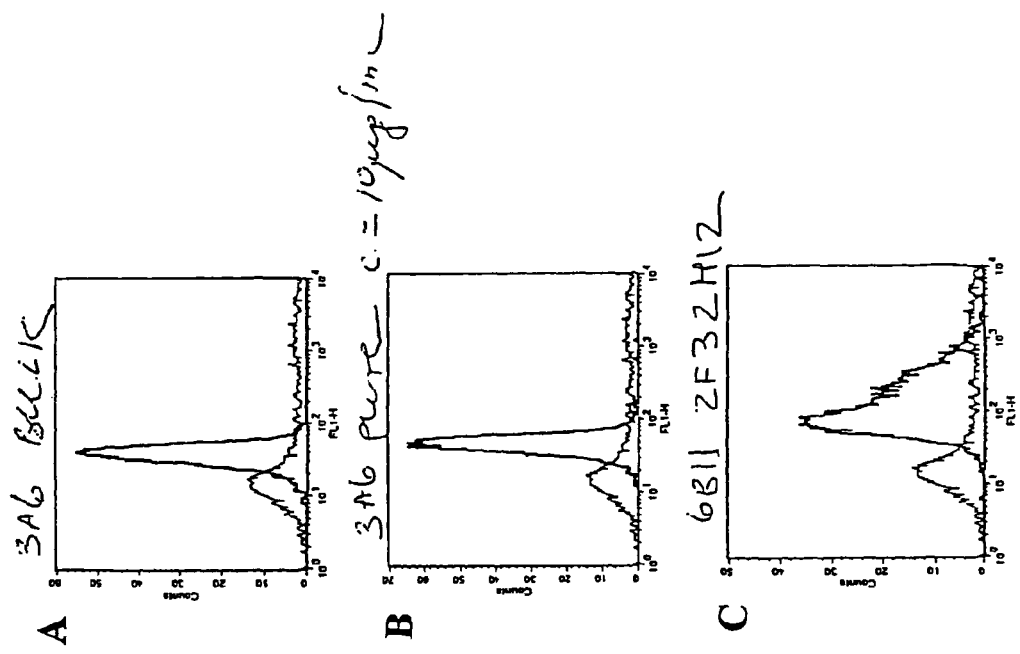
FIG. 8A is a graph showing the recognition of bulk T cells from a peripheral blood sample by the 3A6 antibody.
FIGS. 8B, 8C, and 8E-8I are graphs showing the recognition of invariant NK T cell clones and lines by the 3A6, 6B11, or isotype control antibodies. These invariant NK T cell clones and lines were purified using the anti-V$\alpha$24 monoclonal antibody followed by expansion using alpha-GalCer. For FIGS. 8B-8I, the same "MT" cell line was analyzed. This indirect (1-color) FACS analysis using the 3A6 or 6B11 antibody and anti-mIg-FITC shows specific recognition of pure human invariant NK T cell clones and lines compared to control T cells.
Figures 8D, 8E, 8F, 8G, 8H, 8I:
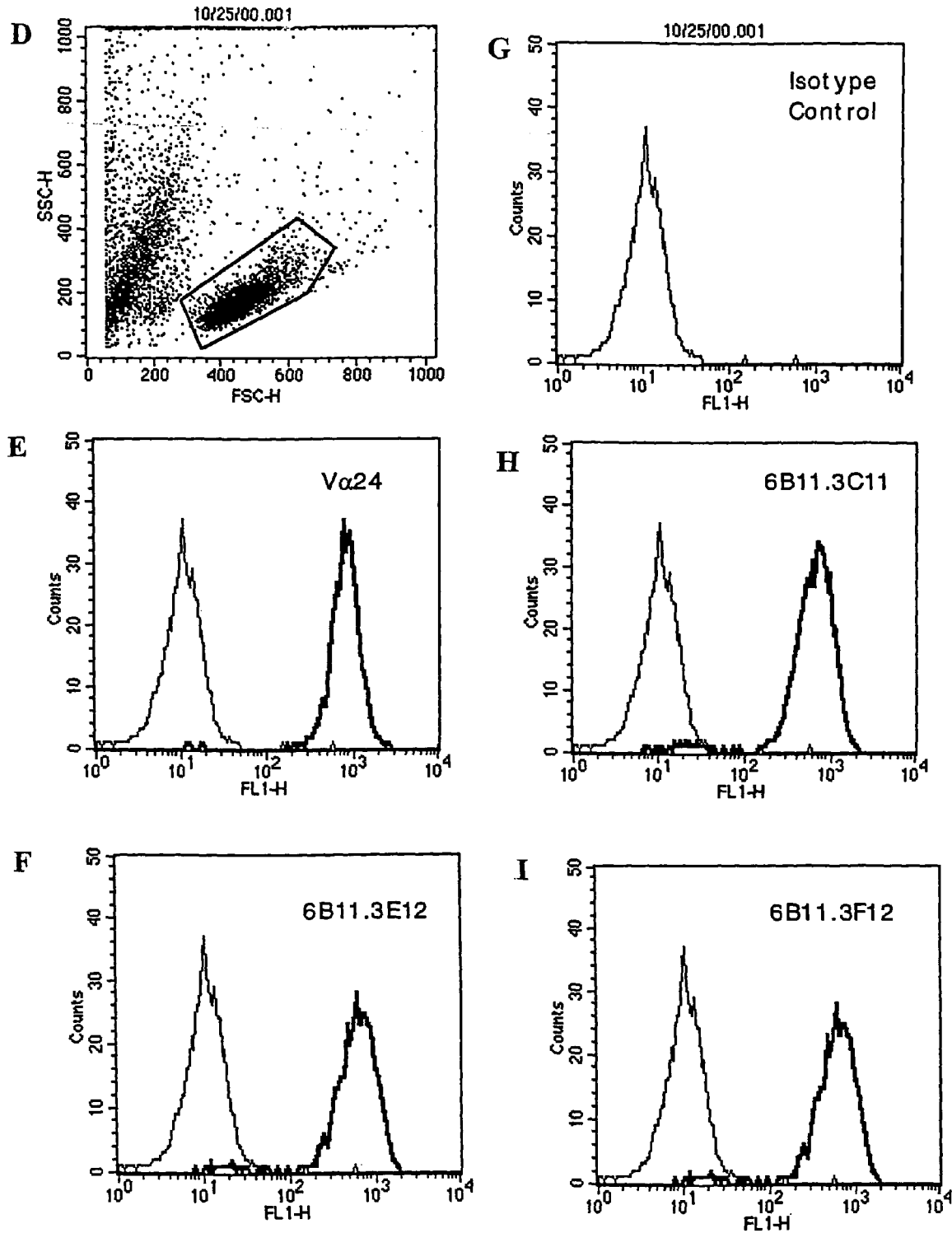
FIG. 8D is a graph of the forward (FSC) and side (SSC) scatter of cells showing the gating for the lymphoid cells that were analyzed using the 6B11, 3A6, or control antibody.
Figure 9:
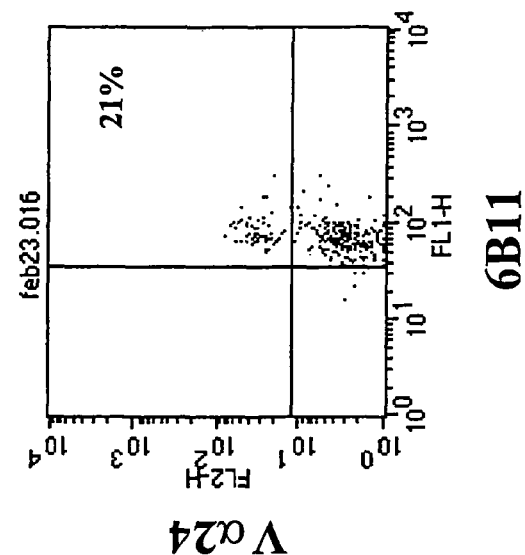
FIG. 9 is a graph showing the FACS analysis of invariant NK T cell lines from whole peripheral blood mononuclear cells (PBMC) of a healthy donor. These cells were sorted with 6B11-FITC by MoFlo FACS and expanded for about six weeks prior to 2-color FACS analysis. After expansion, 21% of the cells were Vα24+, compared to an original ~0.1%. These results are also summarized in FIGS. 12-17.
Figures 10A, 10B, 10C, 10D, 10E, 10F, 10G, 10H:
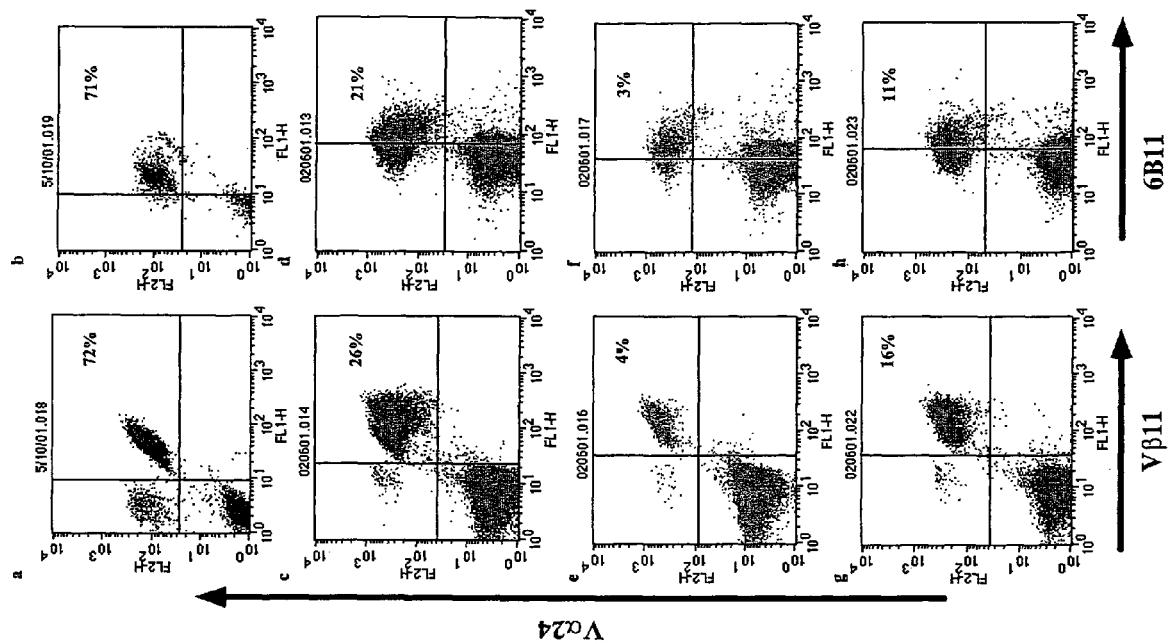
FIGS. 10A-10H are graphs showing the FACs analysis of invariant NK T cell lines from 6B11 antibody magnetic bead sorting. Invariant NK T cells from whole PBMC of a healthy donor were sorted with 6B11 by Dynal or Miltenyi magnetic bead immunoaffinity purification from whole PBMC and expanded for about six weeks prior to 2-color FACS analysis. These results are also summarized in FIGS. 12-17.
Figures 11A, 11B, 11C, 11D, 11E, 11F:
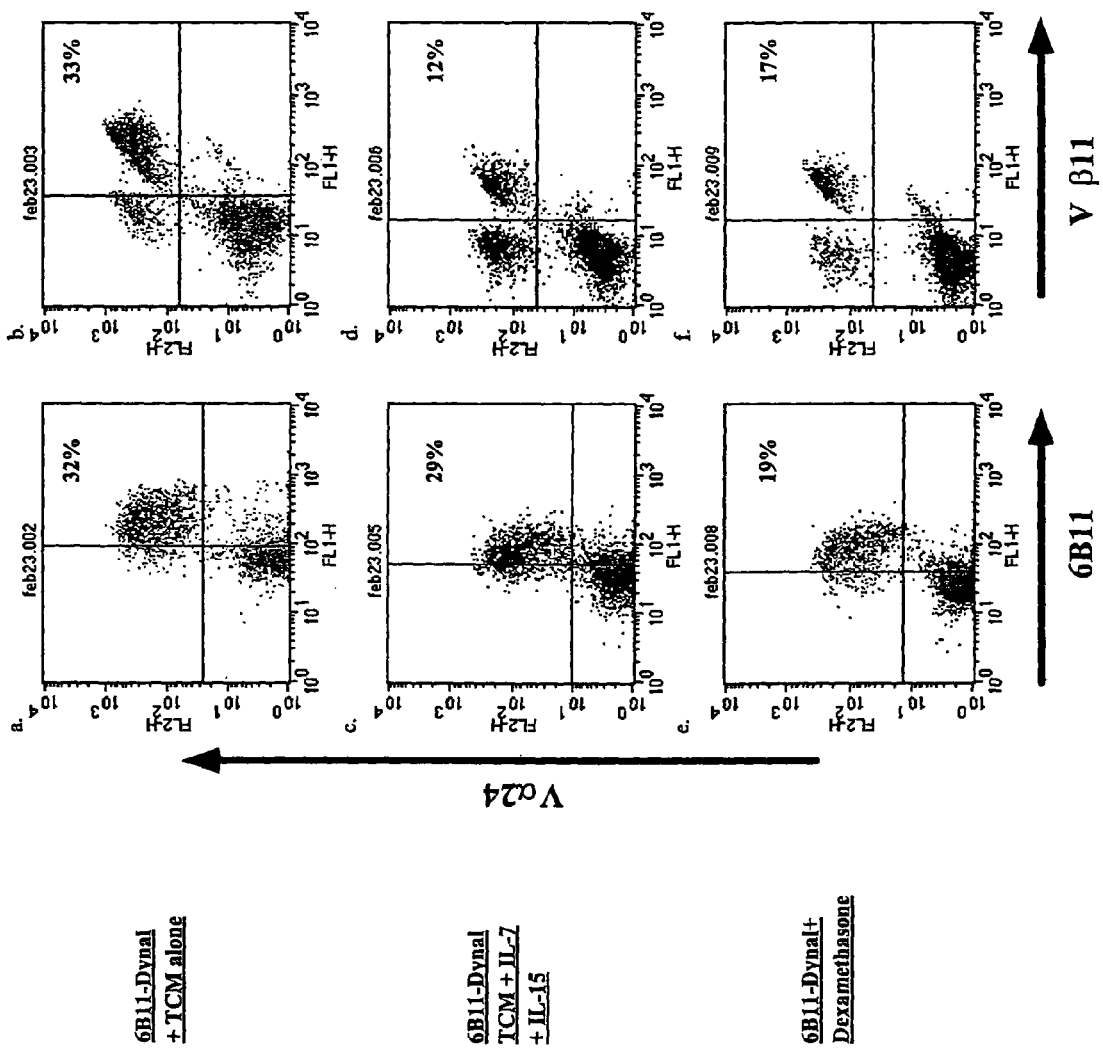
FIGS. 11A-11F are graphs showing the FACs analysis of invariant NK T cell lines from 6B11 antibody magnetic bead sorting. Invariant NK T cells from whole PBMC of a healthy donor were sorted with 6B11 by Dynal magnetic bead immunoaffinity purification and treated as shown from whole PBMC and expanded for about six weeks prior to 2-color FACS analysis. These results are also summarized in FIGS. 12-17.

The ability of the 6B11 antibody to expand invariant NK T cells was compared to that of α-GalCer pulsed autologous dendritic cells. For this comparison, Vα24 'MoFlo' sorted cells were expanded with α-GalCer pulsed autologous dendritic cells, 6B11 monoclonal antibody, or mitogen (PHA) for an approximately four weeks expansion in the presence of IL-2. As illustrated in FIGS. 7A-7C, the expansion of invariant NK T cells using the 6B11 antibody was similar to that achieved using α-GalCer. However, expansion using the 6B11 antibody has the advantage of not requiring APCs.

EXAMPLE 3

Exemplary Methods for the Isolation and Expansion of T Cells of Interest

For the purification of a T cell subpopulation of interest, a positive and/or negative selection step may be performed.

Examples of antibodies that may be used in a positive selection step include the 6B11, 3A6, anti-Vα24, anti-Vβ11, and anti-CD161 antibodies.

T cells of interest may also be enriched using a negative selection step that removes some of the undesired T cells or that removes other contaminants from a sample. For example, an anti-CD8 antibody and/or an anti-CD4 antibody may be used to enrich a sample for invariant NK T cells. A negative selection step may be performed prior to, concurrent with, or subsequent to a positive selection step.

A positive and/or negative selection step may be performed prior to or after a T cell expansion step. In one possible method, the T cells of interest are purified first and then selectively expanded. In another possible method, expanded T cells are purified using a high capacity column (e.g, $10^{10}$ expanded cancer patient peripheral blood mononuclear cells (PBMC) could yield $10^6$ invariant NK T cells after large scale Miltenyi or other column purification steps).

Examples of possible positive purification steps are listed below. These methods may be used with antibodies of the invention that are reactive with any T cell subpopulation of interest.

Exemplary FACS Procedure

PBMC or another tissue source is blocked with autologous serum at 4° C. An antibody reactive with invariant T cells (e.g., 6B11 or 3A6 antibody) is added at a ratio of about 1-10 μg antibody/$10^{7-8}$ PBMC and incubated for 20 minutes at 4° C. The antibody used in this method may be directly labeled with a conjugate such as FITC or biotin, or the antibody may be indirectly labeled with second reagent (e.g., anti-IgG-Fluorochrome or streptavidin-Fluorochrome). One or more other antibodies labeled with different fluorophores may also be added (FIGS. 7A-7C and 9). The solution of cells and antibodies is then washed using PBS or any other physiological buffer to remove unbound antibody.

If desired, the settings of the FACS cell sorter may be adjusted using either a positive (e.g., general anti-T cell antibody) or negative control antibody. The sample of interest may be analyzed at a rate of approximately 100 million cells per hour using a high speed FACS sorter (e.g., 'MoFlo' FACS sorter). The purified T cells may be expanded in T cell media [e.g., 10% Fetal Bovine or human autologous or AB pooled serum in RPMI-1640 or equivalent media supplemented with buffer (e.g. Hepes), glutamine, and antibiotic (e.g., gentamicin)] in the presence of a mitogen such as PHA, an anti-CD3 antibody, the 6B11 antibody, the 3A6 antibody, and/or α-Gal- Cer antigenic stimulus CD3 monoclonal antibody (Exley et al. 1997 and 1998, supra; Wilson et al., Nature 391:177, 1998). The antibody may be in solution or plate bound. Irradiated autologous feeders and IL-2 (10-100 U/ml) may also be added immediately or added at any time point during expansion. IL-7 (~1-10 ng/ml) and/or IL-15 (~1-10 ng/ml) may increase invariant NK T cells yields (e.g. Wilson et al. 1998, supra; van der Vliet et al. Journal of Immunological Methods 247:61-72, 2000). Dexamethasone or a related selective immune suppressive agent (~1 μM) may preferentially enhance the growth of invariant NK T cells while inhibiting growth of conventional T cells (e.g. Milner et al., J. Immunol. 163(5):2522-25229, 1999). The media is replaced about twice a week with fresh media. During or subsequent to expansion (e.g., 2-4 weeks after expansion has begun), the T cells may be phenotypically analyzed by FACS. This analysis may be performed by staining with 6B11, anti-Vα24, anti-Vβ11, anti-CD4, anti-CD8αβ, or anti-CD161 antibodies.

Exemplary Magnetic Bead Procedure

PBMC or another tissue source is blocked with 1-10% autologous serum by mixing at 4° C. in PBS or other physiological buffer. One or more antibodies that are reactive with invariant T cells (e.g., 6B11 or 3A6 antibody) is added at a ratio of about 1-10 μg monoclonal antibody/$10^{7-8}$ PBMC is incubated for 20 minutes at 4° C. The antibody used in this method may be directly labeled with a conjugate such as FITC or biotin or the antibody may be indirectly labeled with second reagent (e.g., anti-IgG-Fluorochrome or streptavidin-Fluorochrome). One or more other antibodies labeled with different fluorophores may also be added (FIGS. 7A-7C and 9). The solution of cells and antibodies is then washed using PBS or any other physiological buffer. Magnetic beads, such as ~10-100 μl Miltenyi MACS Microbeads Anti-mouse IgG #484 or MACS Steptavidin Microbeads #481 per $10^{7-8}$ PBMC; $10^{5-7}$ Dynal Anti-IgG #M450 beads per $10^{7-8}$ PBMC are added and the solution is mix at 4° C. The beads are isolated using magnets and then washed according to the manufacturers' recommendations (e.g., using Miltenyi MS type separation columns such as product number 130-042-201 and MACS multistand, or Dynal beads directly in tubes on Dynal or comparable magnets). The washed, purified cells are placed into multi-wells with T cell media [10% Fetal Bovine or human autologous or AB pooled serum in RPMI-1640 or equivalent media supplemented with buffer (e.g. Hepes), glutamine, and antibiotic (e.g. gentamicin)]. The cells may be expanded using a monoclonal antibody that is directly bound to the beads or in solution. Additionally or alternatively, the cells may be expanded using media that is supplemented with a mitogen such as PHA, an anti-CD3 antibody, the 6B11 antibody, the 3A6 antibody, or α-GalCer antigenic stimulus CD3 monoclonal antibody. The antibody may be in solution or bound to a plate, bead, or other solid surface. As described above, various other reagents such as IL-7, IL-15, and dexamethasone may improve product yield and/or purity. The expanded T cells may be phenotypically analyzed as described above.

EXAMPLE 4

Magnetic Bead Purification of Invariant T Cells

FIGS. 10A-17 illustrate the ability of these magnetic bead purification methods to generate a large number of purified invariant T cells. In particular, the 6B11 antibody was bound to either (1) Dynal superparamagnetic, polystyrene beads with affinity purified goat anti-mouse IgG covalently bound to the surface (Dynabeads® M-450 goat anti-mouse IgG, Product Number 110.05) or (2) Milenyi MACS colloidal super-paramagnetic microbeads conjugated to goat anti-mouse IgG (Product Number 484-02, Miltenyi Biotec) according to the manufacturer's instructions (Dynabeads® M-450 goat anti-mouse IgG package insert; MACS goat anti-mouse IgG microbead instructions). PBMC cells were enriched for invariant T cells by purification using 6B11-Dynal or 6B11-Milenyi beads. The purified cells were than expanded for four to eight weeks under various conditions. For example, the T cells were expanded in the presence of one or more of the following as indicated in FIGS. 12-17: PHA, the 6B11 antibody, IL-5, IL-7, allogenic APC, and autologous APC. The "PBMC" column represents PBMC cells that were not sorted prior to expansion. The "Dynal @ 40" column represents PBMC cells that were purified using 6B11-Dynal beads prior to expansion. The "Milenyi @ 20" column represents PBMC cells that were sorted using 6B11-Milenyi beads prior to expansion.

In the experiments described in FIGS. 12-17, the addition of IL-7 and IL-15 increased the yield of invariant T cells. At the concentrations tested, IL-7, IL-15, and dexamethasone did not increase the purity of invariant T cells. Expansion using α-GalCer after expansion using 6B11 did not improve the purity of invariant T cells but did increase the number of invariant T cells. Neither limiting (6B11$^+$ CD161) or (CD3$^+$ CD161) increased the yield of invariant NK T cells (FIGS. 12-17).

Figure 18:
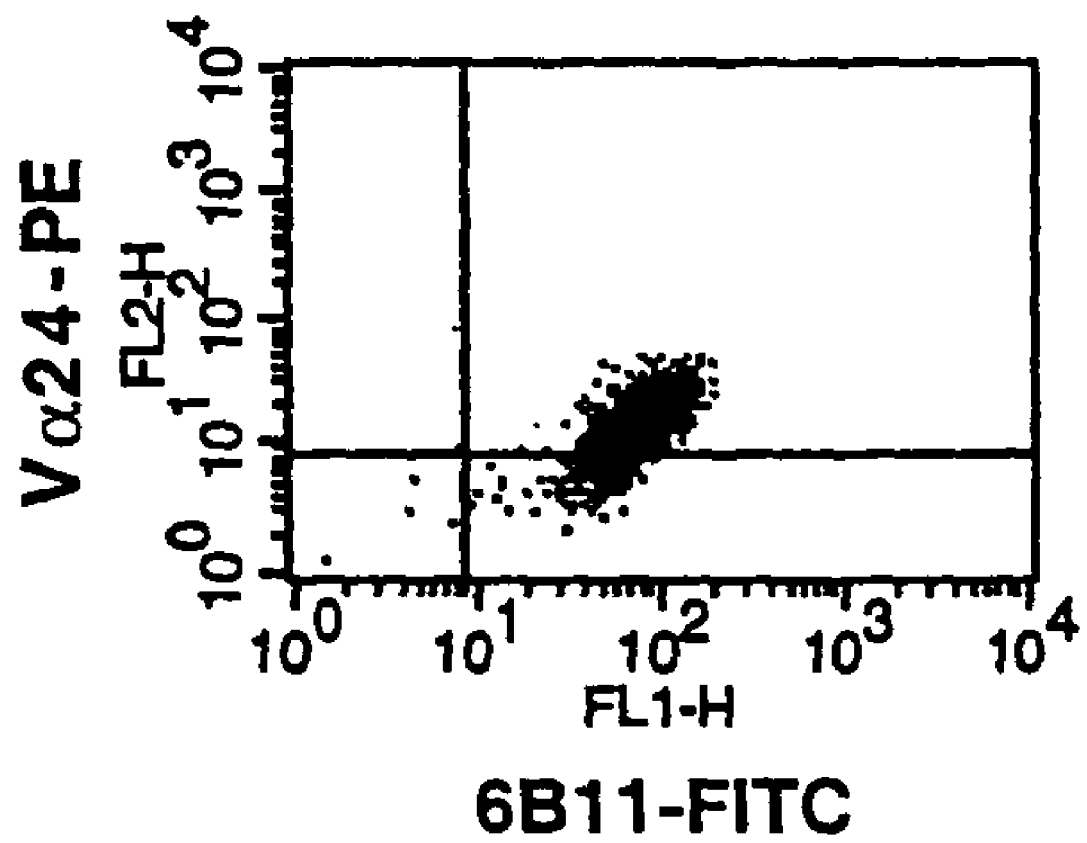
FIG. 18 is graph showing the FACs analysis of a T cell line purified using the biotinylated 6B11 antibody and streptavidin conjugated magnetic beads.

Invariant T cells were also purified using biotinylated 6B11. For this procedure, ficoll purified PBLs were incubated with 6B11'-biotin. The cells were then washed to remove unbound antibody and incubated with streptavidin conjugated to Miltenyi microspheres. The 6B11$^+$ cells were isolated by magnetic bead selection according to the manufacturer's specifications. A total of 6 lines were generated using the 6B11 antibody in combination with IL-2 and IL-7. Three of the six lines were expanded and had a surface phenotype consistent with invariant Vα24$^+$ CD1d-restricted T cells. The lines varied from 76%-99% invariant after expansion. A FACS profile of the pure line is shown in FIG. 18. This successful cloning and expansion of invariant T cells demonstrates that 6B11 can be used in combination with the MACS™ technology to isolate CD1d-restricted T cells directly from blood without the need for FACS-based cloning protocols and irradiated feeders.

EXAMPLE 5

Ex Vivo or In Vivo Cytokine Treatment to Alter the Th1/Th2/Immune Deviation Response Ratio of NK T Cells While not meant to limit the invention to a particular theory, a working hypothesis is that NK T cells, CD1d-reactive T cells, or JαQ$^+$ T cells producing high levels of IL-4 (possibly in conjunction with other "Th2" cytokines) will bias toward Th2 immune responses, while high IL-12 (induced from APCs by activated CD1d-reactive T cells) and/or IFN-γ (produced by the T cells themselves) relative to IL-4 will drive (or at least be a marker of invariant T cells that will drive) immune responses against tumors or infectious pathogens.

NK T cells, CD1d-reactive T cells, or JαQ$^+$ T cells may be biased towards Th1-like NK or lymphokine-activated killer (LAK)-like cytotoxicity of invariant T cells, as well as, IFN-γ production to potentially augment their in vivo anti-tumor or anti-pathogen activity. Feasibility of this approach is demonstrated by the finding that initial IL-4 bias of invariant T cells can be altered by ex vivo expansion in IL-12, which results in markedly higher levels of IFN-γ relative to IL-4, making this a promising straightforward method for the generation of Th1 biased invariant T cells (Table 3). Confirmatory results showing that culturing in IL-12 augments both IFN-γ production and, significantly, NK/LAK-like cytotoxicity of invariant T cells have recently been published (van der Vliet et al., Immunology 98:557-63, 1999).

TABLE 3

Enhanced IFN-γ production by invariant NK T cells incubated with IL-12.

|  |  | Proliferation | IL-4 | IFN-γ | IFN-γ/IL-4 |
| --- | --- | --- | --- | --- | --- |
| line 1 | no IL-12 | 36239 | 1.4 | 60.4 | 43.1 |
|  | +IL-12 | 56593 | 4.8 | >500 | >100 |
| line 2 | no IL-12 | 21858 | 1.1 | 18.1 | 16.5 |
|  | +IL-12 | 42499 | 1.6 | 331.8 | 207 |

CD1d-reactive Vα24+Vβ11+ T cell lines were established with or without IL-12 and stimulated with limiting plate-bound anti-CD3 and excess CD161 antibody to specifically stimulate invariant NK T cells.

Thus, invariant T cells can be re-polarized to the Th1 phenotype by culturing in 0.3 nM IL-12 (Exley et al., supra (1998)) during ex vivo expansion with an antibody of the present invention. IL-15, IL-18, and type 1 INFs are also known to enhance Th1 polarization of human T cells. Other cytokines or combinations of cytokines that may bias NK T cells, CD1d-reactive T cells, or JαQ+ T cells towards Th1, Th2, or immune deviation responses include IL-2, IL-4, IL-7, IL-8, IL-10, IL-12, IL-13, IL-15, IL-18, IFN-α/β, IFN-γ, and GM-CSF. The Th2 response may be desirable for the prevention or treatment of an autoimmune disease. Alternatively, for the maintenance of pregnancy, cytokines may be used to bias NK T cells, CD1d-reactive T cells, or JαQ+ T cells towards immune deviation responses instead of Th1 or Th2 responses. Anti-IL-4 or anti-IL-12 antibodies which bind the cytokines produced by the T cells during expansion may also favor the immune deviation or Th2 response of these T cells. These cytokines may present during the entire time period for T cell expansion or may be present for only a portion of the time period for T cell expansion, such as during the last few days of T cell expansion.

After expansion in the presence of one or more of these cytokines, the T cells may be functionally tested for secretion of L-4, IL-10, GM-CSF, and IFN-γ. The regulation of cytotoxicity against CD1d+ (C1R, CD1d), 'NK' targets (JY, K562, 721.221, and YAC-1), or LAK targets by cytokine supplementation may also be determined (Exley et al., supra (1997); Exley et al., J. supra, (1998)).

Alternatively, one or more of the cytokines may be administered in vivo to patients before, during, or after re-introduction of the ex vivo expanded NK T cells, CD1d-reactive T cells, or JαQ+ T cells to bias the re-introduced cells towards Th1, Th2, or immune deviation responses.

EXAMPLE 6

Figure 5A:
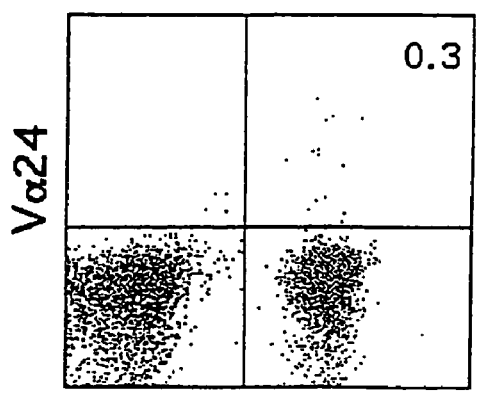
FIGS. 5A and 5B are graphs showing the FACS analysis of invariant NK T cells in a patient before and during IL-12 treatment, respectively. Peripheral blood of a patient with advanced renal cell cancer was analyzed for CD3$^+$ V$\alpha$24$^+$ cells immediately before IL-12 therapy and at completion of the first 6 week cycle. Comparable low fractions of V$\alpha$24$^+$ T cells, with no significant increase after treatment, have been observed in all cases (n=10).
Figure 5B:
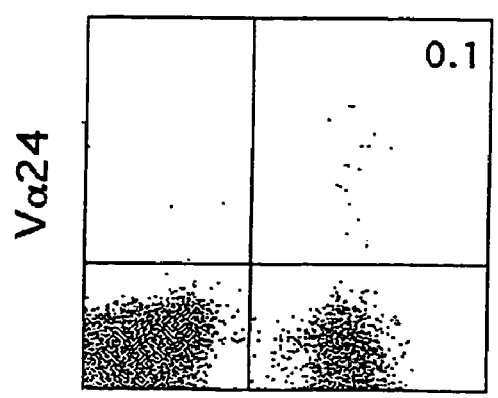

Determination of the Change in Number or Activity of Invariant T Cells Induced by a Therapy for the Treatment or Prevention of Disease The monoclonal antibodies of the present invention may be used in a sensitive and specific method to determine whether a therapy for the treatment or prevention of a disease increases the number and/or preferentially binds or modulates the function of invariant T cells. In contrast, the previously used analysis to determine the effect of in vivo IL-12 anti-cancer treatment on invariant T cells has been performed with the relatively insensitive method of flow cytometry with Vα24 monoclonal antibody, in some cases in conjunction with Vβ11 monoclonal antibody, which has not detected an increase in invariant T cells (n=10) (FIG. 5). Given the low numbers of invariant T cells in normal donors and the even lower numbers that have been found in advanced cancer patients, the method described below may be used to more accurately determine the effect of IL-12 treatment, or other treatments, on invariant T cells. Effects of cumulative doses on invariant T cells may be determined by performing this analysis after each dose.

Patients can serve as their own controls in these experiments. Approximately 20 ml of peripheral blood can be obtained from patients before treatment is initiated and subsequently during treatment. A small aliquot of these cells (approximately $10^6$ cells) can be used for synthesis of cDNA, corresponding to mRNA encoding the TCR-α chain, and PCR amplification using Vα24 and Cα primers to determine the frequency of cells expressing the invariant TCR-α chain. The fraction of invariant TCR in total population may be determined by calibration with an invariant T cell clone diluted in series into a control T cell clone.

As an alternative to the above PCR analysis, flow cytometry may be used to determine the frequency and number of invariant T cells. Because of the low numbers involved, particularly in cancer patients, minimal numbers of conditions and large numbers of analyzed events (100,000) are used for each sample. The anti-CDR3-loop monoclonal antibodies 6B11 and/or 3A6, which have been successfully conjugated to fluorescein using standard methods, may be used in a simple 1- or 2-color FACS analysis. Additionally, multi-color FACS may be used for simultaneous analysis of the invariant TCR-α chain using one or more monoclonal antibodies of the present invention and antibodies for other invariant T cell markers (Vα24, CD4, CD8, CD56, CD161, Vβ11). These results for patient samples before and after treatment may be compared to determine the effect of the treatment on invariant T cell numbers. Cytokine production and cytotoxicity by the activated cells may be assessed, as described in Example 5. The results may be normalized for the number of invariant T cells, allowing direct comparisons for patients before and after treatment.

Alternatively, one round of expansion may be required for quantitation. The patient sample may be directly subjected to monoclonal antibody expansion or the sample may be enriched for invariant T cells by high speed FACS sorting or magnetic bead immunoaffinity purification prior to expansion, using standard procedures. For enrichment by FACS sorting, one-color sorting using anti-Vα,24, 6B11, or 3A6 or 2-color sorting using 6B11 or 3A6 and anti-Vα24, Vβ11, or CD161 may be performed. Alternatively, for enrichment by immunoaffinity purification, one or more negative or positive selections may be conducted. For example, a negative depletion may be used to remove monocytes and/or B cells. Then a positive selection could be performed using the Vα24 monoclonal antibody and/or an anti-CDR3-loop monoclonal antibody.

The cells may be cultured with a plate bound or soluble anti-CDR3-loop monoclonal antibody (6B11 or 3A6) or with antigen pulsed autologous or allogenic APCs. Although single round expansions of T cells are widely representative of initial proportions, the cells may alternatively be cultured for approximately one week prior to expansion to rest activated cells which may respond poorly to expansion compared to resting cells.

Approximately 3-4 weeks after primary stimulation, a portion of the cells may be analyzed by flow cytometry with Vα24, Vβ11, and 6B11 monoclonal antibodies to determine the fraction of invariant T cells. Cytokine production and cytotoxicity normalized for the number of invariant T cells may be compared for patients before and after treatment, as described above. Moreover, the PCR analysis or FACS analysis of the cells before the primary stimulation may be used to determine to what extent increased recovery of invariant T cells (after the primary stimulation) reflects expansion in vivo due to the treatment versus increased response to ex vivo stimulation.

This analysis carried out on 8-10 patients (with on average two time points post treatment) should be adequate to determine whether the treatment has the potential to increase the number or modulate the activity of invariant T cells. If such positive effects on invariant T cells are demonstrated, then further studies correlating invariant T cell responses with dose, schedule, and other immunological functions may be performed. For example, changes in invariant T cell numbers and/or responses may be correlated to key immune parameters including serum IFN-γ, TNFs, and IL-15; expression of IL-12 and other Th1 cytokine and chemokine receptors; and changes in T cell, myeloid, and other cell markers (Fas, FasL, Lymphotoxin-β, CD3, CD4, CD8, LFA-1, CD80, CD86, CD161).

This method for determining the change in the number or activity of invariant T cells may also be applied to NK T cells, CD1d-reactive T cells, or JαQ$^+$ T cells. If a pre-enrichment step is required to quantitate these T cells, any antibody that binds these cells, including antibodies of the present invention, may be used in the initial purification step or a negative selection may be used to remove cells that are not T cells or cells that are not NK T cells, CD1 d-reactive T cells, or JαQ$^+$ T cells.

EXAMPLE 7

Expansion and Re-Introduction of Ex Vivo Expanded Invariant T Cells into Mammals Invariant T cells from a peripheral blood sample (20 ml or from the product of leukopheresis) from a mammal may be enriched prior to ex vivo expansion using FACS sorting or immunoaffinity purification or expanded directly using an antibody of the present invention, as described in the previous examples. As mentioned in Example 5, the cells may be expanded in the presence of a cytokine to bias them towards Th1, Th2, or immune deviation responses. Additionally, IL-2, IL-7, or a mitogen may be added to stimulate cell expansion. If necessary, a secondary ex vivo expansion, possibly after a second enrichment step, may be conducted under conditions used for the primary expansion to increase both cell number and purity. After stimulation, the cells may be assayed for purity and cytokine production and cytotoxicity as described above. It should be noted that we and others have been able to establish long term human invariant T cell lines and clones from normal donors by multiple rounds of stimulation; thus, similar results are expect from other patients. Desirably at least $10^6$, more desirably at least $10^8$, and most desirably at least $10^9$ invariant T cells are obtained after expansion. Desirably, the invariant T cells are at least 60%, 80, or 90% pure, based on the presence of Vα24, Vβ11, and CD161 invariant T cell markers, and maintain the production of IFNγ and cytotoxicity against CD1d$^+$ and 'NK' targets.

If secondary stimulations do not yield adequate cell numbers, then additional rounds of stimulation may be used. Alternatively, the number of starting cells may be increased by using larger blood samples or through leukopheresis. In this case, an initial enrichment of invariant T cells may be performed by positive selection using the Vα24 or 6B11 monoclonal antibody conjugated to beads, as described above. To increase purity, the invariant T cells may also be purified by FACS or antibody conjugated to beads prior to re-infusion. Additionally, the therapeutic potential of cellular reinfusion of expanded polyclonal invariant T cell lines may be compared to that of expanded invariant T cell clones, or pools thereof.

It is not intended that the administration of ex vivo expanded invariant T cells be limited to a particular mode of administration, dosage, or frequency of dosing; the present mode contemplates all modes of administration, including intramuscular, intravenous, intraarticular, intralesional, subcutaneous, or any other route sufficient to provide a dose adequate to prevent or treat an autoimmune disease, viral infection, bacterial infection, parasitic infection, infection by a eukaryotic pathogen, allergy, asthma, inflammatory condition, host versus graft disease, spontaneous abortion, pregnancy, or cancer. Desirably, the cells are re-introduced into the mammal from which the blood sample was taken. It is also contemplated that the cells may be administered to a different mammal. The cells may be administered to the mammal in a single dose or multiple doses. When multiple doses are administered, the doses may be separated from one another by, for example, one week to one month. As mentioned in Example 5, one or more cytokines may also be administered before, during, or after administration of the cells to bias them towards Th1, Th2, or immune deviation responses. It is to be understood that for any particular subject, specific dosage regimes should be adjusted over time according to the individual need and the professional judgement of the person administering or supervising the administration of the compositions. Additionally, the T cells may be re-introduced as resting or activated cells, depending on the application. Resting cells would require in vivo activation.

EXAMPLE 8

Expansion and Re-Introduction of Ex Vivo Expanded NK T Cells, CD1D-Reactive T Cells, or JαQ$^+$ T Cells into Mammals Other NK T cells, CD1d-reactive T cells, or JαQ$^+$ T cells may be expanded ex vivo as described in Example 7. This method may be modified by expanding NK T cells, CD1d-reactive T cells, or JαQ$^+$ T cells from bone marrow, liver, umbilical cord, or other samples. Desirably, the sample contains a greater percentage of CD1d-reactive noninvariant T cells than peripheral blood. Additionally, costimulation (using CD1d, lipids, other antigens, or antibodies) or inhibition of costimulation may be used to expand a desired subpopulation of T cells. For example, stimulation of CD28 may favor the expansion of CD1d reactive noninvariant T cells over invariant T cells. Soluble anti-CD161 antibodies that block CD161 stimulation may also favor the expansion of noninvariant T cells which are less dependent on CD161 stimulation than invariant T cells. The amount of plate bound antibody may also be reduced which may increase the dependence on costimulation for expansion of the T cells.

Additionally, the presence of different cytokines or combinations of cytokines may be used to favor the expansion of a desired subpopulation of T cells. For example, the NK T cells, CD1d-reactive T cells, or JαQ$^+$ T cells may be incubated with IL-4, IL-7, or IL-12 during expansion.

The expanded NK T cells, CD1d-reactive T cells, or JαQ⁺ T cells may be re-introduced into mammals as described in Example 7.

EXAMPLE 9

Reduced Number of Invariant NK T Cells in Cancer Patients

As described further below, prostate cancer patents have fewer invariant NK T cells than healthy patients. Thus, the antibodies of the invention that increase the number or activity of invariant NK T cells may be used as therapeutics for the prevention, stabilization, or treatment of prostate cancer. In addition, ex vivo expanded invariant NK T cells may be administered to subjects to prevent, stabilize, or treat prostate cancer. Invariant NK T cells may also be present at reduced levels in subjects with other types of cancer; thus, these methods may be used to treat other forms of cancer.

Cancer Patients Analyzed in this Study

Cancer patients in this study had advanced androgen independent prostate cancer (Catalona, N. Engl. J. Med. 331:996, 1994; Bubley and Balk, Hematol. Oncol. Clin. North Am. 10:713, 1996). All patients were treated previously with androgen ablation therapy by orchiectomy or administration of a leutinizing hormone releasing hormone (LHRH) agonist. At the time of study, all patients had positive bone scans and rising levels of prostate specific antigen (PSA)(>50 ng/ml), indicative of progressive metastatic disease. All but one patient had not received cytotoxic chemotherapy. Prostate cancer patients in remission were similarly treated with androgen ablation therapy but had negative bone scans and stable, low (<10 ng/ml) levels of PSA.

Methods Used for Ex Vivo Expansion of Vα24 Positive T Cells

Peripheral blood (10-20 ml) was drawn in heparin containing tubes from healthy donors and prostate cancer patients who had given their informed consent. PBMCs were isolated using Ficoll-Paque (Amersham Pharmacia, Uppsala, Sweden). Vα24 positive T cells were stained with an anti-Vα24 monoclonal antibody (C15) (Coulter, Miami, Fla.) followed by a goat anti-mouse IgG (H⁺L) FITC conjugate (KPL, Gaithersburg, Md.) and were sorted by high speed FACS (Modular Flow FACS, Cytomation, Boulder, Colo.) (Dellabona et al., J. Exp. Med. 180:1171, 1994). Autologous PBMCs were irradiated (5000 rads) and used as APCs. The FACS purified Vα24⁺ cells were initially co-cultured in 96 well flat bottomed plates (approximately 20,000 per well) with equal numbers of autologous irradiated PBMCs in the presence of α-GalCer (50 ng/ml, KRN7000, Kirin Brewery Co., Gunma, Japan) and recombinant IL-2 (100 U/ml) (National Cancer Institute, Bethesda, Md.). Cultures were then gradually expanded into 24 well plates using the same medium. In some cultures, human recombinant IL-12 (1 ng/ml) (Genetics Institute, Cambridge, Mass.) was added during the last week of culture.

Methods Used for Flow Cytometry Analysis of Expanded T Cells

Phenotypic analysis of α-GalCer expanded cells was performed by two or three color flow cytometry after three to four weeks in culture. Previous reports have shown that dual staining for Vα24 and Vβ11 is a marker of invariant NK T cells, as Vα24 and Vβ11 are used very infrequently by bulk T cells (Dellabona et al., J. Exp. Med. 180:1171, 1994; Exley et al., J. Exp. Med. 186:109, 1997; Prussin and Foster J. Immunol. 159:5862, 1997). Antibodies used were anti-Vα24 PE, anti-Vβ11 FITC, anti-CD8β PE (Immunotech), anti-CD3 Cychrome, anti-CD161 PE, and anti-CD4 Cychrome (PharMingen, La Jolla, Calif.). As described previously (Exley et al., J. Exp. Med. 186:109, 1997; Exley et al., J. Exp. Med. 188:867, 1998), approximately 1×10⁶ cells were suspended in 50 μl of FACS buffer (phosphate buffered saline with 1% fetal bovine serum and 0.1% NaN₃) in single wells of 96 well plates (Exley et al., J. Exp. Med. 186:109, 1997; Exley et al, J. Exp. Med. 188:867, 1998). Non-specific antibody binding was blocked by pre-incubating cells with 10% human serum for 15 minutes on ice. Antibodies were then added to cell suspensions and incubated for 20 minutes on ice. Cells were washed twice with FACS buffer and analyzed using a FACScan (Becton Dickinson) with Cell Quest Software.

The analysis of invariant NK T cells in freshly isolated PBMC from healthy donors and cancer patients also used the 6B11 monoclonal antibody. In these experiments, cells were stained with 6B11-FITC and anti-Vα24-PE (which did not cross-compete) to detect cells expressing the invariant TCR. Due to the low frequency of these cells in cancer patients, between 10⁵ and 10⁶ total cells were analyzed.

Results Showing Decreased Number of Invariant NK T Cells in Cancer Patients

Figures 19A, 19B, 19C, 19D, 19E, 19F:
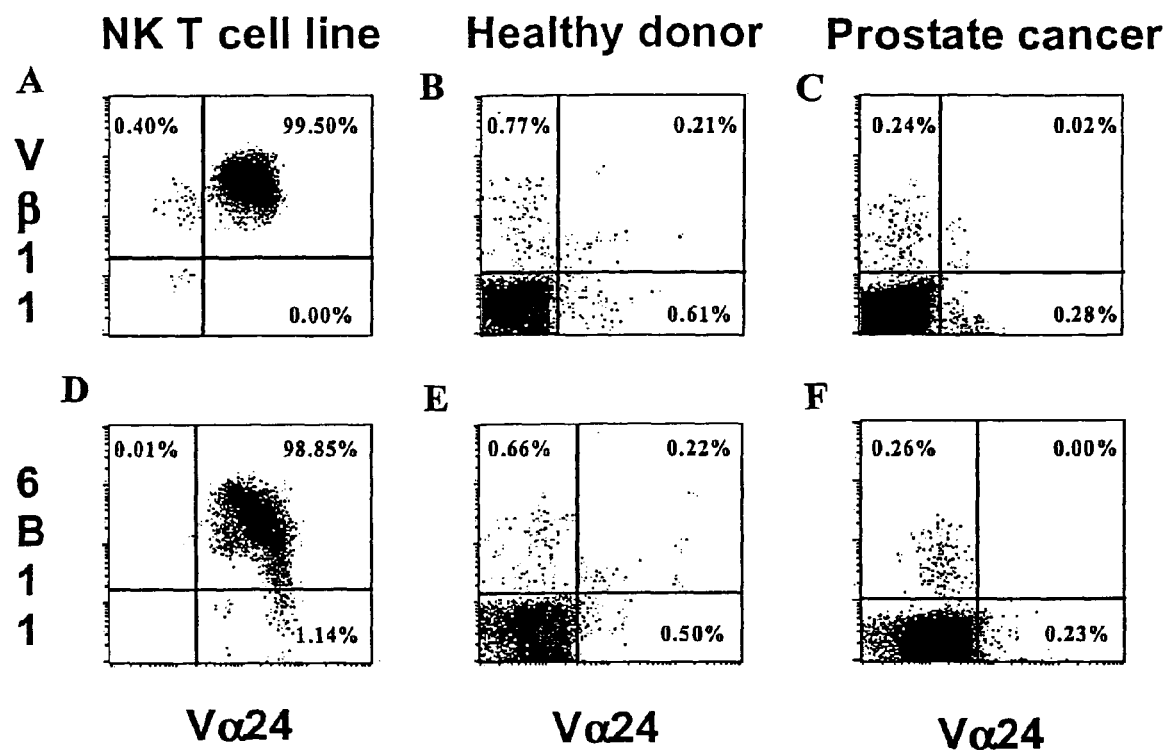
FIGS. 19A-19F are graphs showing the flow cytometry analysis of peripheral blood from a healthy donor (FIGS. 19B and 19E) or prostate cancer patient (FIGS. 19C and 19F), or an NK T cell line (FIGS. 19A and 19D), analyzed by two-color flow cytometry with Vα24-PE and either Vβ11-FITC (FIGS. 19A-19C) or 6B11-FITC antibody (FIGS. 19D-19F). The NK T cell line was generated by α-GalCer expansion of Vα24 purified cells from a healthy donor.

Invariant NK T cells in the peripheral blood of healthy donors and cancer patients were quantitated by 2-color flow cytometry with a Vα24 monoclonal antibody and a Vβ11 monoclonal antibody or the 6B11 monoclonal antibody against the invariant Vα24-JαQ TCR. Invariant NK T cell lines, generated by α-GalCer expansion of Vα24⁺ T cells from healthy donors, were reactive with Vα24, Vβ11, and 6B11 monoclonal antibodies (FIGS. 19A and 19D). The observation that Vβ11 was expressed by virtually all of the α-GalCer expanded Vα24⁺ T cells from this and multiple other healthy donors further indicated that this VP was necessary to generate α-GalCer reactive invariant NK T cells.

Vα24⁺ Vβ11⁺ double positive T cells were found in the peripheral blood of healthy donors in numbers that were comparable to Vα24⁺ 6B11⁺ cells, consistent with a large fraction of Vα24⁺ Vβ11⁺ cells being invariant NK T cells (FIGS. 19B and 19E). The average fraction of Vα24⁺ 6B11⁺ cells in a series of healthy donors was 0.11%. Smaller numbers of Vα24⁺ Vβ11⁺ T cells were found in the peripheral blood of advanced prostate cancer patients (Tables 4 and 5). Moreover, there were no detectable Vα24⁺ 6B11⁺ cells in 5 of 6 patients examined (FIGS. 19C and 19F). These results indicated that invariant NK T cells were decreased in advanced prostate cancer patients.

TABLE 4

Number of invariant NK T cells in PBMC based on staining with the 6B11 and anti-Vα24 antibodies

| Donor | | Va24⁺ 6B11⁺ (invariant) |
|---|---|---|
| Healthy (n = 3) | mean | 41 × 10⁵ |
| | range | 14 × 10⁵ to 90 × 10⁵ |
| Prostate Cancer (n = 7) | mean | 4 × 10⁵ |
| | range | 0 to 20 × 10⁵ |

TABLE 5

Percentage of Va24+ cells that are invariant T cells based on staining with the anti-Vα24 antibody and either the anti-Vb11 or the 6B11 antibody

| Donor | | $\frac{Va24^+Vb11^+}{Va24^+}$ | $\frac{Va24^+6B11^+(invariant)}{Va24^+}$ |
|---|---|---|---|
| Healthy n = 3 | mean (range) | 4.8% (2-7%) | 4.3% (1.4-6.5%) |
| Prostate Cancer n = 6 | mean (range) | 2.3% (0-8.0%) | 0.4% (0-2.3%) |

Results from Expansion of Invariant NK T Cells from Healthy Donors

Due to the small numbers of invariant NK T cells in peripheral blood, one round of ex vivo expansion was carried out to further assess the frequency and function of these cells. Invariant NK T cells from healthy donors and advanced prostate cancer patients were isolated from peripheral blood through an initial FACS purification with a Vα24 specific monoclonal antibody, followed by selective expansion in vitro for three to four weeks with α-GalCer and autologous irradiated PBMCs as a source of APCs. T cells were then analyzed by dual staining with Vα24 and Vβ11 or 6B11 monoclonal antibodies.

Figures 20A, 20B, 20C, 20D:
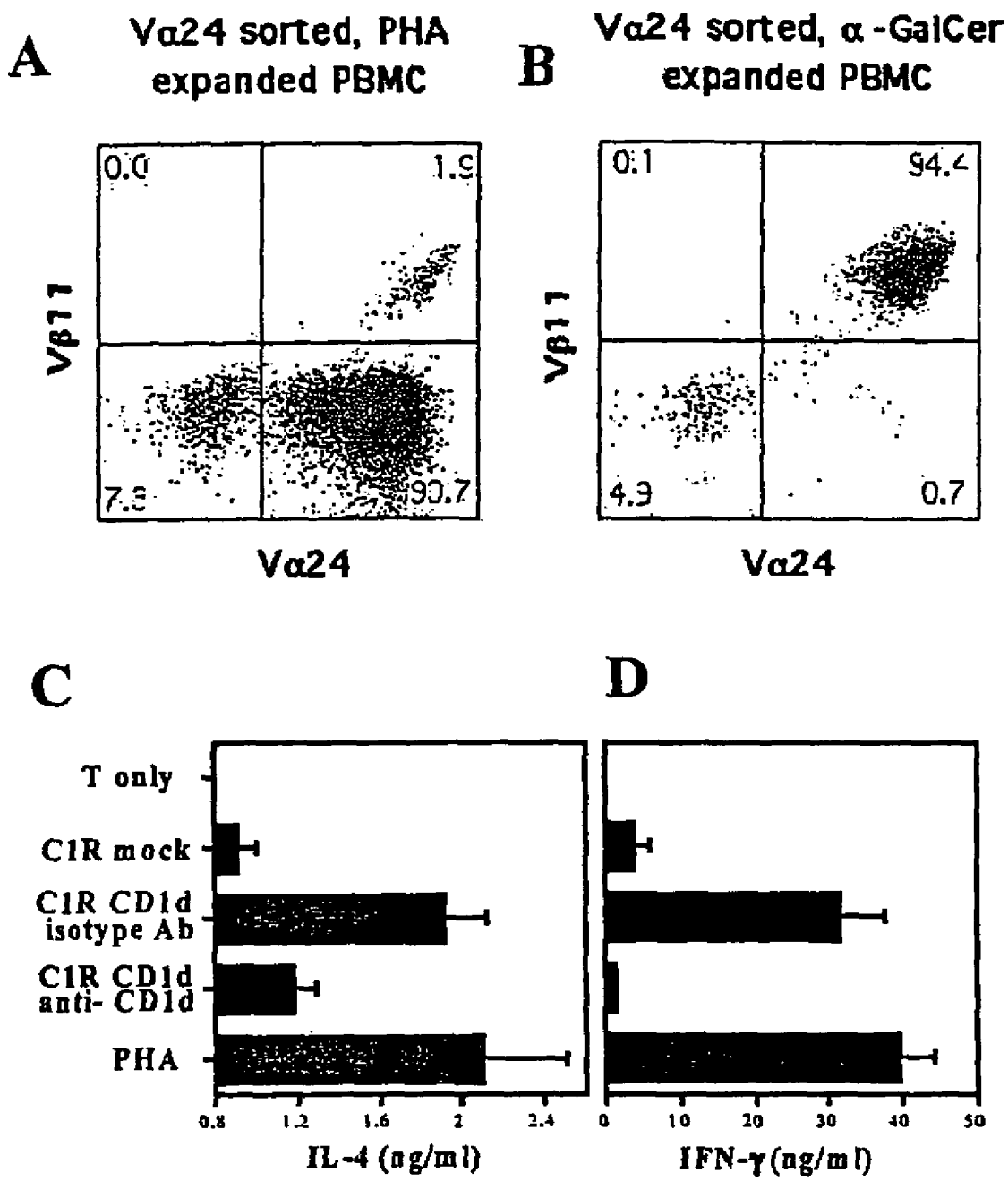
FIGS. 20A and 20B are graphs showing the two color flow cytometry analysis with Vα24-PE and Vβ11-FITC monoclonal antibody of Vα24 sorted cells after a three week expansion with PHA (FIG. 20A) or α-GalCer and autologous PBMC feeders (FIG. 20B).
FIGS. 20C and 20D are bar graphs showing the production of IL-4 and IFN-γ respectively, by an invariant NK T cell line stimulated PHA or stimulated with mock transfected or CD1d transfected C1R human EBV-transformed B cells in the presence of either an anti-CD1d monoclonal antibody (51.1, 10 µg/ml) or an isotype control antibody. The results in FIGS. 20A-20D are representative of multiple healthy donors, as shown below.

FACS purified Vα24+ T cells stimulated in vitro with a T cell mitogen, PHA, yielded only a minor population of Vα24+ Vβ11+ T cells that varied in number with different donors (FIG. 20A). In contrast, stimulation of the purified Vα24+ T cells from healthy donors with α-GalCer and autologous irradiated PBMCs yielded a major Vα24+ Vβ11+ population (FIG. 20B, 94.4% of total cells). Additional phenotypic analysis of these α-GalCer expanded Vα24+ Vβ11+ T cells from a series of healthy donors demonstrated major CD4+ and CD4−CD8-populations and showed that the majority from each donor (>70%) expressed CD161.

The α-GalCer expanded Vα24+ Vβ11+ T cells from healthy donors were assessed for CD1d recognition and cytokine production. Consistent with many of the cells being CD1d reactive invariant NK T cells, the cells produced substantial quantities of both IL-4 and IFN-γ in response to CD1d transfected C1R cells, but not mock transfected C1R cells (FIG. 20C). The CD1d specificity of this recognition was further demonstrated by blocking with an anti-CD1d monoclonal antibody, 51.1, but not an isotype matched control Ab. The cytokine responses to CD1d were equivalent to those obtained after polyclonal stimulation of these T cells with PHA, confirming that most of the cells were indeed CD1d-reactive T cells. These responses were all comparable to those obtained previously with invariant NK T cell clones from healthy donors (Exley et al., J. Exp. Med. 186:109, 1997; Exley et al., J. Exp. Med. 188:867, 1998), indicating that these latter in vitro established clones reflected the functional status of the cells in vivo.

Figure 21A:
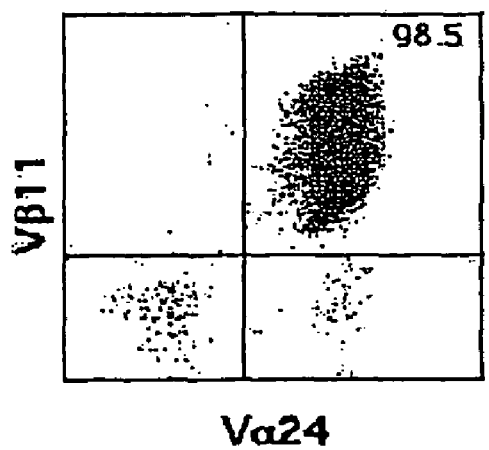
FIGS. 21A-21C are graphs showing the decreased expansion of invariant NK T cells from prostate cancer patients versus healthy donors. α-GalCer expanded invariant NK T cells from a healthy donor (FIG. 21A), advanced prostate cancer patient (FIG. 21B), and prostate cancer patient in remission (FIG. 21C) were analyzed by Vα24-PE and Vβ11-FITC staining.
Figure 21B:
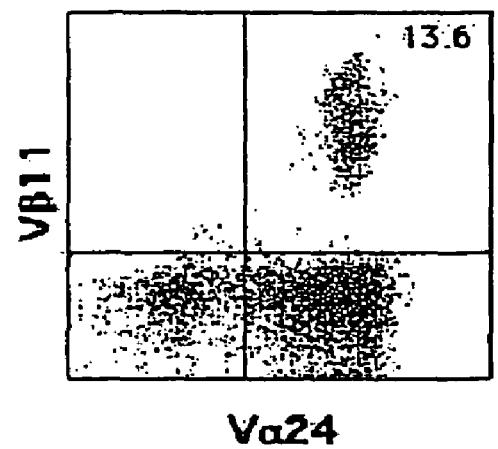
Figure 21C:
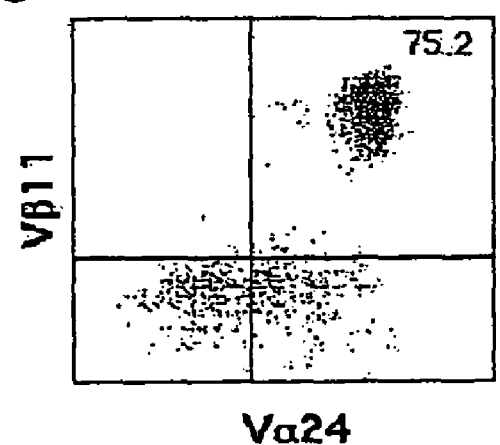

Decreased Expansion of Invariant NK T Cells from Advanced Prostate Cancer Patients Invariant NK T cells from patients with advanced androgen independent prostate cancer were examined similarly. Relative to the healthy donors, there was a decrease in the total number of cultured cells recovered from patients with advanced androgen ablation refractory prostate cancer and a marked decrease in the fraction of expanded cells that were Vα24+ Vβ11+ invariant NK T cells (FIGS. 21A and 21B, 98.5% versus 13.6% invariant NK T cells in a healthy donor and androgen ablation refractory prostate cancer patient, respectively). Also shown are α-GalCer expanded Vα24+ T cells from an androgen ablation treated prostate cancer patient in remission (75% invariant NK T cells), indicating that the androgen ablation therapy did not account for the decreased expansion of invariant NK T cells (FIG. 21C).

Figure 21D:
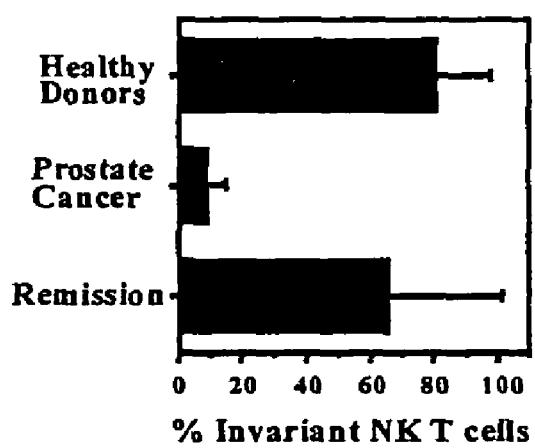
FIG. 21D is a bar graph of the percentage of Vα24+ Vβ11+ cells (mean and standard deviation) after α-GalCer expansion from a series (≧6) of donors. These results are also summarized in FIGS. 12-17

Data from a series of patients with advanced androgen independent prostate cancer, all with metastatic disease and rising levels of prostate specific antigen (PSA), confirmed the markedly diminished recovery of Vα24+Vβ11+ invariant NK T cells (mean of 10% from prostate cancer patients versus >80% from healthy donors) (FIG. 21D). These results were consistent with the decreased numbers of invariant NK T cells detected by Vα24 and Vβ111 or 6B11 staining in peripheral blood of the advanced prostate cancer patients. Other factors including decreased proliferation or increased apoptosis during the in vitro stimulations could also have contributed to the lower recovery. In contrast, the recovery of Vα24+ Vβ11+ invariant NK T cells from prostate cancer patients receiving androgen ablation therapy, but who were in remission, was closer to the healthy donors (FIG. 21D).

EXAMPLE 10

Reduced Activity of Invariant NK T Cells in Cancer Patients

In addition to being present at reduced levels, invariant NK T cells have reduced activity in prostate cancer patients. In particular, these invariant NK T cells produced less IFN-γ (a Th1 effector). As described below, incubation with IL-12 increased the activity of these invariant NK T cells to produce IFN-γ. These results support the ability of IL-12 to bias invariant NK T cells towards Th1 responses such as cytotoxic activity which is desirable for the treatment of cancer. Methods used for measurement of cytokine production and CD1d reactivity For cytokine production, $1 \times 10^5$ cells/well in 96 well plates were co-cultured with an equal number of CD1d or mock transfected C1R cells in RPMI 1640 medium with 10% FBS, 20 U/ml IL-2, and 1 ng/ml PMA, as described previously (Exley et al, J. Exp. Med. 186:109, 1997). Cellular responses to CD1d were blocked with an anti-CD1d antibody, 51.1 at 10 μg/ml (Exley et al., J. Exp. Med. 186:109, 1997; Exley et al., Immunology 100:37, 2000). Supernatants were collected at 48 hours and 72 hours for IL-4 and IFN-γ measurements, respectively. Released cytokine levels were determined in triplicates by capture ELISA with matched antibody pairs in relation to cytokine standards (Endogen, Inc. Cambridge, Mass.). The limit of detection range of these assays for both IFN-γ and IL-4 was 10-50 μg/ml.

Figures 22A, 22B, 22C, 22D, 22E:
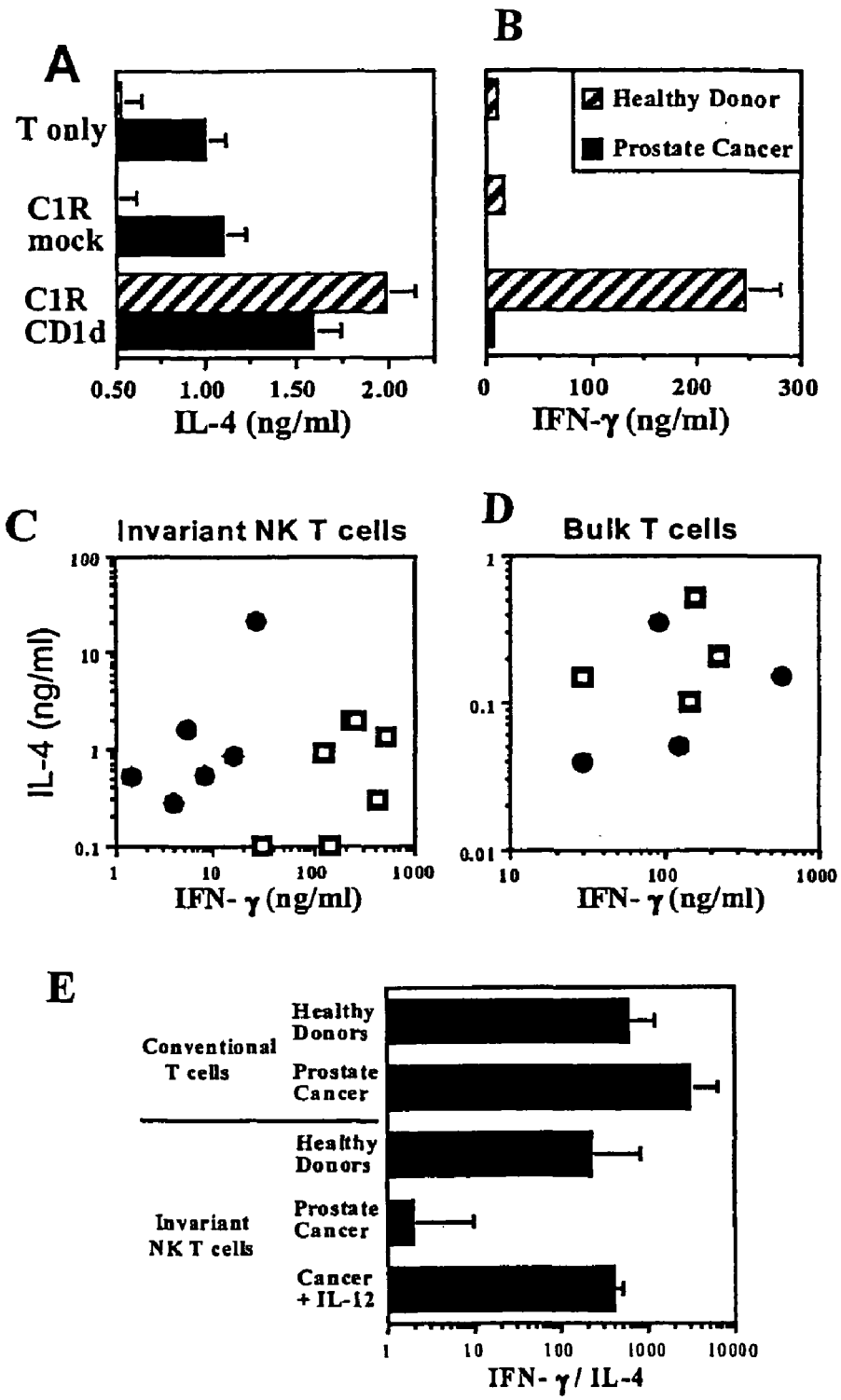
FIGS. 22A-22E are graphs showing the loss of IFN-γ responses by invariant NK T cells from prostate cancer patients.

Results Demonstrating Loss of IFN-γ Production by Invariant NK T Cells from Cancer Patients Prostate cancer patient derived invariant NK T cells proliferated and produced similar levels of IL-4 in response to CD1d transfected cells as invariant NK T cells from a health donor (FIG. 22A). However, their production of IFN—was markedly reduced relative to invariant NK T cells from the healthy donor (FIG. 22B). Analysis of IL-4 versus IFN-γ production by α-GalCer expanded invariant NK T cells from a series of advanced prostate cancer patients and healthy donors confirmed a striking loss of IFN-γ production by the cells derived from prostate cancer patients (FIG. 22C log scale for IFN-γ). This loss of IFN-γ relative to IL-4 was most evident when IFN-γ/IL-4 production ratios were compared, with a difference of approximately 50-fold between the prostate cancer and healthy donor derived NK T cell lines (FIG. 22E).

To determine whether this loss of IFN-γ production was common to other T cell populations, bulk peripheral blood T cells from advanced androgen independent prostate cancer patients and healthy donors were stimulated in vitro with PHA. The results showed that IFN-γ production by bulk T cells from prostate cancer patients was intact (FIG. 22D), with similar IFN-γ/IL-4 ratios observed in the cells from prostate cancer patients versus healthy donors (FIG. 22E). Taken together, these data demonstrated a selective loss of IFN-γ production in the invariant NK T cell population from advanced prostate cancer patients.

As invariant NK T cells may contribute to the anti-tumor effects of IL-12, it was next determined whether these cancer patient derived cells could respond to IL-12. Prostate cancer derived invariant NK T cells were treated with IL-12 (1 ng/ml) during the last week of culture to determine whether they could respond to this cytokine. The IL-12 treated cells showed a marked increase in IFN-γ production, and had ratios of IFN-γl/IL-4 production that were comparable to those in the healthy donors (FIG. 22E, Cancer+IL-12).

EXAMPLE 11

Reduced Levels of NK T Cells in Multiple Sclerosis Patients

Multiple sclerosis (MS), is an inflammatory, demyelinating disease of the central nervous system (CNS) that likely involves an autoimmune response directed against self-myelin associated antigens. To determine whether MS patients have fewer NK T cells, the percentages of NK T cells (Vα24JαQ$^+$) in peripheral blood samples from MS patients with Primary Progressive (n=6) or Relapsing Remitting (n=8) disease were compared to normal donors (n=6). The percentage of NK T cells in normal donors was similar to previous reports (0.114±0.020), whereas the percentage of NK T cells in MS patients with Primary Progressive (0.010±0.007) or Relapsing Remitting (0.027±0.071) disease was significantly less. This smaller number of NK T cells in MS patients suggests that increasing the number and/or activity of NK T cells may be useful for the treatment or prevention of MS, such as Relapsing Remitting, Primary Progressive, or Chronic Progressive MS. Additionally, samples from MS patients may be taken at various time points to determine whether the number of NK T cells in the periphery of these MS patients fluctuates over time and correlates with the status of their disease symptoms.

EXAMPLE 12

Use of 6B11 as a Diagnostic Tool to Study Clinical Cohorts

CD1d-restricted T cells may play an immunoregulatory role in multiple immunologic disorders. To test the diagnostic utility of the 6B11 antibody to monitor the clinical status of high-risk prediabetics and HIV-infected patients, the 6B11-FITC antibody in combination with the Vα24-PE antibody were used to determine the frequency of circulating CD1d-restricted T cells in diabetic patients on the day of diagnosis and in the HIV MACS cohort followed at UCLA medical center. PBL were stained and analyzed by FACS as described above. In addition, dendritic cell (DC) subtypes were determined for the HIV MACS cohort. The results are summarized in FIGS. 23 and 24.

EXAMPLE 13

Gene Expression in Invariant T Cells from Identical Twins Discordant for Type 1 Diabetes An identification of the pattern of genes activated in a particular T cell type may provide information predictive of the function of that T cell subpopulation. For example, changes in gene expression patterns in the cytokine/chemokine family are particularly relevant given the association of cytokine secretion and the in vivo function for T cells. As described below, the gene expression pattern for Vα24JαQ T cells was determined to better understand the role of these cells in autoimmunity and type 1 diabetes. These method may also be used to determine the role of any other T cells subpopulation of interest in the development and/or progression of any disease or condition.

To investigate the transcriptional consequences of T cell receptor activation in human Vα24JαQ T cell clones, DNA microarrays were used to quantitate changes in mRNA levels following anti-CD3 stimulation of clones derived from identical twins discordant for type 1 diabetes and IL-4 secretion (Wilson et al., Proc. Natl. Acad. Sci. USA 97(13):7411-7416, 200). Activation resulted in significant modulation of 226 transcripts in the IL-4 secreting clone and 86 in the IL-4-null clone. Only twenty eight of these genes were in common. The differences observed suggest both ineffective differentiation of diabetic Vα24JαQ T cells and a role for invariant T cells in the recruitment and activation of cells from the myeloid lineage.

Because the defect in IL-4 secretion was likely the result of multiple differences, a representative clone pair was chosen for intensive analysis utilizing DNA microarrays that monitor the expression of approximately 6800 genes (Unigene collection). The DNA microarrays provide a practical and reproducible approach for large scale study of complex differences in gene expression (Lockhart et al., Nature Biotechnology 14, 1675-1680, 1996; Holstege et al., Science 283, 83-87, 1999; Cho et al., Molecular Cell 2, 65-73, 1998). Expression profiles were determined following four hours of stimulation with anti-CD3 or control IgG. This time point was selected because it was used in a previous analysis of cytokine secretion in clones derived from monozygotic twin pairs discordant for Type 1 diabetes. The number of genes with detectable expression either before or after stimulation was nearly identical for the IL-4 null and IL-4 secreting clones (1523 and 1558, respectively). As expected, the frequency of the majority of transcripts was unchanged. Only about ⅔ of this set (988) were shared between the two clones. The number of genes whose expression after anti-CD3 stimulation was found to increase or decrease by at least 2-fold relative to unstimulated were 86 (6%) and 226 (15%) in the IL-4-null and IL-4$^+$ clones, respectively. In order to more thoroughly analyze the differences in gene expression between the IL-4 null and IL-4 secreting clones, genes were grouped into six distinct expression patterns, using the Self-Organizing Map algorithm (Tamayo et al., Proc. Nat. Acad. Sci. USA 96, 2907-2912, 1999).

Figure 25B:
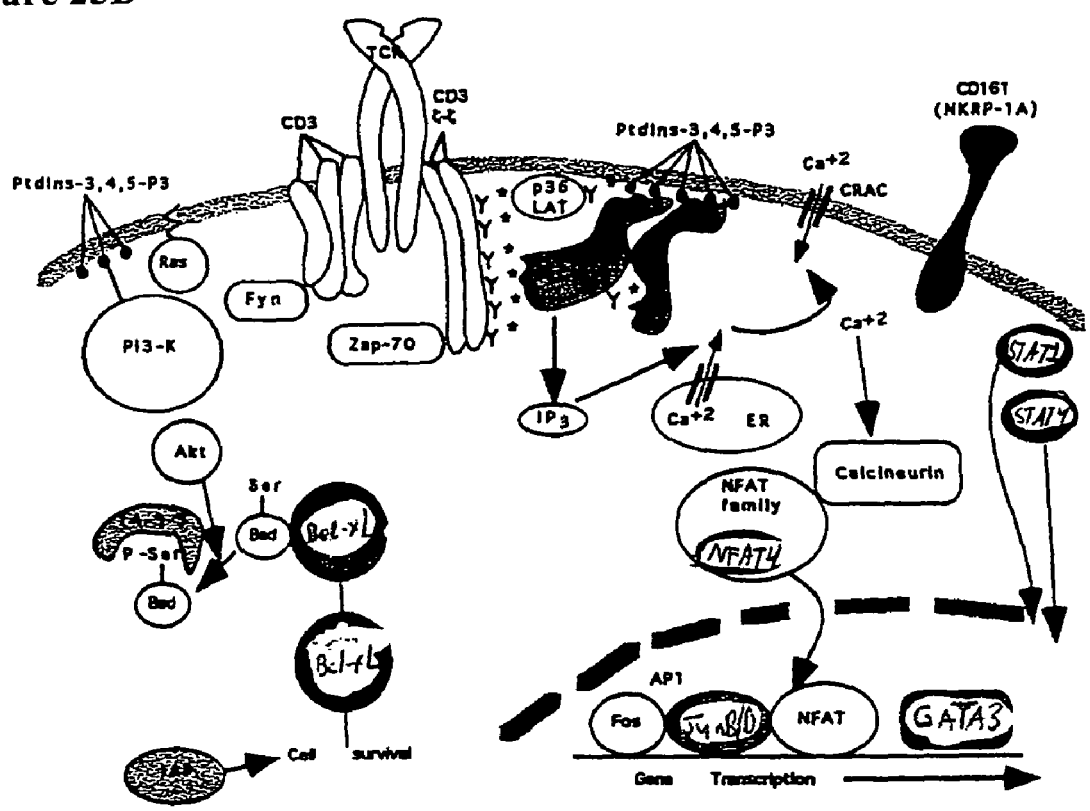
FIG. 25B is a schematic illustration of a model for identified transcripts whose discordant expression is in accord with observed cell phenotypes. Pictured in cartoon format are genes whose transcripts have clearly defined cellular roles and whose discordant expression between GW4 and ME10 correlated with the established phenotypic differences. The genes are related by either being downstream of PI-3 kinase, particularly several genes that regulate cell survival or are directly required for calcium flux and calcium-regulated gene transcription. Average copies of mRNA molecule/million for genes that were significantly altered by anti-CD3 treatment for GW4 (resting, activated) and ME10 (resting, activated) respectively were: Itk, (49, 115) and (25, 19); GATA3, (13, 26) and (8, 11); Jun-B, (15, 118) and (14, 30); Jun-D, (107, 291) and (68, 130); NFAT4, (33, 35) and (64, 26); STAT4, (36, 29) and (76, 36); 14-3-3, (24, 45) and (83, 41); Bcl-XL, (11, 50) and (6, 7); and IAP, (14, 211) and (10, 41). Selected genes whose expression was constitutive but discordantly expressed for GW4 vs. MW10 (GW4, ME10) were: NKR-P1A, (29, 459); and STAT1, (27, 79).

When examined on the DNA microarrays, activation of Vα24JαQ T cell clones by anti-CD3 resulted in significant changes in transcripts of the cytokine/chemokine family. Marked differences in the expression of genes in this category were found when comparing the IL-4$^+$ with the IL-4-null clone (FIG. 25A). The transcriptional changes noted in MIP-1α, MIP-1β, TNF-α, TNF-β, IL-5, IL-13, and GM-CSF have each been verified at the protein level by ELISA. When comparing clones from the disease discordant twins, robust changes were detected in several transcripts in the IL-4-null clone including those in common with the IL-4 secreting clone, and that a total of 1523 transcripts were present at significant levels, of which 535 were unique to the IL-4-null clone. In addition, the clone pairs secreted equivalent amounts of IFN-γ in response to anti-CD3. Importantly, if a significant portion of the effector function of CD161$^+$ Vα24JαQ T cells occurs through cytokine secretion, then the IL-4 null clone has failed to engage the complete spectrum of differentiated function. Recently, defects in the ability to both respond to activation and subsequently secrete cytokines were also noted in the NK T cells of NOD mice (Falcone, J. of Experimental Medicine 190, 963-972, 1999). In addition, this combination of cytokines/chemokines suggests that $CD161^+$ T cells may also recruit and regulate immature dendritic cells and monocytes.

When comparing the $IL-4^+$ and IL-4-null clones, significant differences in expression were noted in other genes important for cell survival, cytokine secretion, and calcium flux that are in part activated through PI 3-kinase signaling, such as BCLXL, IAP, PLCγ1 and the tec family kinase, Itk. These transcripts were found at significantly greater abundance in the $IL-4^+$ clone. Differences were also noted in the expression mRNAs encoding transcription factors and signaling modulators important for cytokine secretion and Th-phenotype. These included GATA3, STAT1, STAT4, JunB, JunD, and NFAT4. Notably, JunB and GATA3 were recently reported to be preferentially expressed in Th2 T cells. Transcriptional activation of GATA3, JunB, as well as JunD, was found selectively in the $IL-4^+$ clone. The transcripts for STAT1 (IFN-γ signaling), STAT4 (IL-12 signaling) and CD161 (a co-activator of Vα24JαQ T cell proliferation and IFN-γ secretion) were overexpressed in the IL-4-null clone relative to the $IL-4^+$ clone. Importantly, the transcription factor NFAT4 thought to act in part as a suppressor of IL-4 transcription was overexpressed in the IL-4-null clone relative to the $IL-4^+$ clone. Based on this data, the discordant regulation of other genes such as transcription factors might be predicted to be important for controlling Th-phenotype. A model for regulated genes whose expression concurs with multiple independent biological observations is presented in FIG. 25B.

The transcriptional profile of activated Vα24JαQ T cell clones revealed that the defect in IL-4 secretion seen in the clone from a diabetic patient (compared to the identical non-diabetic twin) is only one of a large number of differences in gene expression. Importantly, differences were found in the expression of gene products whose activation is in part regulated by PI3-kinase and they appear to be necessary for the generation of a fully differentiated Vα24JαQ T cell.

EXAMPLE 14

CD1d on Myeloid Dendritic Cells Stimulates Cytokine Secretion from and Cytolytic Activity of Vα24JαQ T Cells DC are a distinct population of bone marrow derived antigen presenting cells that play a key role in initiating T cell responses. In humans, three populations of DC are found at very low frequencies (0.03-0.3%) in peripheral blood. Human DC include two myeloid populations—Langerhans cell precursors ($Lin^-/CD11c^+/CD1a^+/Il-3R^-$) and tissue DC ($Lin^-/CD11c^+/CD1a^-/IL-3R^-$)—and a "plasmacytoid" DC (PDC) population ($Lin^-/CD11c^-/CD1a^-/IL-3R^+$). The PDC population also express CXCR3 and CD62L that facilitate homing to the high endothelial venule and movement into lymphoid tissues. PDC undergo activation in lymphoid through ligation of CD40 or by exposure to LPS and produce a variety of cytokines and upregulate T cell stimulatory capacity. The MDC occupy either the epidermis or dermal and other tissue sites, respectively. MDC reside in peripheral tissues in an immature state and readily take up antigens until such time that they receive a signal provided by infection or tissue damage. At this point they become activated and migrate to the draining lymph nodes where they readily produce cytokine such as IL-12p70 and activate naive T cells. Recent studies support a differential role for the MDC and PDC populations in directing the development of Th1 and Th2 responses. Studies in mice and humans also suggest that defective MDC maturation and function may play a role in type 1 diabetes pathogenesis.

The key role of myeloid dendritic cells in priming Th1 cellular immune responses raises the possibility that Vα24JαQ T cells may exert their immunomodulatory effects through interaction with these cells. To test this hypothesis, the expression patterns for CD1d found on DC in vivo and in vitro were assessed, and the functional consequences of an interaction between Vα24JαQ T cell clones and DC cells were examined.

Vα24JαQ T Cell Clones Used for this Study

Derivation of Vα24JαQ T cell clones has been previously described (Wilson et al., Nature 391:177, 1998). Briefly, peripheral blood mononuclear cells (PBMC) from normal donors were single-cell sorted for Vα24/Vβ11 double-positive cells, which were then grown with irradiated feeder PBMC (50,000 cells/well), irradiated 721.221 lymphoblastoid cells (500 cells/well), PHA-P (1 µg/mL), IL-2 (10 U/ml), and IL-7 (10 U/mL) in RPMI 1640 (Sigma) containing 10% heat-inactivated fetal bovine serum, 2 mM L-glutamine, 10 mM HEPES, 100 U/ml penicillin, and 10 µg/ml streptomycin (R10). The resultant clones were then propagated with periodic restimulation by anti-CD3 antibody in the presence of irradiated allogenic feeder PBMC and anti-CD3 antibody. Clones were confirmed to be positive for Vα24 and NKR-P1A by flow cytometry and to have the Vα24JαQ CDR3 TCR by sequencing.

Methods Used for Transcriptional Profiling of T Cells

Transcriptional analysis of Vα24JαQ T cell clones was performed using high density oligonucleotide arrays developed by Affymetrix. Briefly, the cells were activated for four hours with 10 µg/mL soluble anti-CD3 or control IgG, after which total RNA was isolated and reverse-transcribed. The resultant cDNA was used for in vitro transcription with biotinylated nucleotides to produced labeled antisense RNA which was then hybridized to DNA microarray chips (Genechips™, Affymetrix, San Jose, Calif.). After staining with PE-streptavidin, fluorescence of bound RNA was quantitated using a Genechip Reader (modified confocal microscope).

Assays for Cytokine Secretion and Proliferation

Vα24JαQ T cell clones were stimulated (25,000/well) with plate-bound anti-CD3 or control isotype antibody for 4, 8, or 24 hours. Supernatants were collected and assayed for IL-4, IFN-γ, macrophage inflammatory protein-1-α (MIP-1-α), MIP-1-β, TNF-α, and GM-CSF by quantitative ELISA (Quantikine kits, R &D Systems, Minneapolis, Minn., USA). After 24 hours, 1 µCi/well of [$^3$H-]thymidine (Dupont NEN, Boston, Mass.) was added and incorporation measured as described (Wilson et al., Nature 391:177, 1998). Restriction experiments using CD1 isoforms (CD1a, CD1b, CD1c, CD1d and pSR-α-neo vector alone) in transfected C1R cells were also performed as previously described (Wilson et al., Nature 391:177, 1998; Exley et al, The Journal of Experimental Medicine 186:1, 1997).

Preparation of Myeloid Dendritic Cells

Monocyte-derived dendritic cells were generated from fresh PBMC using an adaptation of previously published methods (O'Doherty et al., Journal of Experimental Medicine 178:1067, 1993), or positively selected by anti-CD14 microsphere enrichment as described in the manufacturers protocols (Miltenyi Biotec, Auburn, Calif., USA). Briefly, freshly isolated PBMC prepared from allogenic of sygneic donors were enriched for monocytes by adherence and washing. Immediately after washing, the remaining monocytes were cultured in R10 supplemented with recombinant human IL-4 (rhIL-4; Genzyme) and rhGM-CSF at 1000 U/ml each for an additional 7 days, yielding a non-adherent population of cells that were at least 90% CD1a+/DR+/CD3−/CD14− by flow cytometric analysis.

Cytolytic Assays

Cytolytic activity by Vα24JαQ T cell clones was determined by measuring the specific release of $^{51}$Cr at fours hours. Target cells were labeled with 50 uCi Na$_2$ $^{51}$Cr (New England Nuclear, North Billerica Mass.) for one hour and washed twice. Cytolytic activity was determined in standard chromium release assays with U-bottom 96-well microtiter plates containing $10^4$ labeled target cells per well, with the indicated ratios of effector cells. After a 4 hour incubation at 37° C., the supernatants were harvested and counted on a gamma counter (Cobra, Packard, Downer's Grove Ill.). Percent specific lysis was calculated as [(experimental release−spontaneous release)/(maximal release−spontaneous release)]×100. For some experiments, cytolysis was tested under conditions of calcium chelation, in the presence of EGTA and MgCl$_2$ each at 4 mM.

Antibodies Used for this Study

The 42.1 anti-CD1d monoclonal antibody was a kind gift from Dr. Steven Porcelli (Brigham & Women's Hospital). F(ab')$_2$ fragments of 42.1 and IgG1 control antibodies were prepared with an Immunopure F(ab')$_2$ kit, Pierce (Rockford, Ill.). Goat F(ab')$_2$ Anti-mouse IgG-FITC, human adsorbed, was obtained from Caltag (Burlingham, Calif., USA) FcR-Blocking reagent™ human IgG was obtained from Miltenyi Biotec (Auburn, Calif., USA). NOR3.2 was obtained from Biosource International (Camarillo, Calif., USA). Anti-Vα24, anti-Vβ11, anti-αβTCR, and anti-CD83 were obtained from Immunotech (Coulter/Beckman, Fullerton, Calif., USA). Anti-CD1a, anti-CD4, anti-CD8, anti-CD40L, anti-CD80, anti-CD86, and HLA-DR were obtained from Pharmingen (San Diego, Calif., USA). Anti-CD3, clone UCHT1, was obtained from Ancell (Bayport, Minn., USA) and IgG1 control from Sigma (St. Louis, Mo.).

Methods Used for Flow Cytometry.

Stained cells were analyzed on a FACScan cytometer (Becton Dickinson, Franklin Lakes, USA), and single cell sorting was performed using a MoFlo cytometer (Cytomation, Fort Collins, N.J., USA). For CD1d expression of CD40L, T cell clones were activated with PMA and ionomycin as previously described (Wilson et al., Nature 391:177, 1998; Exley et al, Journal of Biological Chemistry 269:15140, 1994).

Western Blot Analysis for Cd1d

Immunoprecipitates of CD1d from lysates of $5\times10^5$ C1R/CD1d cells, $4\times10^7$ dendritic cells, and $4\times10^7$ control C1R/neo cells were prepared using monoclonal antibody 42.1 coupled to protein A beads. The immunoprecipitates were resolved by SDS-PAGE (5-15%), and probed with an affinity purified rabbit anti-CD1d polyclonal antibody (Exley et al., Journal of Experimental Medicine 188:867, 1998). Bands were visualized by chemiluminescence.

Immunohistochemistry Methods

The NOR3.2 monoclonal antibody was used to determine CD1d expression in fixed, paraffin-embedded tissue by immunoperoxidase staining (Vectastain ABC elite kit with visualization using NovaRed, Vector Laboratories, Burlingame, Calif.). Staining was done as per manufacturer's specifications with NOR3.2 used at 1:100 dilution. The specificity of the signal was confirmed by blocking experiments using a GST-CD1d fusion protein as compared to the GST protein alone.

Results Showing Activation of CD1D-Restricted Vα24JαQ T Cells by Anti-CD3 Treatment.

Figures 26A, 26B:
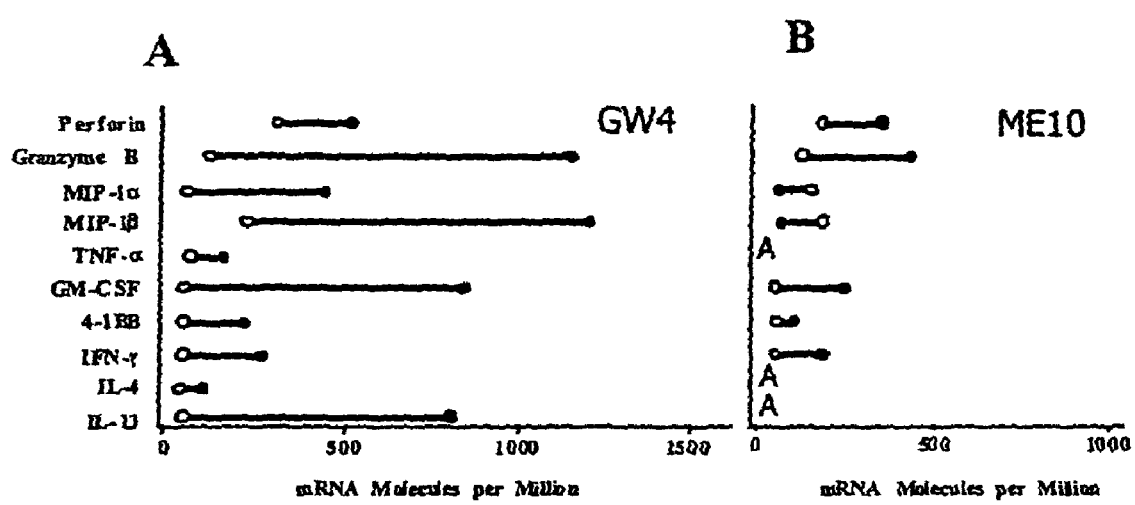
FIGS. 26A-26D are graphs showing the transcriptional induction and release of cytokines and cytolytic enzymes by activated Vα24JαQ T cells.
Figure 26C:
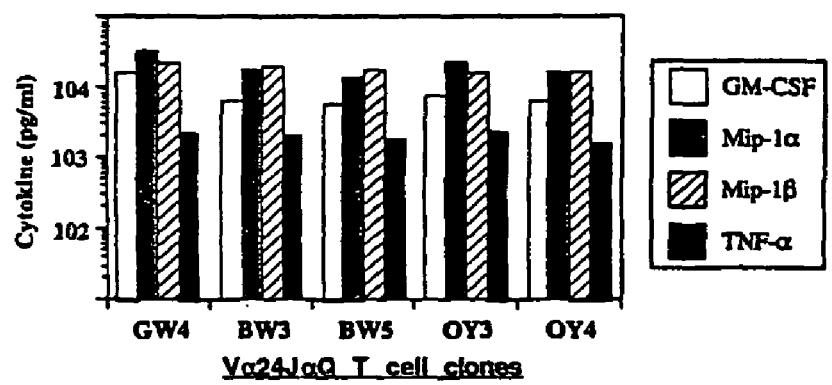
Figure 26D:
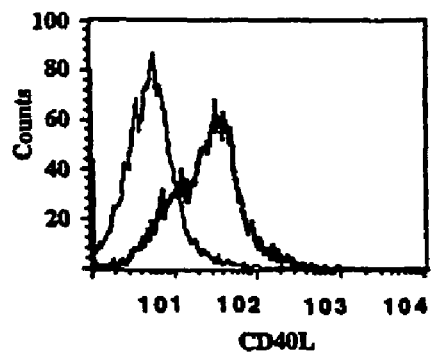

A detailed analysis of the transcriptional profile of Vα24JαQ T cells was performed using high-density oligonucleotide arrays. Activation of clones derived from normal donors resulted in the expression of numerous effector molecules believed to be important for the recruitment and differentiation of myeloid dendritic cells (FIGS. 26A and 26B). Among these were four of sixteen chemokines examined and included MIP-1α and MIP-1β, which are thought to recruit macrophages and immature dendritic cells in vivo. Also produced were GM-CSF, IL-4, and TNF-α, cytokines involved in the differentiation and maturation of myeloid dendritic cells and their subsequent maturation. Activation also induced the expression of eight of twenty-six cytokines tested. These cytokines, as well as CD40 ligand and 4-1BB, were produced by each of the Vα24JαQ T cell clones examined (FIGS. 26A-26D, 27A, and 27B). In addition, activated Vα24JαQ T cells expressed enhanced levels of perforin and granzyme B, proteins usually associated with classic cytotoxic T cells. Thus, their immunomodulatory functions might not be limited to cytokine release, but could involve cytolytic activities as well.

Figures 27A, 27B:
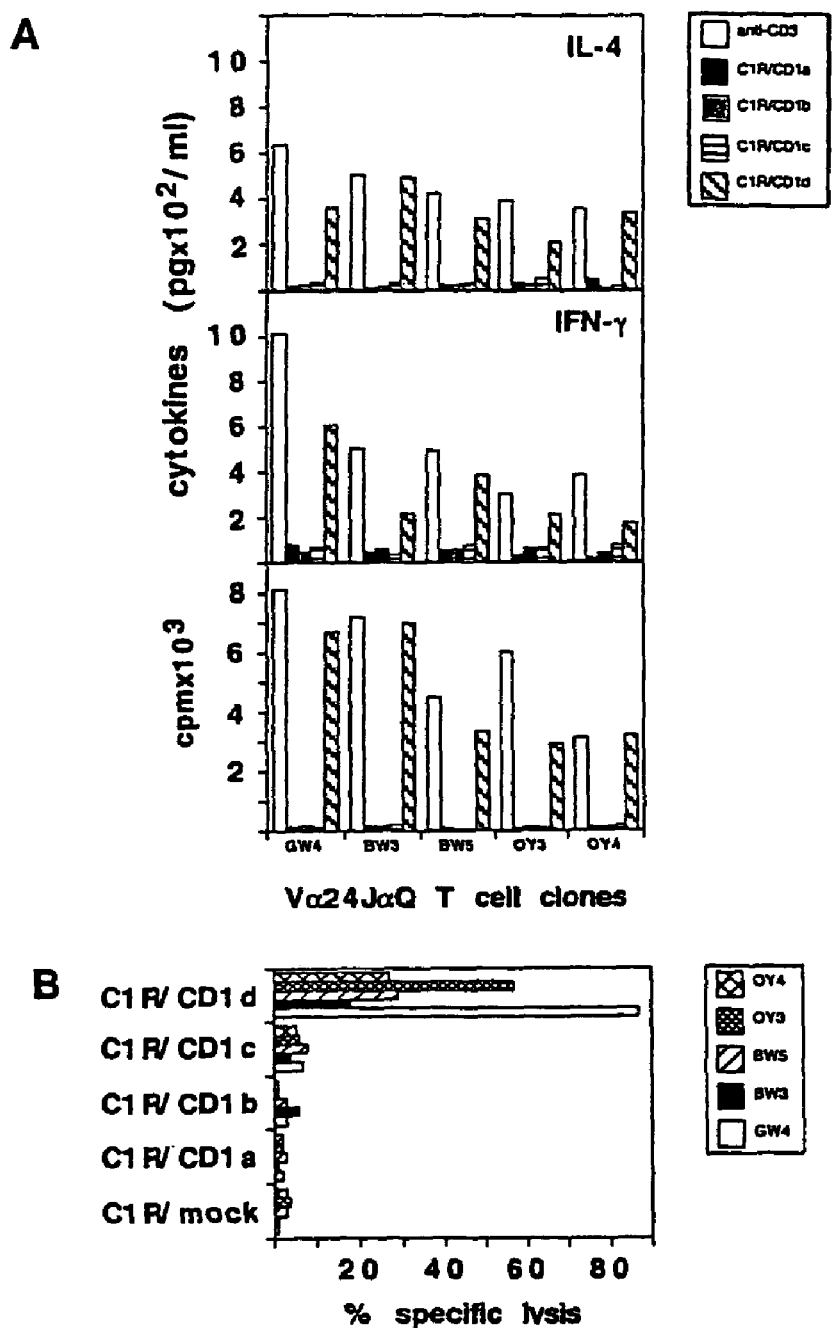
FIGS. 27A and 27B show the CD1d restriction of Vα24JαQ T cell activation.

Activation of Both Cytokine Secretion and Cytolytic Activity of Vα24JαQ T Cells by CD1d Expression on Target Cells In order to investigate Vα24JαQ T cell/DC interactions in a completely autologous system, a new set of clones was generated. These clones were tested for CD1d-specific responses against a panel of lymphoblastoid C1R cells transfected with various CD1 molecules. Cytokine release, as shown for IL-4 and IFN-γ, and proliferation of these clones were specifically restricted by CD1d (FIG. 27A). Activation was induced by CD1d but not by CD1a, CD1b, or CD1c, in agreement with previously published results. Additionally, Vα24JαQ T cell clones were found to specifically lyse C1R cells expressing CD1d, but not the other CD1 family molecules (FIG. 27B). Thus, CD1d-restricted triggering of the invariant TCR activates the secretion of cytokines and a concurrent cytolytic response, a situation similar to that observed for cytotoxic T cells triggered by MHC class I and peptide epitopes.

CD1d is Expressed on Myeloid-Lineage Dendritic Cells

Figures 28A, 28N:
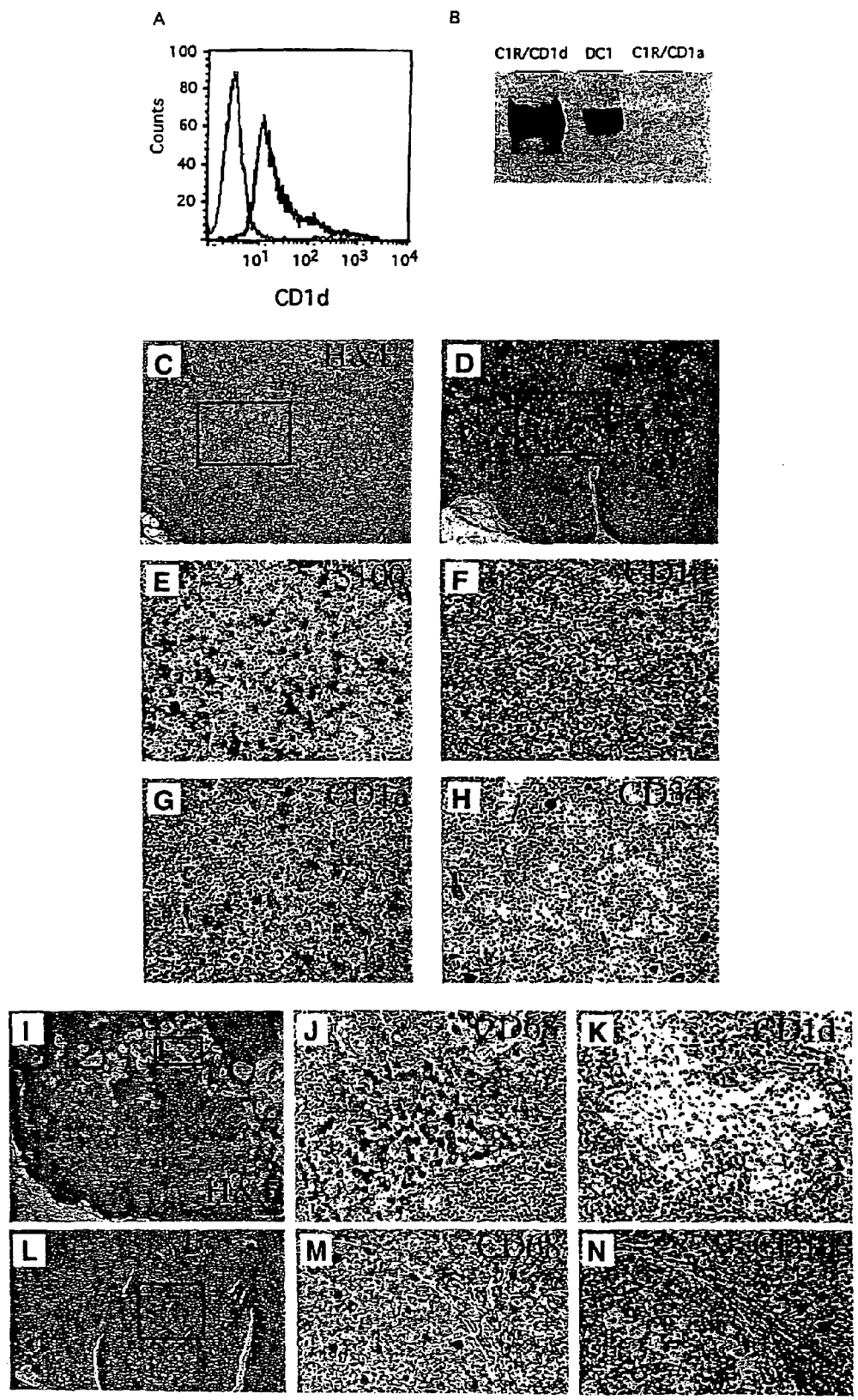
FIG. 28A is a graph of the CD1d expression on myeloid dendritic cells, based on flow cytometric analysis of cultured dendritic cells.

The combination of cytokines and cytolytic proteins produced by Vα24JαQ T cell clones suggested an effector role beyond that of simple Th2 priming by IL-4 secretion, as previously proposed. Given these observations, immune regulation by Vα24JαQ T cells might involve interaction with myeloid dendritic cells which are important for the generation of Th1-like responses. Immature dendritic cells were derived from peripheral blood monocytes differentiated in vitro with IL-4 and GM-CSF and subsequently matured with monocyte conditioned media (O'Doherty et al., Journal of Experimental Medicine 178:1067, 1993). Peripheral blood monocytes are known to express low levels of CD1d, which is promptly lost on culture in vitro. Analysis of mature myeloid dendritic cells (DC1) derived from peripheral monocytes demonstrated the re-acquisition of CD1d expression on the cell surface (FIGS. 28A and 28B), whereas activated B and T lymphocytes did not express CD1d. Immunohistochemical analysis confirmed that CD1d was preferentially expressed in vivo on dendritic cells in the paracortical T cell zones of lymph nodes (FIGS. 28C-28P). Immunostaining of serial sections confirmed that the CD1d is expressed on dendritic cells that also express CD1a and S100. CD1d was not found to be expressed by follicular dendritic cells or follicle tingle body macrophages, and was largely absent from sinus histiocytes, i.e. CD1d expression was targeted to T cell-dependent lymphoid regions. While surveying other histiocytic/monocytic populations in other forms of reactive lymph nodes processes, striking CD1d staining was found on epithelioid histiocytes in both caseating granulomas of *M tuberculosis* infections and other non-mycobacterial granulomas. Murine Vα14Jα281 T cells have been shown to be required for granuloma formation after challenge with lipid extracts from *M tuberculosis*. In addition, several tumors which closely resemble dendritic cells and may be their neoplastic counterparts, namely Langerhans cell histiocytosis and interdigitating dendritic cell tumors, also consistently express CD1d. Thus, the expression of CD1d on dendritic cells both in vitro and in vivo suggests their potential as a physiologic target for Vα24JαQ T cells.

CD1d-Restricted Lysis of Myeloid Dendritic Cells by Vα24JαQ T Cells

Figures 29A, 29B, 29C, 29D, 29E:
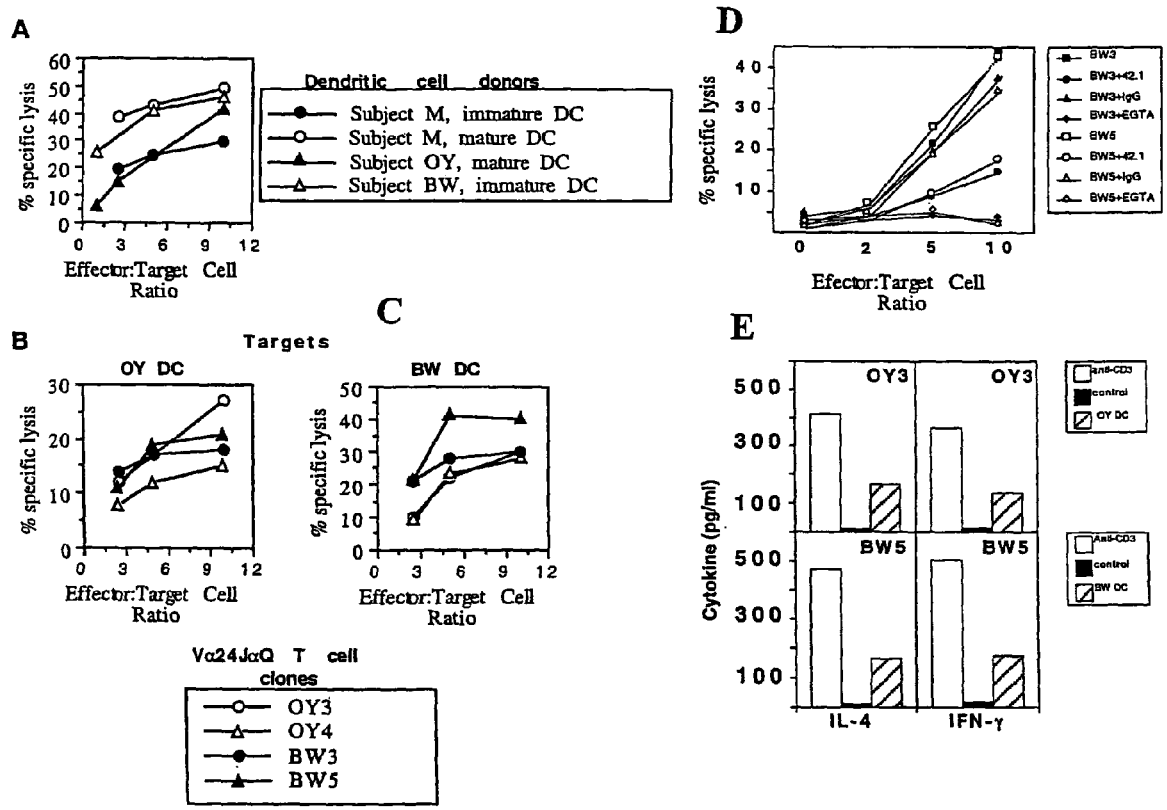
FIGS. 29A-29D are graphs characterizing the cytolysis of myeloid dendritic cells by Vα24JαQ T cells.
FIG. 29E is a bar graph showing the secretion of IL-4 and IFN-γ after co-culture of Vα24JαQ T cell clones OY3 and BW5 with autologous DC.

The ability of Vα24JαQ T cells to interact with dendritic cells was confirmed by testing several Vα24JαQ T cell clones for cytolysis of DC from multiple healthy donors of differing MHC haplotypes (FIGS. 29A and 29B). Both allogenic and autologous dendritic cells were lysed by the clones, indicating that killing was neither MHC-restricted nor alloreactive. Furthermore, cytolysis was completely abrogated by calcium chelation and markedly inhibited by the anti-CD1d monoclonal antibody 42.1 (FIG. 29C). These data suggest that killing was mediated via the perforin/granzyme pathway and required CD1d. Comparison of immature (CD83−) versus mature (CD83+) phenotype dendritic cells demonstrated no consistent difference in recognition by Vα24JαQ T cells (FIG. 29A). Activation of Vα24JαQ T cells by dendritic cells also resulted in secretion of both IL-4 and IFN-γ (FIG. 29D). Thus, exposure of Vα24JαQ T cells to dendritic cells expressing CD1d triggered both cytolytic functions and cytokine release.

Feedback Mechanism for Immune Regulation

After activation by anti-CD3, Vα24JαQ T cells were found to be capable of secreting a broad panel of cytokines, chemokines, and co-stimulatory proteins important for the recruitment and differentiation of myeloid dendritic cells including IL-4 and GM-CSF. Myeloid dendritic cells cultured in the presence of these gene products expressed CD1d and became specific targets for CD1d-restricted killing by Vα24JαQ T cells. Furthermore, CD 1d was preferentially expressed on myeloid dendritic cells in the paracortical T cell zones of lymph nodes corroborating the in vitro expression data.

Because human myeloid-derived dendritic cells (DC1) and lymphoid-derived dendritic cells (DC2) regulate CD4+ T helper cell responses, the specific lysis of DC1 cells by Vα24JαQ T cells suggests that their immunomodulatory function is not limited to Th2 bias induced by IL-4 secretion (Maldonado-Lopez et al., J Exp Med 189:587, 1999; Rissoan et al., Science 283:1183, 1999; Reid et al., Curr Opin Immunol 12:114, 2000). When co-cultured with T cells, DC1 cells secreted high levels of IL-12 and induced T cells with a Th1 phenotype. Co-culture with DC2 cells induced a marked Th2 response (Rissoan et al., Science 283:1183, 1999). Thus, the specific lysis of myeloid dendritic (DC1) cells by Vα24JαQ T cells may serve as a negative feedback mechanism for limiting Th1 T cell responses (FIG. 30).

Previous reports have shown similar lysis results for NK cells. Activated NK cells lysed dendritic cells suggesting a negative feedback mechanism similar to the one proposed for Vα24JαQ T cells. In addition, the in vivo activation of CD1d-restricted T cells by α-GalCer treatment resulted in the marked activation of murine NK cells (Carnaud et al., J Immunol 163:4647, 1999). While this mechanism for activation of NK cells may play a role in the regulation of dendritic cells in vivo, the direct interaction between Cd1d-reactive T cells and DC's demonstrated here would make this step unnecessary.

The site of interaction between Vα24JαQ T cells and dendritic cells is presently unknown. The paucity of Vα24JαQ T cells in a typical lymph node suggests it may occur extranodally and that the CD1d positive dendritic cells present within the lymph node may be those which escape peripheral destruction (Bendelac et al., Annual Review of Immunology 15:535, 1997; Porcelli et al., Annu Rev Immunol 17:297, 1999). The parallel tissue distributions of Vα24JαQ T cells within the reticuloendothelial system and the in vivo expression pattern of CD1 d are strong evidence for a key role for their interaction in regulating the generation of cellular immune responses. The CD1d-restricted T cells are distributed in the liver, gut, spleen, lymph nodes, and thymus (Bendelac et al., Annual Review of Immunology 15:535, 1997; Porcelli et al., Annu Rev Immunol 17:297, 1999), sites of active antigen sampling and presentation by professional antigen presenting cells. Unregulated dendritic cells have also been previously shown to be capable of initiating and maintaining autoimmunity by the presentation of tissue-specific self-antigens. Moreover, DCs 'lingered' in the T cell zones of lymph nodes as a result of missense mutations in the caspase 10 gene of patients with autoimmune lymphoproliferative syndrome type II (ALPS II), a primary finding in this autoimmune disorder. Dysfunction of CD1d-restricted T cells has been clearly correlated with the development of T cell-mediated autoimmune diseases in both rodents and humans. Furthermore, activation or direct transfer of CD1d-restricted T cells was shown to directly inhibit the development autoimmunity in these murine models of autoimmunity.

Figure 30:
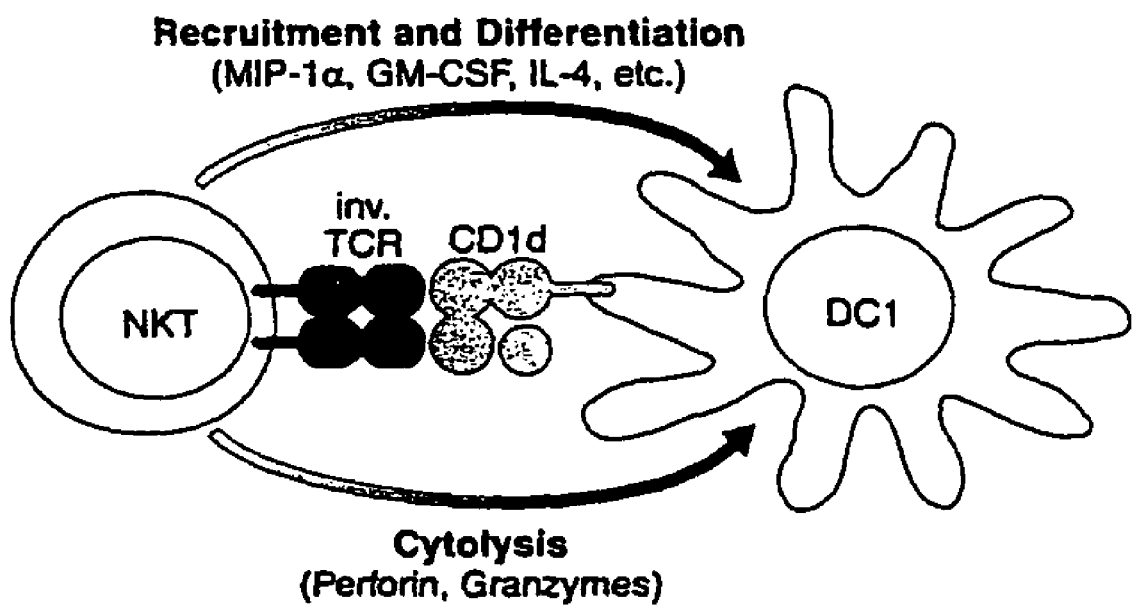
FIG. 30 is a schematic illustration of a model demonstrating the interaction of CD1d-restricted T cells with myeloid dendritic cells. Activation of invariant Vα24JαQ T cells results in the secretion of cytokines and chemokines important for myeloid dendritic cell recruitment and activation. In addition, important cell surface co-stimulatory molecules are also expressed. During myeloid dendritic cell maturation, CD1d is upregulated and activates CD1d-restricted T cells. In addition to the secretion of cytokines and chemokines, activated Vα24JαQ T cells upregulate perforin, granzyme B, and Granulysin. The CD1d-dependent secretion of these molecules then results in the lysis of myeloid dendritic cells.

In summary, the present data suggest that Vα24JαQ T cells are activated by CD1d on myleloid dendritic cells (DC1) to secrete chemokines and cytokines important for the recruitment and differentiation of dendritic cells and thus play an important role in modulating dendritic cell function (FIG. 30). This interaction also activates the cytolytic functions of Vα24JαQ T cells resulting in negative regulation of Th1 cellular immune responses through cytolysis of dendritic cells. This system may be reciprocal to the negative regulation of lymphoid dedritic cells (DC2) by mature T cells which serves to limit Th2 cellular responses (Rissoan et al., Science 283:1183, 1999).

One possible mechanism by which deficient DC maturation and function may contribute to autoimmune disease such as type 1 diabetes includes insufficient antigen presenting cell activity for the generation of regulatory cells (Th2 cells, CD4+/CD25+ T cells) or for the induction of death in effector T cells. It is possible that intrinsic defects in the maturation of MDC may contribute to defects in NK T cell numbers or function. Likewise, defects in NK T cells my reciprocally limit DC maturation or lead to a failure to kill these antigen presenting cells, thus allowing a persistent and untoward immune response.

EXAMPLE 15

Methods for Determining the Effect of Antibodies on the Targeted T Cell Subpopulation In Vivo Any of the antibodies of the invention may be tested in an in vivo animal model to determine the pharmacological and pharmacokinetic properties of the antibodies. For example, the half-life, bio-distribution, and efficacy of the antibody may be determined.

One possible method involves the administration of human invariant T cells or any other T cell population of interest to a SCID or otherwise immune-deficient animal such as a mouse and administration of an anti-invariant T cell antibody or any other antibody of the invention to the animal to determine whether the antibody modulates the activity or number of the administered T cells in vivo.

In particular, a population of T cells that contains 1-10 million T cells of interest (e.g., invariant T cells or any other subpopulation of T cells) is administered i.v. or to any site of interest. One or more antibodies are administered, prior to, concurrent with, or following administration of the T cells. For example, the antibody may be administered at any point during the lifetime of the administered T cells in the host animal. Approximately 1-100 ug of the antibody is administered in the same site or in a different site as the site of administration of the T cells. If detectably labeled antibodies are used, the location and amount of administered antibody and/or T cells may be monitored in vivo based on fluorescence or radioactivity. Additionally, histology, immunological, and/or biochemical measurements may be performed ex vivo on tissues from the animal. The biological activity of the antibody or T cell subpopulation may be measured by analyzing the amount or activity of cytokines in a serum or tissue sample. Moreover, the activation of other cells, such as other T cells, by the administered T cell subpopulation may be measured. For example, the number of $CD69^+$ T cells may be measured by FACS sorting with an anti-CD69 antibody.

EXAMPLE 16

Administration of Antibodies for In Vivo Expansion of NK T Cells, CD1d-Reactive T Cells, or $J\alpha Q^+$ T Cells or for Imaging of these Cells The antibodies of the present invention may be administered to a mammal, possibly in addition to the administration of a cytokine, for the in vivo expansion of NK T cells, CD1d-reactive T cells, or $J\alpha Q^+$ T cells for the treatment or prevention of an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer. As described in Example 7, all modes of administration, dosing, and frequency are contemplated.

The pharmaceutical compositions containing one or more antibodies of the invention may be prepared as described previously in Remington's Pharmaceutical Sciences by E. W. Martin. Pharmaceutical stabilizing compounds, delivery vehicles, or carrier vehicles may be used. For example, human serum albumin or other human or animal proteins may be used. Phospholipid vesicles or liposomal suspensions are possible pharmaceutically acceptable carriers or delivery vehicles. These compositions can be prepared according to methods known to those skilled in the art.

An antibody of the invention that is covalently linked to a fluorescent label or radiolabel may be used to visualize the in vivo distribution, quantity, or migration of NK T cells, CD1d-reactive T cells, or $J\alpha Q^+$ T cells. This imaging of NK T cells, CD1d-reactive T cells, or $J\alpha Q^+$ T cells may be used to identify subjects who are at risk for or have an autoimmune disease, viral infection, bacterial infection, parasitic infection, infection by a eukaryotic pathogen, allergy, asthma, inflammatory condition, graft versus host disease, graft rejection, immunodeficiency disease, spontaneous abortion, pregnancy, or cancer. Alternatively, this method may be used to determine the effect of a therapy for one of the above diseases on NK T cells, CD1d-reactive T cells, or $J\alpha Q^+$ T cells.

OTHER EMBODIMENTS

From the foregoing description, it will be apparent that variations and modifications may be made to the invention described herein to adopt it to various usages and conditions. Such embodiments are also within the scope of the following claims.

All publications mentioned in this specification are herein incorporated by reference to the same extent as if each individual publication was specifically and individually indicated to be incorporated by reference.

---

What is claimed is:

1. A purified antibody, or a fragment or derivative thereof, that binds to the human CDR3 loop of a T cell receptor (TCR) α chain present on an invariant NKT cell, but does not substantially recognize and bind to other molecules in a biological sample which naturally includes other proteins or cells.

2. The purified antibody, fragment, or derivative of claim 1 that expands said invariant NKT cell.

3. The purified antibody, fragment, or derivative of claim 1, wherein said antibody is a monoclonal antibody, or a fragment or derivative thereof.

4. The purified antibody of claim 1, wherein said antibody is 6B11 (ATCC Deposit No. PTA-11305).

5. The purified antibody, fragment, or derivative of claim 1, wherein said antibody, fragment, or derivative binds the amino acid sequence CVVSDRGST (SEQ ID NO:2).

6. The purified antibody, fragment, or derivative of claim 1, wherein said antibody, fragment, or derivative has the same antigenic specificity as the 6B11 antibody.

7. The purified antibody, fragment, or derivative of claim 3, wherein said monoclonal antibody is a humanized antibody, or a fragment or derivative thereof, wherein said fragment is selected from the group consisting of F(ab')$_2$, Fab, and scFv.

8. The purified antibody, fragment, or derivative of claim 7, wherein said humanized antibody is a humanized form of 6B11, or a fragment or derivative thereof.

9. The purified antibody of claim 3, wherein said antibody is a monoclonal antibody.

10. The purified antibody of claim 5, wherein said antibody binds the amino acid sequence CVVSDRGST (SEQ ID NO:2).

11. The purified antibody of claim 6, wherein said antibody has the same antigenic specificity as the 6B11 antibody.

12. The purified antibody of claim 8, wherein said humanized antibody is a humanized form of 6B11.

13. The purified antibody of claim 7, wherein said monoclonal antibody is a humanized antibody.

* * * * *

UNITED STATES PATENT AND TRADEMARK OFFICE
CERTIFICATE OF CORRECTION

| | | |
|---|---|---|
| PATENT NO. | : 8,138,314 B2 | Page 1 of 1 |
| APPLICATION NO. | : 11/541958 | |
| DATED | : March 20, 2012 | |
| INVENTOR(S) | : Exley et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1166 days.

Signed and Sealed this
Twelfth Day of June, 2012

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 8,138,314 B2 | Page 1 of 2 |
| APPLICATION NO. | : 11/541958 | |
| DATED | : March 20, 2012 | |
| INVENTOR(S) | : Mark A. Exley et al. | |

It is certified that error appears in the above-identified patent and that said Letters Patent is hereby corrected as shown below:

On the Title Page

Page 2, Item (56) Other Publications, Probert et al., replace "$CD4^{30}$" with --$CD4^{+}$--;

Sottini et al., replace "$CD4^{30}$ and $CD8^{30}$" with --$CD4^{+}$ and $CD8^{+}$--;

van der Vliet et et al., replace "*Immunol.*" with --*Immunol.*--.

In the Specification

Column 13, Line 6, replace "pure.A" with --pure. A--;

Line 30, replace "interface.Additionally" with --interface. Additionally--.

Column 17, Line 8, replace "20, 20," with --20, 30,--;

Line 13, replace "is least" with --is at least--;

Line 14, replace "that" with --than--.

Column 8, Line 56, replace "8E-81" with --8E-8I--.

Column 20, Line 54, replace "versus α healthy" with --versus a healthy--.

Column 22, Line 25, replace "donor 0" with --donor O--.

Column 27, Line 9, replace "antibody.Additionally" with --antibody. Additionally--.

Column 32, Line 30, replace "6B11'-biotin" with --6B11-biotin--.

Column 34, Line 51, replace "anti-Vα,24," with --anti-Vα24,--.

Signed and Sealed this
Eleventh Day of March, 2014

Michelle K. Lee
*Deputy Director of the United States Patent and Trademark Office*

CERTIFICATE OF CORRECTION (continued)
U.S. Pat. No. 8,138,314 B2

Column 37, Line 10, replace "patents" with --patients--.

Column 40, Line 33-34, begin new line between cancer. and Methods;

Line 35, begin new line between reactivity and For;

Line 48, replace "µg/ml" with --pg/ml--.

Column 43, Line 14, replace "BCLXL" with --BCLxL--.

Column 44, Line 41, replace "to produced" with --to produce--.

Column 45, Line 1, replace "of sygneic" with --or syngenic--;

Line 11, replace "fours" with --four--.

Column 47, Line 46, replace "CD 1d" with --CD1d--.

Column 48, Line 17, replace "CD1 d" with --CD1d--;

Line 36, replace "development autoimmunity" with --development of autoimmunity--.

SEQUENCE LISTING

```
<160> NUMBER OF SEQ ID NOS: 3

<210> SEQ ID NO 1
<211> LENGTH: 17
<212> TYPE: PRT
<213> ORGANISM: Homo sapien

<400> SEQUENCE: 1

Cys Val Val Ser Asp Arg Gly Ser Thr Leu Gly Arg Leu Ala Asp Cys
1               5                   10                  15

Gly

<210> SEQ ID NO 2
<211> LENGTH: 9
<212> TYPE: PRT
<213> ORGANISM: Murine

<400> SEQUENCE: 2

Cys Val Val Ser Asp Arg Gly Ser Thr
1               5
```

```
<210> SEQ ID NO 3
<211> LENGTH: 9
<212> TYPE: PRT
<213> ORGANISM: Homo sapien

<400> SEQUENCE: 3

Cys Val Val Gly Asp Arg Gly Ser Ala
1               5
```